(12) United States Patent
Anvari

(10) Patent No.: US 11,137,474 B2
(45) Date of Patent: Oct. 5, 2021

(54) USE OF 5G IOT NETWORK TO NAVIGATE AND PROTECT MOVING OBJECTS IN A SMART ENVIRONMENT

(71) Applicant: Kiomars Anvari, Walnut Creek, CA (US)

(72) Inventor: Kiomars Anvari, Walnut Creek, CA (US)

(73) Assignee: Kiomars Anvari, Walnut Creek, CA (US)

(*) Notice: Subject to any disclaimer, the term of this patent is extended or adjusted under 35 U.S.C. 154(b) by 0 days.

(21) Appl. No.: 17/106,137

(22) Filed: Nov. 29, 2020

(65) Prior Publication Data

US 2021/0215787 A1 Jul. 15, 2021

Related U.S. Application Data

(63) Continuation-in-part of application No. 16/743,354, filed on Jan. 15, 2020, now Pat. No. 10,861,608, and a continuation-in-part of application No. 16/828,013, filed on Mar. 24, 2020, and a continuation-in-part of application No. 16/984,995, filed on Aug. 4, 2020, now Pat. No. 11,005,582.

(51) Int. Cl.
*G01S 5/00* (2006.01)
*G16Y 40/60* (2020.01)
*G05D 1/00* (2006.01)
*G01S 5/14* (2006.01)

(52) U.S. Cl.
CPC ............ *G01S 5/0072* (2013.01); *G01S 5/14* (2013.01); *G05D 1/0027* (2013.01); *G05D 1/0055* (2013.01); *G16Y 40/60* (2020.01)

(58) Field of Classification Search
CPC ......... G01S 5/0072; G01S 5/14; G16Y 40/60; G05D 1/0027; G05D 1/0055
See application file for complete search history.

(56) References Cited

U.S. PATENT DOCUMENTS

2015/0185713 A1* 7/2015 Glickfield ............ G05B 15/02
700/44
2020/0029172 A1* 1/2020 Kim .................. H04N 5/225

* cited by examiner

*Primary Examiner* — Walter J Divito

(57) ABSTRACT

Developing intelligent systems which take into consideration the economical, environmental, and safety factors of the modern society, is one of the main challenges of this century. Progress in the fields of mobile robots, control architectures, artificial intelligence, advanced technologies, and computer vision allows us to now envisage a smart environment future.
The rise of the connected objects known as the "Internet of Things" (IoT) will rival past technological marvels. This disclosure introduces a time synchronous communication IoT network and use of absolute time of day and a navigation/protection mechanism by various objects to navigate freely, without interference and collision in a smart environment.

15 Claims, 30 Drawing Sheets

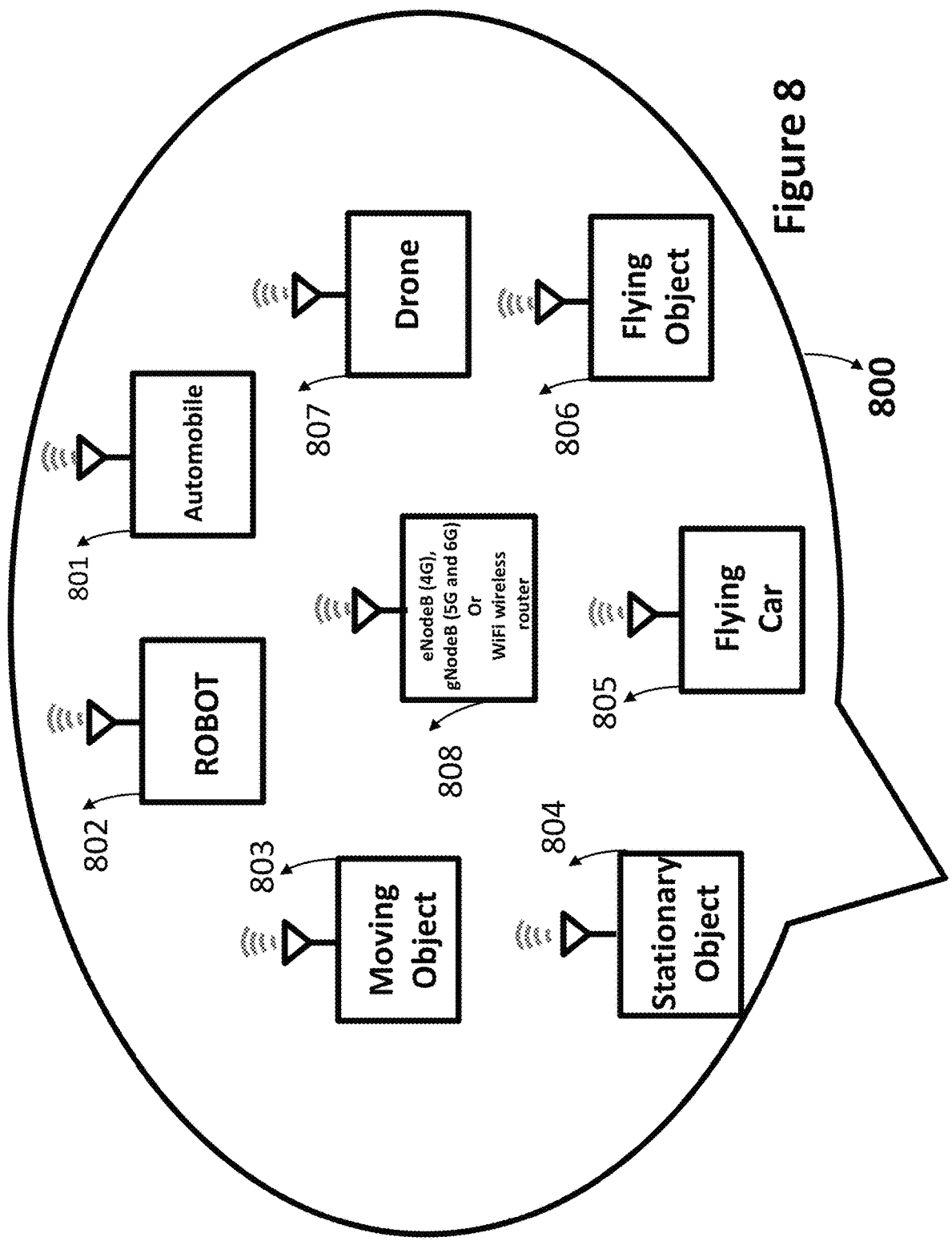

$x_1 \ldots\ldots x_n$  Are transmit samples within one Symbol Time

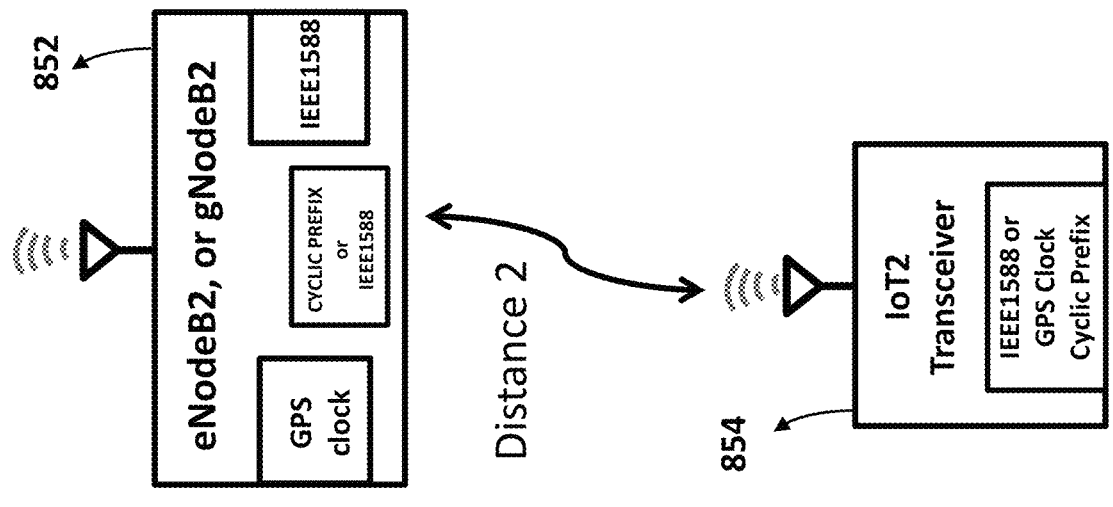
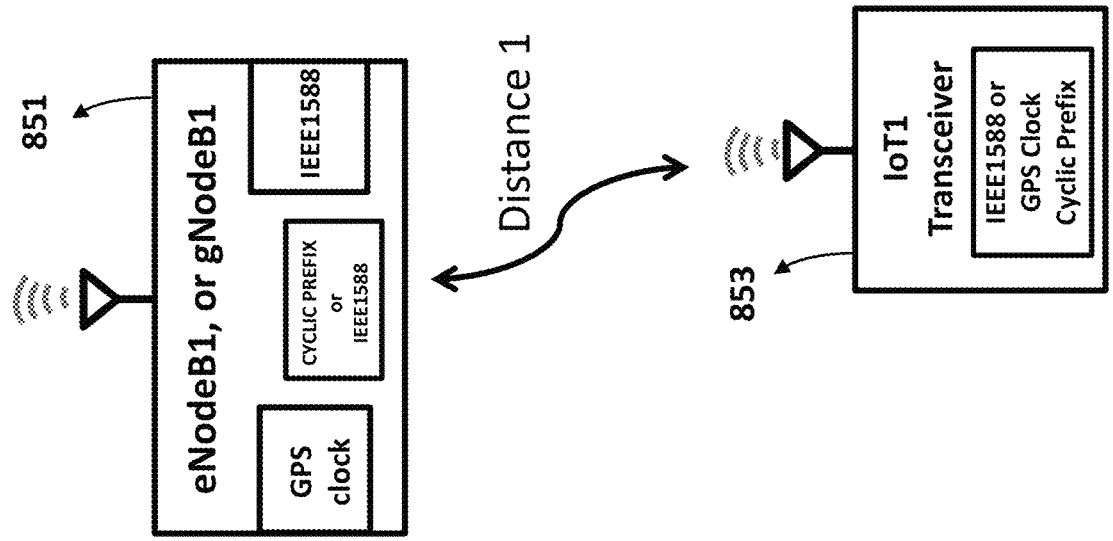
Figure 9G

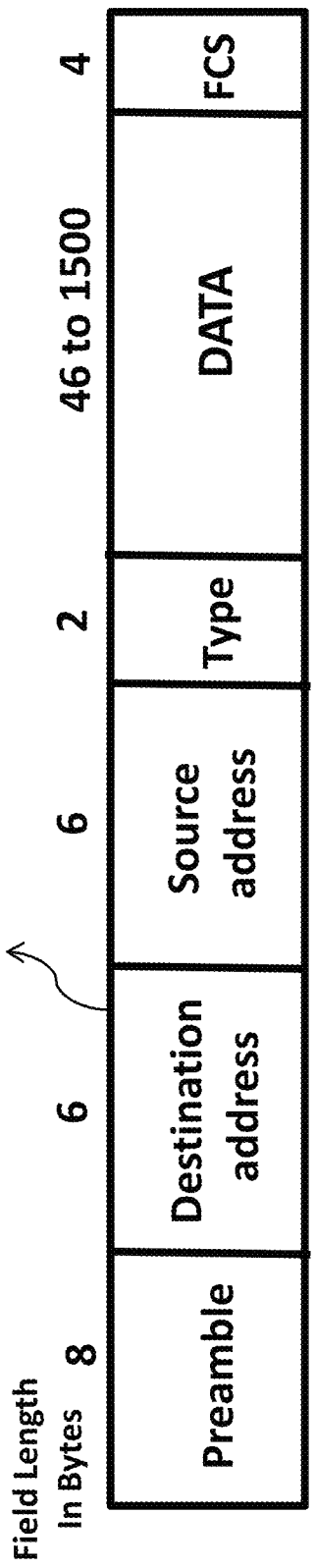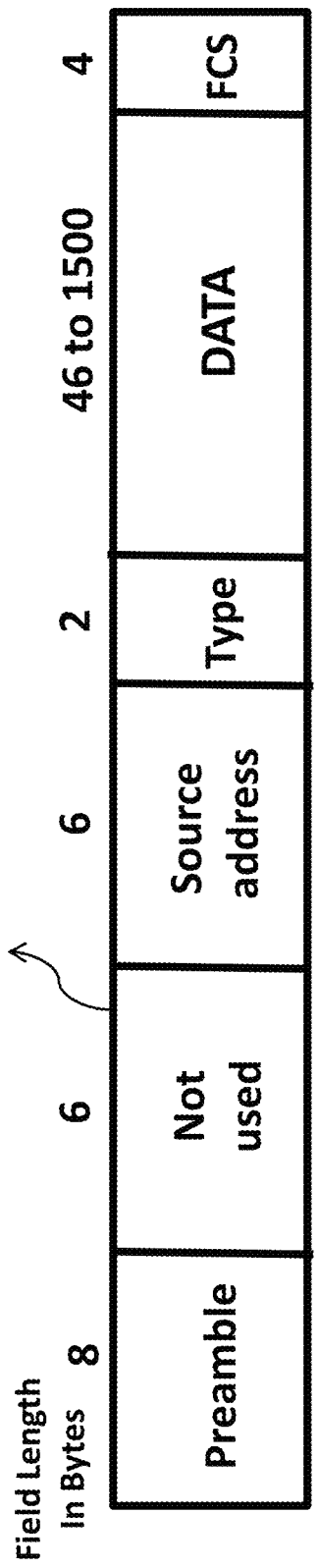
Figure 10A

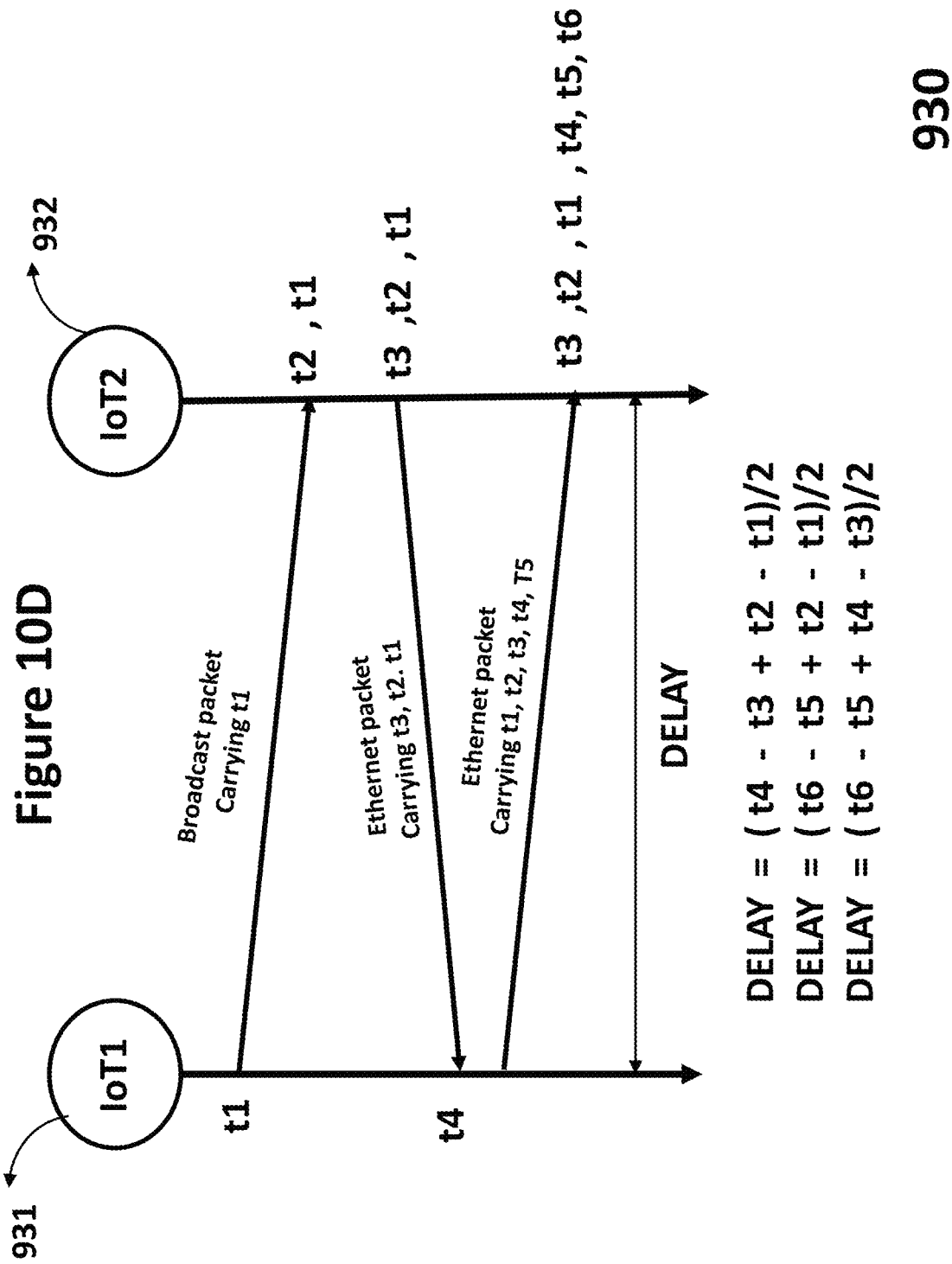

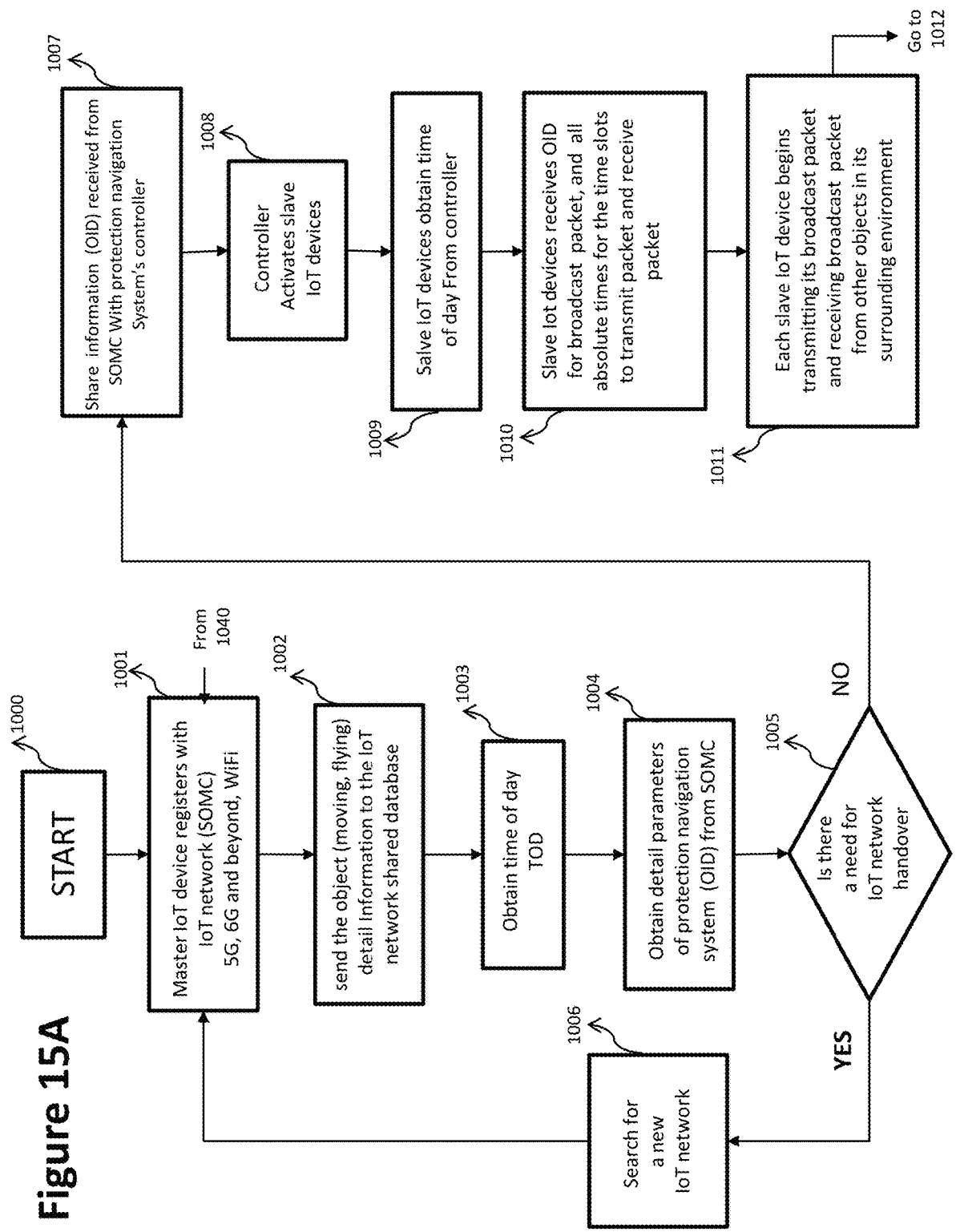

USE OF 5G IOT NETWORK TO NAVIGATE AND PROTECT MOVING OBJECTS IN A SMART ENVIRONMENT

The application claims priority to the following related applications and included here are as a reference.

Application: U.S. patent application Ser. No. 16/743,354 filed Jan. 15, 2020 and entitled "INTERNET OF THINGS (IOT) WITH NOVEL TIME OF DAY ACQUISITION".

Application: U.S. patent application Ser. No. 16/828,013 filed Mar. 24, 2020 and entitled "USE OF 5G IOT NETWORK FOR A VIRTUAL MEDICAL SYSTEM".

Application: U.S. patent application Ser. No. 16/984,995 filed Aug. 4, 2020 and entitled "USE OF 5G IOT NETWORK TO CONTROL MOVING OBJECTS IN A SMART ENVIRONMENT".

BACKGROUND

Developing intelligent systems which take into consideration the economical, environmental, and safety factors of the modern society, is one of the main challenges of this century. Progress in the fields of mobile robots, control architectures, artificial intelligence, advanced technologies, and computer vision allows us to now envisage a smart environment future.

It is safe to say that we are at the start of another industrial revolution. The rise of the connected objects known as the "Internet of Things" (IoT) will rival past technological marvels, such as the printing press, the steam engine, and electricity. From the developed world to developing world, every corner of the planet will experience profound economic resurgence. Even more remarkable is the speed with which this change will happen. A decade ago there were about one billion devices connected to internet. Today, there are close to 20 billion. In five year, it could be close to 50 billion.

The rise of IoT also means we are at the start of a new age of data. Two chief components of an "IoT object" are its ability to capture data via sensors and transmit data via the Internet. The declining cost of sensors since the start of the new millennium has been a main driver in the rise of IoT. In short, sensors are dirt cheap today. This has profound implications on the ability to capture data.

The Internet of Things (IoT) describes a worldwide network of intercommunicating devices. Internet of Things (IoT) has reached many different players and gained further recognition. Out of the potential Internet of Things application areas, Smart Cities (and regions), Smart Car and mobility, Smart Home and assisted living, Smart Industries, Public safety, Energy & environmental protection, Agriculture and Tourism as part of a future IoT Ecosystem have acquired high attention.

The Internet of Everything (IoE) is a concept that aims to look at the bigger picture in which the Internet of Things fits. Yet, when you look deeper at IoE, you'll notice it really is also about the vision of a distributed network with a growing focus on the edge in times of ongoing decentralization, some digital transformation enablers and a focus on IoT business outcomes.

While the Internet of Things today mainly is approached from the perspective of connected devices, their sensing capabilities, communication possibilities and, in the end, the device-generated data which are analyzed and leveraged to steer processes and power numerous potential IoT use cases, the Internet of Everything concept wants to offer a broader view.

The IoT based smart environments represent the next evolutionary development step in industries such as construction, manufacturing, transportation systems and even in sporting goods equipment. Like any functioning organism, the smart environment relies first and foremost on IoT sensor data from the real world. Sensory data comes from multiple sensors of different modalities in distributed locations. The smart environment needs information about all of its surroundings as well as about its internal workings.

The challenge is determining the prioritized hierarchy of: (1) detecting the relevant quantities, (2) monitoring and collecting the data, (3) assessing and evaluating the information, and (4) performing decision-making actions. The information needed by smart environments is provided by Distributed Sensor Systems, which are responsible for sensing as well as for the first stages of the processing hierarchy.

New types of applications can involve the electric vehicle and the smart house, in which appliances and services that provide notifications, security, energy-saving, automation, telecommunication, computers and entertainment are integrated into a single ecosystem with a shared user interface. Obviously, not everything will be in place straight away. Developing the technology, demonstrating, testing and deploying products, it will be much nearer to implementing smart environments by 2020. In the future computation, storage and communication services will be highly pervasive and distributed: people, smart objects, machines, platforms and the surrounding space (e.g., with wireless/wired sensors, M2M devices, etc.). The "communication language" will be based on interoperable protocols, operating in heterogeneous environments and platforms. IoT in this context is a generic term and all objects can play an active role thanks to their connection to the Internet by creating smart environments, where the role of the Internet has changed.

$5^{th}$ generation wireless systems (5G) are on the horizon and IoT is taking the center stage as devices are expected to form a major portion of this 5G network paradigm. IoT technologies such as machine to machine communication complemented with intelligent data analytics are expected to drastically change landscape of various industries. The emergence of cloud computing and its extension to fog paradigm with proliferation of intelligent 'smart' devices is expected to lead further innovation in IoT.

The existing 4G (fourth generation) networks have been widely used in the Internet of Things (IoT) and are continuously evolving to match the needs of the future Internet of Things (IoT) applications. The 5G (fifth generation) networks are expected to massive expand today's IoT that can boost cellular operations, IoT security, and network challenges and driving the Internet future to the edge. The existing IoT solutions are facing a number of challenges such as large number of connection of nodes, security, and new standards.

The drive to minimize human interaction in transportation vehicles is stronger than ever, especially in public transportation, automobiles, and etc. For instant, just a few years ago, automobiles seldom had very sophisticated safety systems. Now, it is rare to find an automobile without various safety and protection systems. And now new technology is evolving to the point of being able to offer preventive methods to better manage and dissipate sudden impact energy to the vehicle.

Today internet of things is a new revolution of the internet. A world where the real, digital and the virtual are converging to create smart environments that make energy, transport, cities and many other areas more intelligent.

Different types of application like water monitoring, water pollution, air pollution, forest fire detection, smart homes, smart cities where each things can connect from anywhere to anyplace to make our life easier.

In order to understand what are the constituents of IoE we will need to dive into the core parts of IoE. IoE is an umbrella term combining the following 4 properties in one place:

1. People:

People are the humans using connected devices to deliver insights about their personal and professional self. This data can include interests, preferences, work, personal health etc. Connecting this data to enterprise needs can provide insights relating the needs and desires of prospects for businesses. Additionally, this can be used to track performance and pain points of human resources.

2. Process:

The process is the way to ensure deliverability of right data at the right time to the right person or machine. Here data is more about insightful information or an action than just random chunk. Figuring out a way to decipher the right flow of information is a key to making the best use of big data.

3. Data:

With the increase in sources and types of data, we will also need to classify the information and analyze it to bring useful insights. Data alone is nothing but once combined with analytics and analysis this new data can help businesses in decision making and managing the organization.

4. Things:

This is where we come across the term Internet of Things (IoT). Internet of things is the interconnectivity of devices that send and receive information across networks like the internet. With every signal injected into the network, data is generated which needs to be collected, summarized and analyzed efficiently.

This application discloses a time synchronous communication IoT network and use of time of day by various objects to navigate freely, without interference and collision in a smart environment.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, an IoT network uses distributed IoT devices which are sensor/monitoring devices to monitor its surrounding environment and detect and collect data to be processed by the IoT network or a navigation and protection system.

In another aspect, an IoT device is a flying object, a moving object, and a stationary object.

In one aspect, an IoT is a robot, equipment, and a tool.

In one aspect, the IoT device is used for a navigation and protection system.

In one aspect, the navigation and protection system is used by various moving objects, flying vehicles/objects and stationary objects in order to protect them from any collision.

In another aspect, all communication links in the IoT network are asynchronous and use Ethernet packet protocols.

In one aspect, an IoT device uses Ethernet packet protocol for the over the air link between IoT network and IoT device.

In another aspect, an IoT device uses Internet Protocol (IP) packet for the over the air link between IoT network and IoT device.

In one aspect, the IoT devices use IEEE1588 (institute of electrical and electronic engineering 1588) precision time protocol (PTP) to achieve clock synchronization and obtain a time of day.

In another aspect, the IoT device uses IEEE1588 PTP to obtain time of day from the IoT network (4G, 5G, 6G, and WiFi networks).

In one aspect, an IoT device uses IEEE1588 PTP to obtain time of day from another IoT device.

In another aspect, the IoT device uses GPS (Global Positioning System) receiver to obtain location coordinates and time of day.

In one aspect, the IoT device frequency and phase synchronizes to IoT network using 4G, 5G, 6G, and WiFi (wireless fidelity) air protocol.

In another aspect, the IoT (IoE) network is $5^{th}$ generation (5G), $6^{th}$ generation (6G) fix and mobile data communication network.

In one aspect, IoT network is any fix and mobile data communication network beyond 5G such as $6^{th}$ generation (6G), $7^{th}$ generation (7G) and etc.

In another aspect, IoT network is a proprietary network.

In one aspect, IoT network is WiFi (wireless fidelity) network.

In another aspect, IoT is part of a satellite network supporting one of data communication standards like 5G, 6G, 7G or a proprietary data communication standard.

In another aspect, certain data collecting applications use multiple of sensors/monitoring devices but only one of them is a master and acts as IoT device that communicates with IoT network. All sensors/monitoring devices used in the data collecting application communicate among themselves using wired and/or wireless link.

In another aspect, in cases that a data collecting application uses multiple sensors/monitoring devices (IoT devices) each individual sensor/monitoring device (IoT device) used within the data collecting application has an IP (internet protocol) address or media access control (MAC) address and uses a proprietary or any standard protocol (such as IP protocol, Ethernet protocol) to communicate with other sensors used in the data collecting application similar to an IP communication network.

In one aspect, the IoT network uses the time of day to assign the IoT device an absolute time for data collection or its operation.

In another aspect, IoT network assigns an absolute time to each IoT device that is registered with IoT network to perform its activities.

In one aspect, the absolute time assigned by IoT network to various IoT devices is constant or dynamically changed depending on the time of day or load on the IoT network.

In one aspect, the absolute time assigned to IoT devices is different and has a window (time slot) that is enough to send information data to IoT network and other IoT devices as well as sufficient margin for any time of day error between various IoT devices.

In another aspect, IoT network shares the absolute times assigned to IoT devices with all IoT devices registered with IoT network.

In one aspect, IoT network shares all absolute times with all registered IoT devices without identifying which absolute time is assigned and which IoT device it is assigned to.

In another aspect, IoT network assigns an absolute time and a time window (time slot) for broadcasting and communication to each IoT device registered with the IoT network.

In one aspect, the time window assigned to each IoT device by IoT network is constant and identical for all registered IoT devices with IoT network, different for each IoT device, dynamically changed by IoT network, or requested by IoT device.

In one aspect, an IoT device registered with an IoT network can transmit and receive information data to and from other IoT devices without collision, and interference.

In another aspect, the IoT network uses the time of day to program the IoT devices an active time to collect data (or do other functions) and a sleep time or idle time to save power.

In one aspect, the IoT network uses the time of day to program the IoT device an absolute time to transmit collected data to (or communicate with) the IoT network or other IoT devices.

In one aspect, the absolute time is defined by the hour, the minute, the second, the millisecond, the microsecond, the nanosecond and the picoseconds.

In another aspect, the absolute time includes the hour.

In one aspect, the absolute time includes the hour and the minutes.

In one aspect, the absolute time includes the hour, the minutes, and the seconds.

In one aspect, the absolute time includes the hour, the minutes, the seconds, and the milliseconds.

In one aspect, the absolute time includes the hour, the minutes, the seconds, the milliseconds, and the microseconds.

In one aspect, the absolute time includes the hour, the minutes, the seconds, the milliseconds, the microseconds, and the nanoseconds.

In another aspect, the absolute time is only defined by minutes, by seconds, by milliseconds, by microseconds, by nanoseconds, or by picoseconds.

In another aspect, the absolute time hour is 0 to 24, minute is 0 to 60, second is 0 to 60, millisecond is 0 to 1000, microsecond in 0 to 1000, and nanosecond is 0 to 1000.

In one aspect, the absolute time is only defined by hour (0 to 24), by minutes (0 to 1440), by seconds (0 to 86400), by milliseconds (0 to 86400000) and so on.

In one aspect, the IoT network defines the date and time of day for data collection (or other functions).

In another aspect, the date is defined by the year, month, and day.

In one aspect, the IoT network or NPS specifies the date and absolute time an IoT device sends the collected data to (or communicate with) the IoT network or navigation and protection system's (NPS's) controller for processing.

In another aspect, the IoT network or NPS demands the IoT device to send its information data real time to IoT network or NPS's controller.

In one aspect, an IoT device comprises of a sensor/monitoring device and a wireless transceiver to communicate with IoT network as well as other IoT devices.

In another aspect, an IoT device is only a wireless transceiver that communicates with IoT network and obtains its data from one or more data collecting sensors that are externally attached to it.

In another aspect, a master IoT device collects data from other slave IoT devices and communicates them to the IoT network or NPS's controller.

In one aspect, the master IoT devices or slave IoT devices broadcast certain information data to other master IoT devices or slave IoT devices that are linked or belong to a specific smart environment.

In another aspect, the broadcast information data exchanged among IoT devices is used for any general or specific application.

In one aspect, the broadcast information data sent by IoT devices depends on the sensors/monitoring device used in the application.

In another aspect, the broadcast data is defined by IoT network or NPS.

In one aspect, the broadcast data is transmitted or received by an IoT device at an absolute time defined by IoT network.

In another aspect, the IoT devices exchange Ethernet packets.

In one aspect, IoT devices are identified by their IP addresses or media access control (MAC) address when communicating among themselves in a smart environment.

In another aspect, the IoT devices use Ethernet packet protocol to communicate among themselves.

In another aspect, the IoT devices use IP packet to communicate among themselves.

In one aspect, the IoT devices use a proprietary packet protocol to communicate among themselves.

In one aspect, the IoT devices use a WiFi protocol to communicate among themselves.

In another aspect, IoT devices support at least one of a BLUETOOTH transceiver, a ZIGBEE transceiver, a WiFi transceiver, and an Infrared transceiver.

In one aspect, the IoT devices use a 5G, 6G, 7G protocols to communicate among themselves.

In one aspect, a specific frequency band and channel is assigned to the IoT devices to communicate among each other.

In another aspect, the IoT device is a biometric device.

In one aspect, an IoT device is any object used in a factory.

In another aspect, an IoT device is any object used in a house.

In one aspect, an IoT device is any object used in a hospital.

In another aspect, an IoT device is any wearable device.

In one aspect, an IoT device is any object on a road, street, or highway inside and outside a city.

In another aspect, an IoT device is in general any equipment, object, tool, and device in an environment.

In one aspect, the IoT device has at least one sensor/monitoring device to collect data.

In another aspect, the IoT device does not have a sensor/monitoring device and consist of a transceiver.

In another aspect, the type of IoT device is identified by its type indicator.

In another aspect, the type of IoT device is identified by its serial number.

In one aspect, IoT device sends a time stamp in its broadcast data that shows the time of day at the antenna port of the transmitter of the IoT device's transceiver.

In another aspect, the IoT device's transceiver at the detector of its receiver detects the time of day the time stamp of the broadcast packet from another IoT device arrived at its own transceiver antenna port.

In one aspect, an IoT device uses its wireless transceiver to broadcast its type, identity code, location, mass, the time of day, and propagation time through its transceiver's transmitter up to antenna port.

In one aspect, the time of day that is broadcasted by an IoT device is in form of a time stamp which can be used to calculate distance.

In another aspect, the stationary object is a lamp post, a building, a tree, a stationary vehicle/object, a traffic light post, a statue, and any other stationary object in an environment.

In one aspect, an IoT device changes its carrier frequency and modulation for better, faster transmission and reception of information.

In one aspect, two IoT devices or objects use a protocol which is based on exchange of broadcast packets and Ethernet packets to obtain the distance and approaching speed between them.

BRIEF DESCRIPTION OF THE DRAWINGS

FIG. 8 illustrates moving vehicles, flying vehicles/objects, and stationary objects in an environment communicating with 4G, 5G and 6G Remote Radio Unit (RRU) and Radio Unit (RU) respectively FIGS. 9A through 9G depict an OFDM transmit signal with cyclic prefix, coverage, and time of day synchronization FIGS. 10A through 10F show an Ethernet frame and a broadcast frame signal transmission

FIGS. 15A through 15D depict the process steps to calculate environmental parameters The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1:
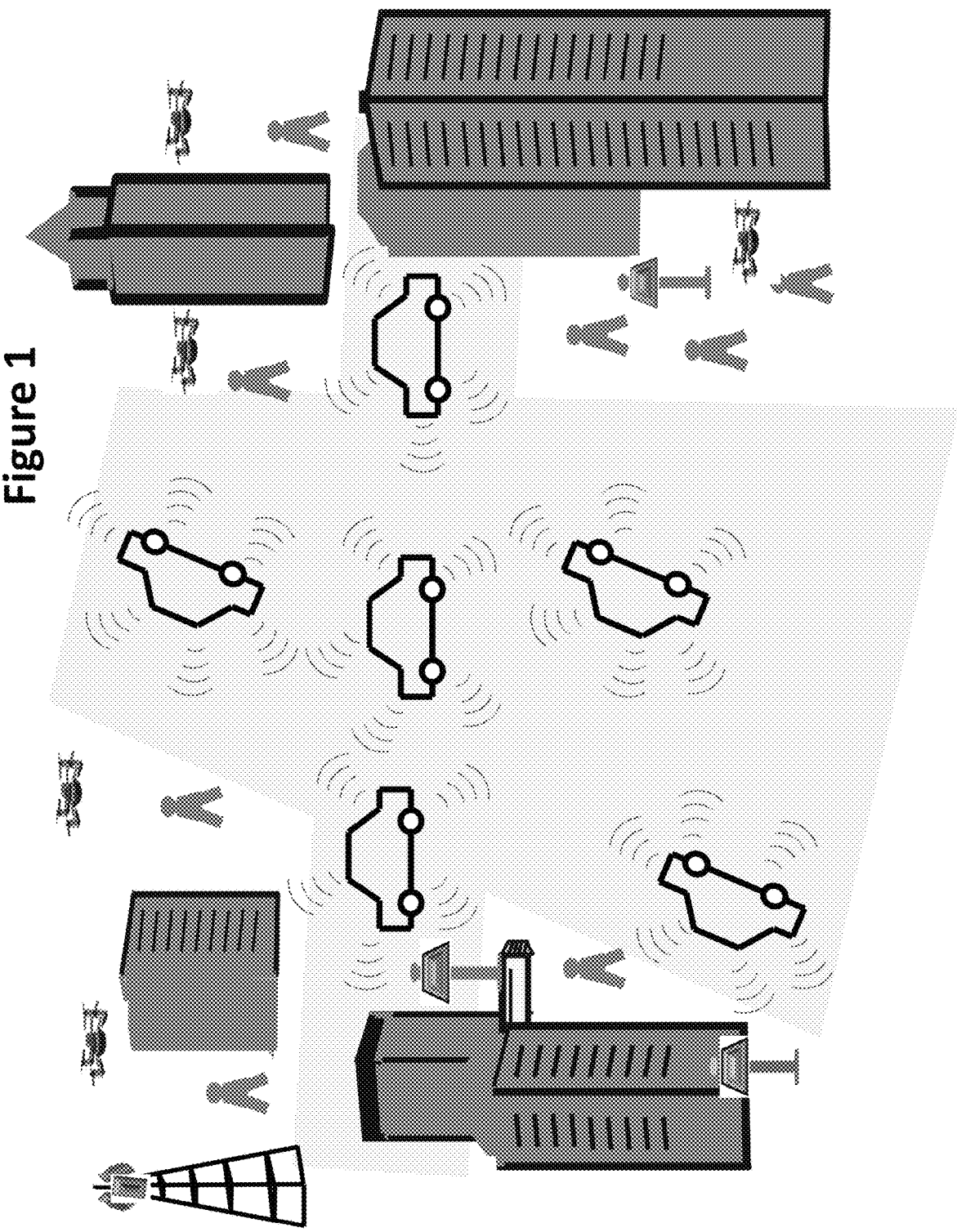
FIG. 1 illustrate a typical surrounding environment scenario for moving, flying vehicles/objects and stationary objects as IoT devices

FIG. 1 illustrates a typical environment with moving and stationary objects. The stationary objects are trees, lamp posts, small cells, buildings, street floors, walking payments, parked vehicles, statues, houses, hospitals, gas stations, schools, sport fields, shopping malls, small shops, department stores, parking lots, and any other stationary objects. Stationary objects are identified by their types, an IP addresses, shapes, masses, and locations. Stationary objects act as an IoT device or IoT devices with a single IP address or independent IP addresses. Large building at different sides requires different IoT devices representing different locations and sides.

The moving vehicles are robots, humans with body armor, humans, animals, automobiles, trucks, boats, ships, bicycles, motorcycles, moving objects in a factory, moving objects in a hospital, moving objects used in buildings, and any other moving objects.

The flying vehicles are helicopters, small planes, large planes, flying humans, flying robots, gliders, flying cars, drones, missiles, birds, and any other flying objects.

Figure 2:
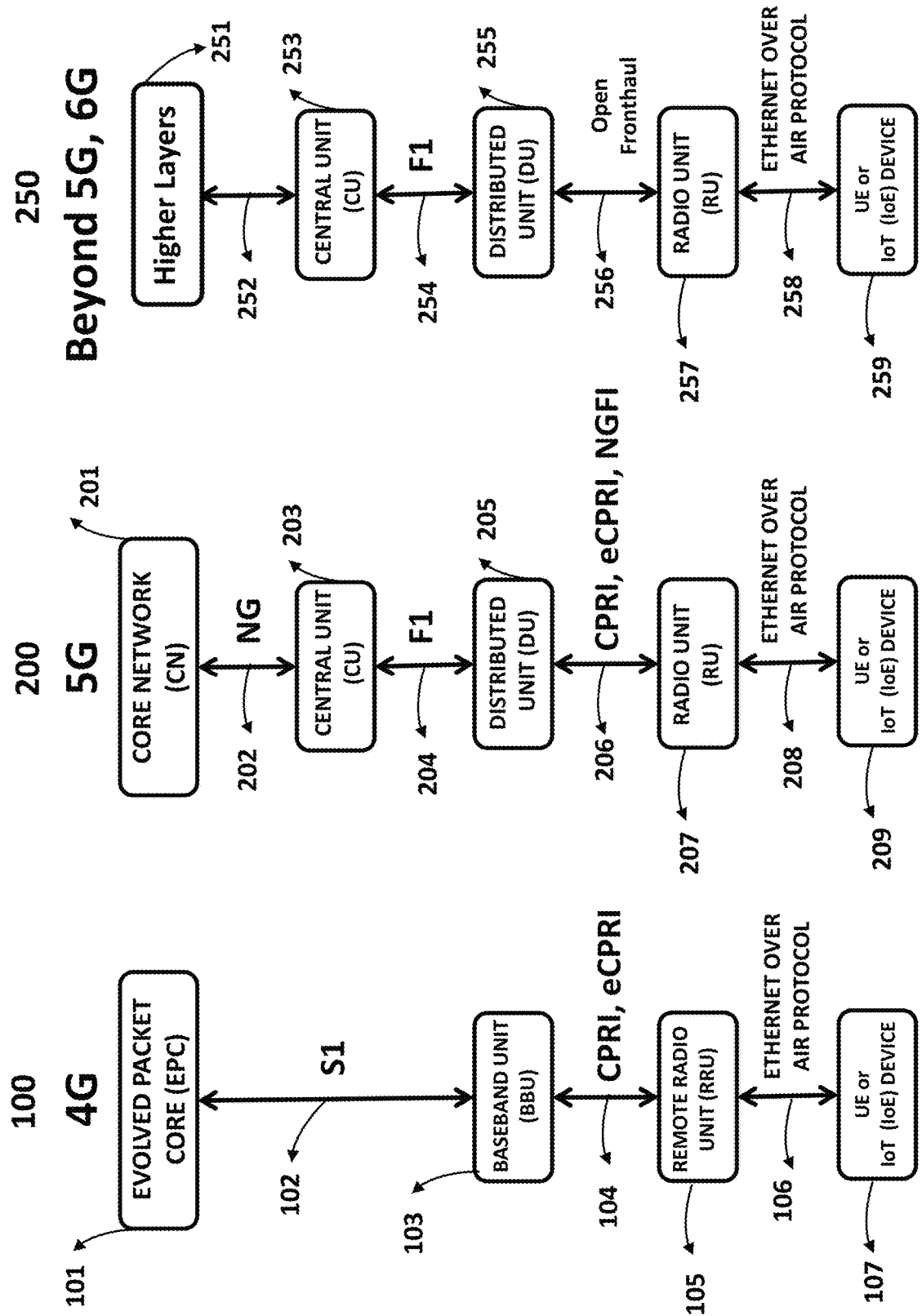
FIG. 2A illustrates 4G IoT (IoE) Network
FIG. 2B illustrates 5G IoT (IoE) Network
FIG. 2C shows beyond 5G and 6G IoT (IoE) network

FIG. 2A depicts 4G (core, eNodeB, and UE or IoT device) end to end IoT network 100 and FIG. 2B illustrates 5G (core, gNodeB, UE or IoT device) end to end IoT network 200 supporting cloud radio access network C-RAN and virtual radio access network vRAN. The 4G network 100 facilitate communication between user equipment (UE) or IoT device 107 and evolved packet core (EPC) 101 through remote radio unit (RRU) 105 and baseband unit (BBU) 103 using over the air protocol interface 106, evolved common public radio interface (eCPRI) 104 and "S1" interface 102. The RRU 105 and BBU 103 are components of evolved Node B (eNodeB) of 4G network. 5G network 200 facilitate communication between user equipment (UE) or IoT device 209 and core network (CN) 201 through radio unit (RU) 207, distributed unit (DU) 205, and central unit (CU) 203 using over the air protocol interface 208, evolved common public radio interface (eCPRI) or next generation fronthaul interface (NGFI) 206, F1 interface 204 and "NG" interface 202. The RU 207, DU 205, and CU 203 are components of 5G new radio (NR) which is also called gNodeB. Both UEs 107 and 109 also act as IoT (IoE) device.

The 4G network 100 uses different architectures depending on applications. In small cells BBU 103 and RRU 105 are collocated and there is no need for CPRI or eCPRI interface 104. A small cell connects to evolved packet core 101 through "S1" interface 102 which uses Ethernet protocol. CPRI is a synchronous protocol which is used between RRU 105 and BBU 103. The eCPRI uses Ethernet to encapsulate CPRI and is an asynchronous interface protocol between RRU 105 and BBU 103. The "S1" interface between BBU 103 and EPC 101 uses Ethernet protocol. The 5G network 200 also uses different architectures depending on applications that the network is used for. In certain architectures one or more network components are collocated. When one or more network components are collocated the components use the interfaces defined in the standard. However, there are cases such as a small cell when two or more components of network are co-located and the interfaces may be eliminated.

When Ethernet protocol is used between two ports there is a need for synchronization. There are a number of synchronization techniques that are used in data communication networks and the most common one depending on requirements of the network components or ports are syncE, PTP or IEEE1588, NTP, and GPS. The Network Time Protocol (NTP) is a networking protocol for clock synchronization between computer systems over packet-switched, variable-latency data networks. In operation since before 1985, NTP is one of the oldest Internet protocols in current use. Synchronous Ethernet, also referred to as SyncE, is an ITU-T standard for computer networking that facilitates the transference of clock signals over the Ethernet physical layer. This signal can then be made traceable to an external clock. IEEE 1588 Precision Time Protocol (PTP) is a packet-based two-way communications protocol specifically designed to precisely synchronize distributed clocks to sub-microsecond resolution, typically on an Ethernet or IP-based network. Global Satellite Positioning System (GPS) signal is received, processed by a local master clock, time server, or primary reference, and passed on to "slaves" and other devices, systems, or networks so their "local clocks" are likewise synchronized to coordinated universal time (UTC).

In both 4G (core plus eNodeB) network 100 and 5G (core plus gNodeB) network 200 when the link between two network ports is Ethernet then there is a need to synchronize the two network components using SyncE, IEEE1588 (PTP) or NTP depending on requirements and specification of two network components. "S1" interface in 4G networks, "F1" interface and "NG" interface in 5G networks use Ethernet packet protocol and IEEE1588 is widely used for synchronization between two network ports.

In case of RU 107 and RRU 105 when CPRI is used as the interface protocol clock synchronization is possible because CPRI is a synchronous protocol. When eCPRI which is an asynchronous protocol is used for RU and RRU interface to DU and BBU there is a need for one of the above mentioned synchronization techniques. If only clock synchronization is needed then syncE protocol is sufficient. However, when time of day is a requirement then IEEE1588 (PTP) or GPS needs to be used.

Mobile user equipment (UE) 107 and 109 use GPS to obtain the time of day/location and over the air protocol to achieve frequency and phase synchronization. However, for UEs or IoT devices that either can't see the GPS satellites, GPS signal is very weak, or GPS receiver increases cost, size, and power consumption another technique to acquire time of day is require. UEs and IoT devices can use their received 4G and 5G signal to achieve frequency and phase synchronization. UEs and IoT devices that do not have access to GPS signal can either obtain time of day from UEs and IoT devices in surrounding environment that have access to GPS signal and are accessible or obtain it from RUs and RRUs that they communicate with.

There are three techniques that UEs and IoT devices can use to obtain time of day from gNodeBs and eNodeBs. The precision of the time of day will be different using these three techniques. The time of day with different accuracies are used for different applications. The less accurate time of day uses one way communication between RU 207, RRU 105 and UEs or IoT devices 209, and 107 and the more accurate time of day (provided the total propagation delay within uplink of gNodeB or eNodeB and uplink of UE is equal to the total propagation delay within downlink of gNodeB or eNodeB and downlink of UE) uses two way communications between RU 207, RRU 105 and UEs or IoT devices 209, and 107. In both methods RU 207 and RRU 105 should have the time of day. In 4G network 100 and 5G network 200 for architectures that RU 207 and RRU 105 do not have the time of day or can't support exchange of time of day with UEs and IoT devices then the network component prior to RU and RRU which are DU 205 and BBU 103 can be used to propagate the time of day to UEs and IoT devices 209, and 107. The same applies to DU 205 and BBU 103. When DU and BBU do not have the time of day then CU 203 and EPC 101 can be used to propagate the time of day to UEs or IoT devices 209, and 107.

In one embodiment, 4G network 100 and 5G (6G) network 200 (250) provide the time of day to UEs and IoT devices, using institute of electrical and electronic engineering (IEEE1588) precision time protocol (PTP). IEEE1588 PTP exchange the timing messages to and from UEs or IoT devices and one component of 4G network 100 and 5G (6G) network 200 (250).

In one embodiment, IEEE1588 PTP messages are exchanged between UEs or IoT devices and one of RRU 105, BBU 103, or EPC101.

In another embodiment, IEEE1588 PTP messages are exchanged between UEs or IoT devices and one of RU 207 or 257, DU 205 or 255, or CU 203 or 253.

In one embodiment of 4G network 100, the time of day is sent to UEs and IoT devices by cyclic prefix of OFDM (orthogonal frequency division multiplexing) symbols from at least one of RRU 105, or BBU 103 depending which network component performs IFFT (inverse fast Fourier Transform).

In another embodiment of 5G network 200 or 6G (7G) network 250, the time of day is sent to UEs and IoT devices by cyclic prefix of OFDM symbols from at least one of RU 207 (257), or DU 205 (255) based on which network component performs IFFT (inverse fast Fourier Transform).

In one embodiment, 4G and 5G (or beyond 5G, 6G and 7G) networks 100, 200 and 250 utilize unused downlink sub-carriers to send the time of day to UEs or IoT devices 107, 209, and 259.

In another embodiment, 4G and 5G (or beyond 5G, 6G and 7G) networks 100, 200 and 250 utilize unused bits or messages in various downlink channels to send the time of day to UEs or IoT devices 107, 209, and 259.

In one embodiment, 5G, 6G, and 7G networks transmit Ethernet (or IP) packets over the air to UEs or IoT devices in order to have an end-to-end network using a single packet protocol. By doing this both hardware and software is significantly simplified.

In another embodiment, UEs and IoT devices obtain time of day from other UEs or IoT device in surrounding environment that are in their communication range and have time of day.

In one embodiment, UEs and IoTs devices use another frequency to communicate with other UEs and IoT devices in surrounding environment and exchange broadcast data.

In another embodiment, UEs and IoT devices communicate with other UEs and IoT devices by exchanging Ethernet (or IP) packets or any other proprietary packets.

In one embodiment, UEs and IoT devices use similar physical layer as 4G, 5G or 6G (7G) to communicate with other UEs and IoT devices in their surrounding environment without introducing any unwanted interference.

In another embodiment, UEs and IoT devices use a physical layer different from 4G, 5G, 6G (7G) to communicate with other UEs and IoT devices in their surrounding environment without introducing any unwanted interference.

In one embodiment, UEs and IoT devices communicate with WiFi network or any other proprietary network to obtain time of day and other information in their surrounding environment.

In another embodiment, a specific time is defined and communicated to UEs and IoT devices by 4G, 5G, and 6G (or 7G) networks for broadcasting or communication with other UEs or IoT devices in order to avoid interruption and interference.

In another embodiment, a specific channel is defined and communicated to UEs and IoT devices by 4G, 5G, and 6G (or 7G) networks for broadcasting or communication with other UEs or IoT devices in order to avoid interruption and interference.

In one embodiment, UEs and IoT devices support Bluetooth, Zigbee, infrared, GPS, WiFi, and any other wireless communication systems to communicate with other UEs and IoT devices in their surrounding environment and exchange information data and transmit and receive broadcast data.

In another embodiment, UEs and IoT devices transmit and receive broadcast data that includes the type of UE and IoT device, their IP address, their location, their mass, time of day, method of obtaining the time of day (IEEE1588, cyclic prefix, GPS, or other methods) and propagation time through its transceiver's transmitter up to antenna port.

In one embodiment, UEs or IoT devices broadcast the time of day at their transmitter antenna port to other UEs or IoT devices in their surrounding environment.

In one embodiment, UEs and IoT devices support WiFi, Bluetooth, Infrared, and Zigbee over the air wireless protocols.

Cloud radio access network or C-RAN architectures shown in FIGS. 2A and 2B enables cost saving on expensive baseband resources, in which the baseband units are shared in a centralized baseband pool. Therefore, the computing resources can be utilized optimally based on the demand. C-RAN architecture has also opened up an opportunity for RAN virtualization (vRAN) in order to further reduce cost. Therefore, virtual RAN or vRAN has been developed to simplify the deployment and management of the RAN nodes and make the platform readily available for multitude of dynamically changing service requirements. The main issue with C-RAN and vRAN is that these architectures still utilize propriety software, hardware and interfaces which lack openness as a major bottleneck in efficiently utilizing virtualization. In order to overcome the limitations of C-RAN and vRAN, O-RAN is emerging as a new RAN architecture that uses open interfaces between the elements implemented on general-purpose hardware. This allows operators select RRU or RU and BBU or DU hardware and software from different vendors. In addition, open interfaces between decoupled RAN components provide efficient multi-vendor interoperability. O-RAN architecture also allows enhanced RAN virtualization that supports more efficient splits over the protocol stack for network slicing purpose. O-RAN further reduces RAN expenditure by utilizing self-organizing networks that reduce conventional labor intensive means of network deployment, operation and optimization. In addition to cost reduction, intelligent RAN can handle the growing network complexity and improve the efficiency and accuracy by reducing the human-machine interaction.

FIG. 2C shows the O-RAN end to end architecture (UE, gNodeB, and core) 250 for beyond 5G and 6G. Higher layers 251 communicate with open interface 252 to central unit 253. The interface between central unit (CU) 253 and distributed unit (DU) 255 is open interface 254 "F1" and the interface between distributed unit 255 and radio unit (RU) 257 is open fronthaul 256. UE or IoT device 259 use over the air interface 258 to communicate with RU 257. Therefore, the only difference between 5G, beyond 5G and 6G ORAN architecture is open interface 252, open "F1" interface 254 and open fronthaul 256.

All embodiments related to 5G explain above apply to beyond 5G and 6G (7G) ORAN.

Figure 3:
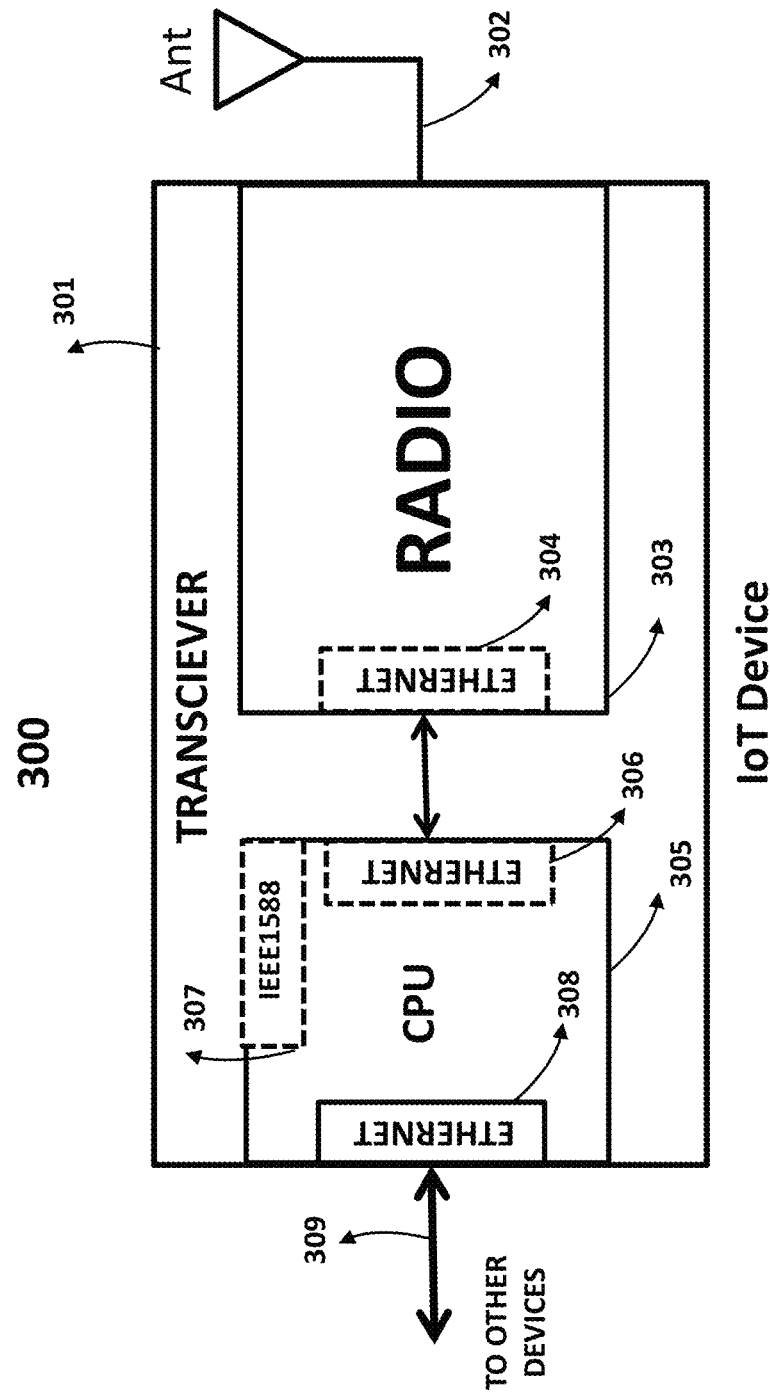
FIG. 3 illustrates a typical IoT device that can be found in an environment communicating with cellular network

FIG. 3 illustrate the architecture of an IoT device 300. In general IoT device 300 communicates with 4G, 5G and 6G (or 7G) networks to exchange information data. IoT device 300 through radio 303 attaches itself to a 4G, 5G, or 6G (7G) network in its surrounding environment and listens to commands to perform certain functions. Radio 303 when receives a command sends it to CPU 305 to be evaluated and performed by CPU 305 or uses other devices that are connected to CPU 305 to perform the command or commands. Then the results obtained from performing the commands through CPU 305 and radio 303 is transmitted to 4G, 5G, or 6G (7G) network for analysis.

In one embodiment, IoT device 300 includes among other things transceiver 301 which consists of antenna 302, radio 303, possible radio Ethernet port 304, CPU 305, possible Ethernet port 306 towards radio, possible IEEE1588 PTP 307, and Ethernet port 308 towards other devices.

In one embodiment, IoT device 300 through antenna 302 and radio 303 attaches to 4G, 5G, or 6G (7G) IoT network and if needed obtains the time of day.

In another embodiment, IoT device transceiver 301 obtains the time of day through IEEE1588 PTP, downlink transmit cyclic prefix, downlink transmit unused sub-carriers, or unused bits or messages in one of downlink channels from 4G, 5G, or 6G (7G) IoT network.

In one embodiment, IoT device 300 communicates via its transceiver's CPU 305 with another device using an Ethernet port 308.

In another embodiment, IoT device 300 propagates the time of day to an external device or equipment via its transceiver's Ethernet port 308 and link 309 using IEEE1588 PTP 307.

In one embodiment, IoT device 300 receives commands or information data from 4G, 5G, or 6G (7G) IoT network and communicates the commands to an external device through its transceiver's Ethernet port 308.

In one embodiment, IoT device 300 receives information data from an external device through its Ethernet port 308 and transmits it to 4G, 5G, or 6G (7G) IoT network using its transceiver's radio 303 and antenna 302.

In another embodiment, IoT device 300 communicates to an external device via its transceiver's CPU 305 using a serial interfaces or a parallel interface instead of Ethernet interface 308.

In one embodiment, IoT device 300 communicates with other IoT devices and exchange broadcast data. The IoT device 300 uses a different frequency or channel to communicate with another IoT device in order to avoid interruption and interference.

In another embodiment, IoT device 300 communicates with other IoT devices in its surrounding environment that are in its communication range using a proprietary physical layer or a physical layer similar to 4G, 5G, or 6G (7G) network.

In one embodiment, IoT device 300 exchanges Ethernet packets or any other proprietary packets with other IoT devices in its surrounding environment.

In another embodiment, IoT device 300 communicates with a WiFi network in its surrounding environment.

In one embodiment, IoT device 300 through its transceiver 301 supports WiFi, Bluetooth, Zigbee, and Infrared over the air wireless protocols.

In one embodiment, IoT device exchange IEEE1588 PTP messages with another IoT device or a WiFi router in surrounding environment to obtain or propagate the time of day.

In another embodiment of IoT device 300, the device that is connected to transceiver 301 through link 309 is any device or object that is remotely controlled to perform certain function.

Figure 4:
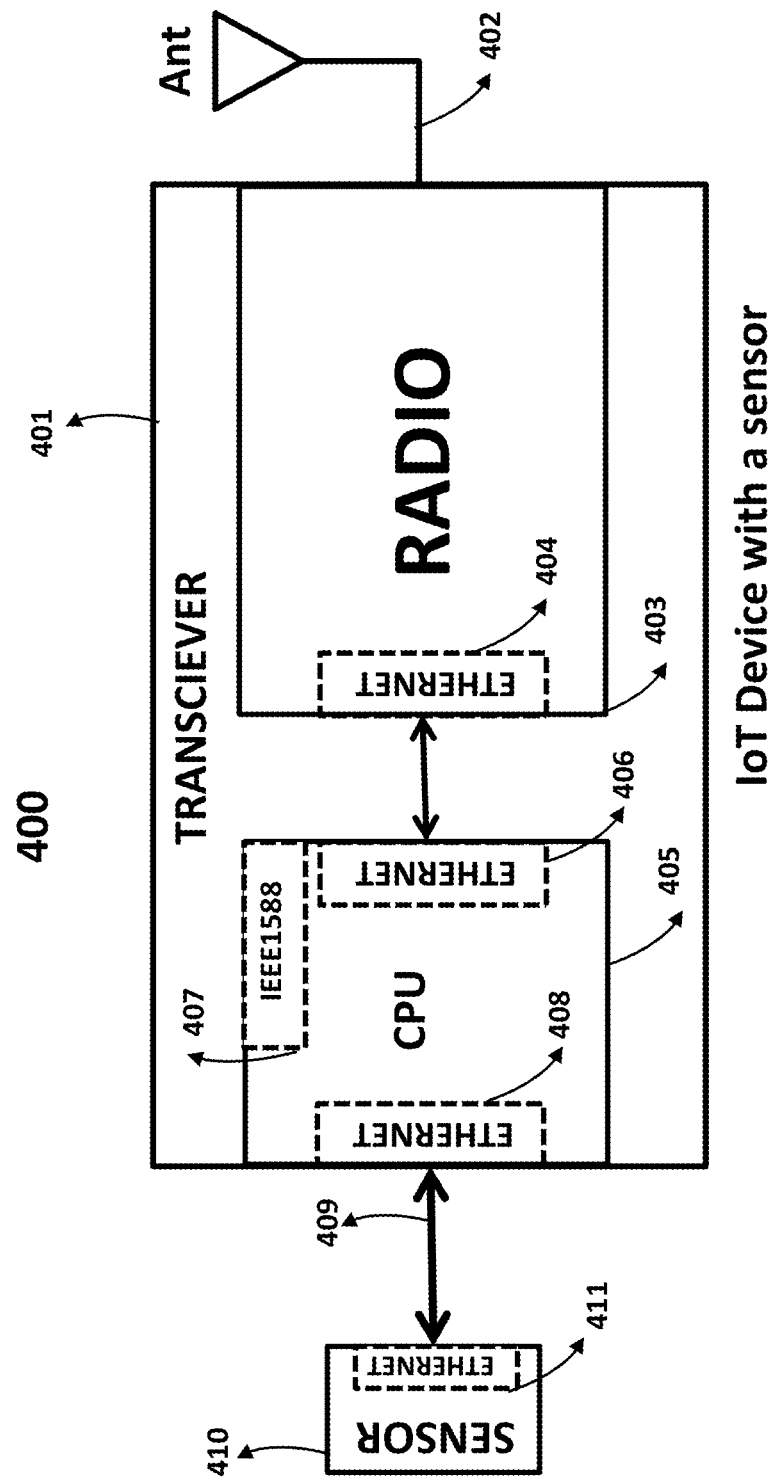
FIG. 4 illustrates a typical IoT device that can be found in an environment communicating with cellular network with a single sensor

FIG. 4 shows the architecture of an IoT sensor device 400. In general IoT sensor device 400 communicates with 4G, 5G, and 6G (7G) networks to exchange information data. IoT sensor device 400 through radio 403 attaches itself to a 4G, 5G, or 6G (7G) network in its surrounding environment and listens to commands to activate sensor 410. Radio 403 when receives a command, sends it to CPU 405 to be evaluated and performed by CPU 405 or sensor 410 that is connected to CPU 405. Then the results obtained from performing the commands through CPU 405 and radio 403 is transmitted to 4G, 5G, or 6G (7G) network for analysis.

In one embodiment, IoT sensor device 400 includes, among other things transceiver 401 which consists of antenna 402, radio 403, possible radio Ethernet port 404, CPU 405, possible Ethernet port 406 towards radio, possible IEEE1588 PTP 407, possible Ethernet port 408 and sensor 410 with possible Ethernet port 411.

In one embodiment, IoT sensor device 400 uses an attached sensor 410.

In another embodiment, IoT sensor device 400 uses an external device which is a sensor 410.

In one embodiment, IoT sensor device 400 uses an external sensor 410 that communicates with transceiver 401 using Ethernet packet protocol through Ethernet ports 411 and 408.

In another embodiment, the link 409 between Ethernet port 408 of transceiver 401 and Ethernet port 411 of sensor 410 is a wired link or a wireless link.

In another embodiment of IoT sensor device 400, the wired 409 link is a standard serial interface, a proprietary serial interface, or a parallel interface.

In one embodiment of IoT sensor device 400, the wireless link 409 between transceiver 401 and sensor 410 is at least one of Bluetooth, Zigbee, WiFi, Infrared, or any proprietary wireless link.

In another embodiment of IoT sensor device 400, the sensor 410 does not necessarily sense anything. Sensor 410 is a tool, equipment, a robot hand, an on/off switch, any activation or deactivation device, and any device, equipment or object that is remotely controlled to perform certain function.

Figure 5:
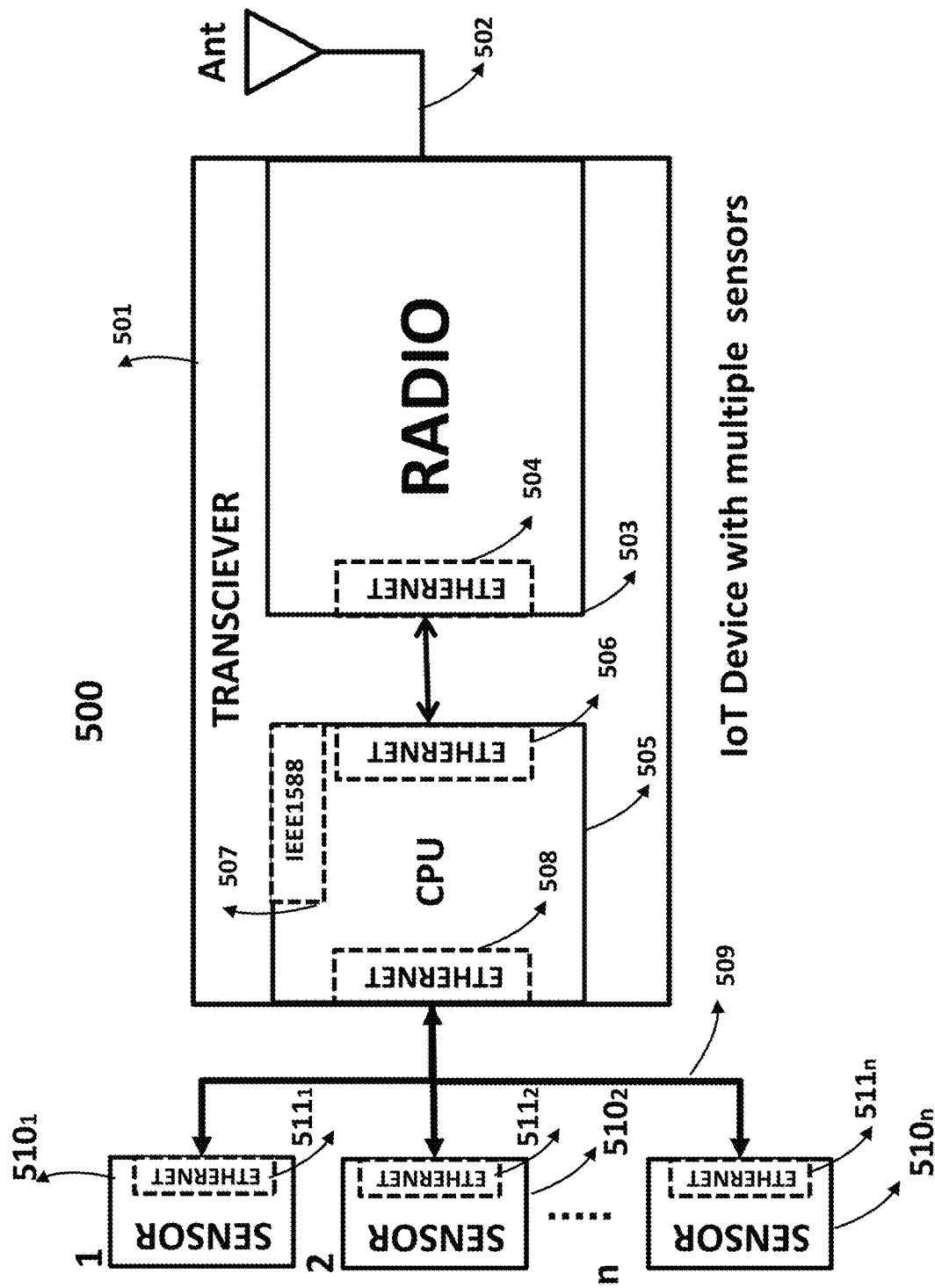
FIG. 5 depicts a typical IoT device that can be found in an environment communicating with cellular network with multiple sensors

FIG. 5 shows the architecture of an IoT sensor network 500. In general IoT sensor network 500 communicates with 4G, 5G, and 6G (7G) networks to exchange information data. IoT sensor network 500 through radio 503 attaches itself to a 4G, 5G, or 6G (7G) network in its surrounding environment that supports Internet of Things and listens to commands to activate sensor network $510_1$ to $510_n$. Radio 503 when receives a command, sends it to CPU 505 to be evaluated and performed by CPU 505 or sensor network $510_1$ to $510_n$ that is connected to CPU 505. Then the results obtained from performing the commands through CPU 505 and radio 503 is transmitted to 4G, 5G, or 6G (7G) network for analysis.

In one embodiment, IoT sensor network 500 includes among other things transceiver 501 which consists of antenna 502, radio 503, possible radio Ethernet port 504, CPU 505, possible Ethernet port 506 towards radio, possible IEEE1588 PTP 507, possible Ethernet port 508 and sensor network $510_1$ to $510_n$.

In another embodiment, IoT sensor network 500 uses an external monitoring sensor network $510_1$ to $510_n$ that can perform various functions autonomously or through commands that sent to it remotely.

In one embodiment, IoT sensor network 500 uses an external sensor network $510_1$ to $510_n$ that communicates with transceiver 501 through Ethernet ports $511_1$ to $511_n$.

In another embodiment, the sensor network $510_1$ to $510_n$ can be a monitoring network $510_1$ to $510_n$ or a mix of sensors, monitoring devices, autonomous devices, IoT devices and remotely controlled devices or equipments $510_1$ to $510_n$.

In one embodiment, each device within network of devices $510_1$ to $510_n$ has an IP (internet protocol) address that identifies the device.

In another embodiment, each device within network of devices $510_1$ to $510_n$ uses its serial number for its identity.

In one embodiment of IoT sensor network 500, at least one of an Ethernet packet and a proprietary packet is used for communication between transceiver 501 and devices/equipment $510_1$ to $510_n$.

In another embodiment, the link 509 between Ethernet port 508 or port 508 of transceiver 501 and Ethernet ports $511_1$ to $511_n$ or ports $511_1$ to $511_n$ of devices $510_1$ to $510_n$ is a wired link, a wireless link or a mix of wired and wireless.

In another embodiment of IoT sensor network 500, the wired link 509 is a standard serial interface, a proprietary serial interface, or a parallel interface.

In one embodiment of IoT sensor network 500, the wireless link 509 between transceiver 501 and devices $510_1$ to $510_n$ is at least one of Bluetooth, Zigbee, WiFi, Infrared, or any proprietary wireless link.

In one embodiment, IoT sensor network 500 receives an absolute time from 4G, 5G, 6G (or 7G), or WiFi network for its various activities as well as scheduling activities of the external devices connected to IoT sensor network 500.

In one embodiment of the IoT sensor network 500, the sensor network $510_1$ to $510_n$ are slave IoT network $510_1$ to $510_n$.

Figure 6:
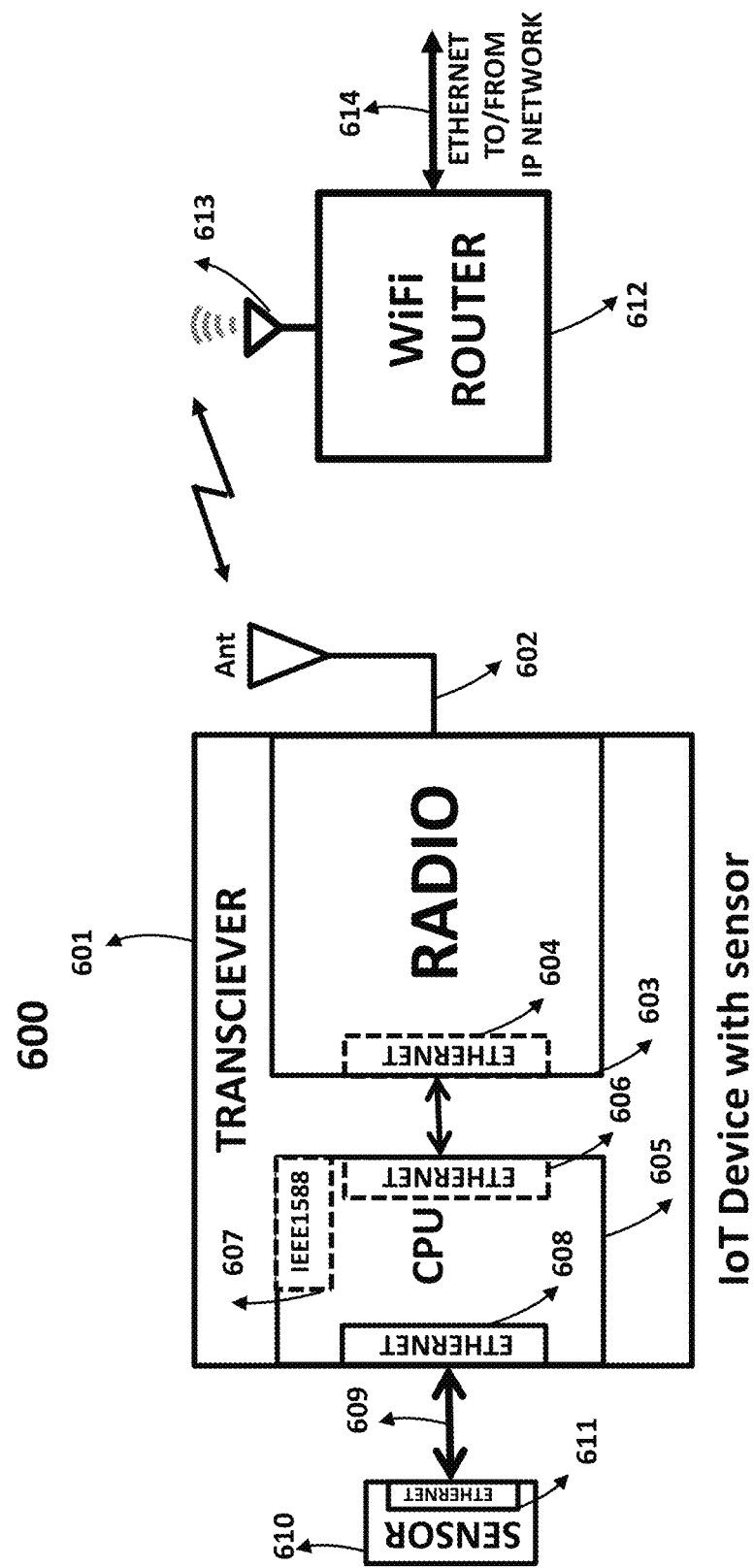
FIG. 6 illustrates a typical IoT device communicating with WiFi network

FIG. 6 illustrate a WiFi based IoT device 600. In general IoT device 600 communicates with WiFi (wireless fidelity) router 612 to exchange information data. IoT device 600 through radio 603 attaches itself to a WiFi router 612 in its surrounding environment that supports Internet of Things and listens to commands to activate sensor 610. Radio 603 when receives a command sends it to CPU 605 to be evaluated and performed by CPU 605 or sensor 610 (or any other device instead of sensor 610) that is connected to CPU 605. Then the results obtained from performing the commands through CPU 605 and radio 603 is transmitted to WiFi network for analysis.

In one embodiment, IoT device 600 uses IEEE1588 PTP to obtain time of day from WiFi router 612.

In another embodiment, IoT device 600 uses downlink transmit OFDM cyclic prefix, downlink transmit OFDM unused sub-carriers, or unused bits or messages in a downlink WiFi frame to obtain time of day.

In one embodiment, IoT device 600 receives an absolute time from WiFi router 612 for its various activities as well as scheduling the external devices connected to IoT device 600 for their activities.

Figure 7:
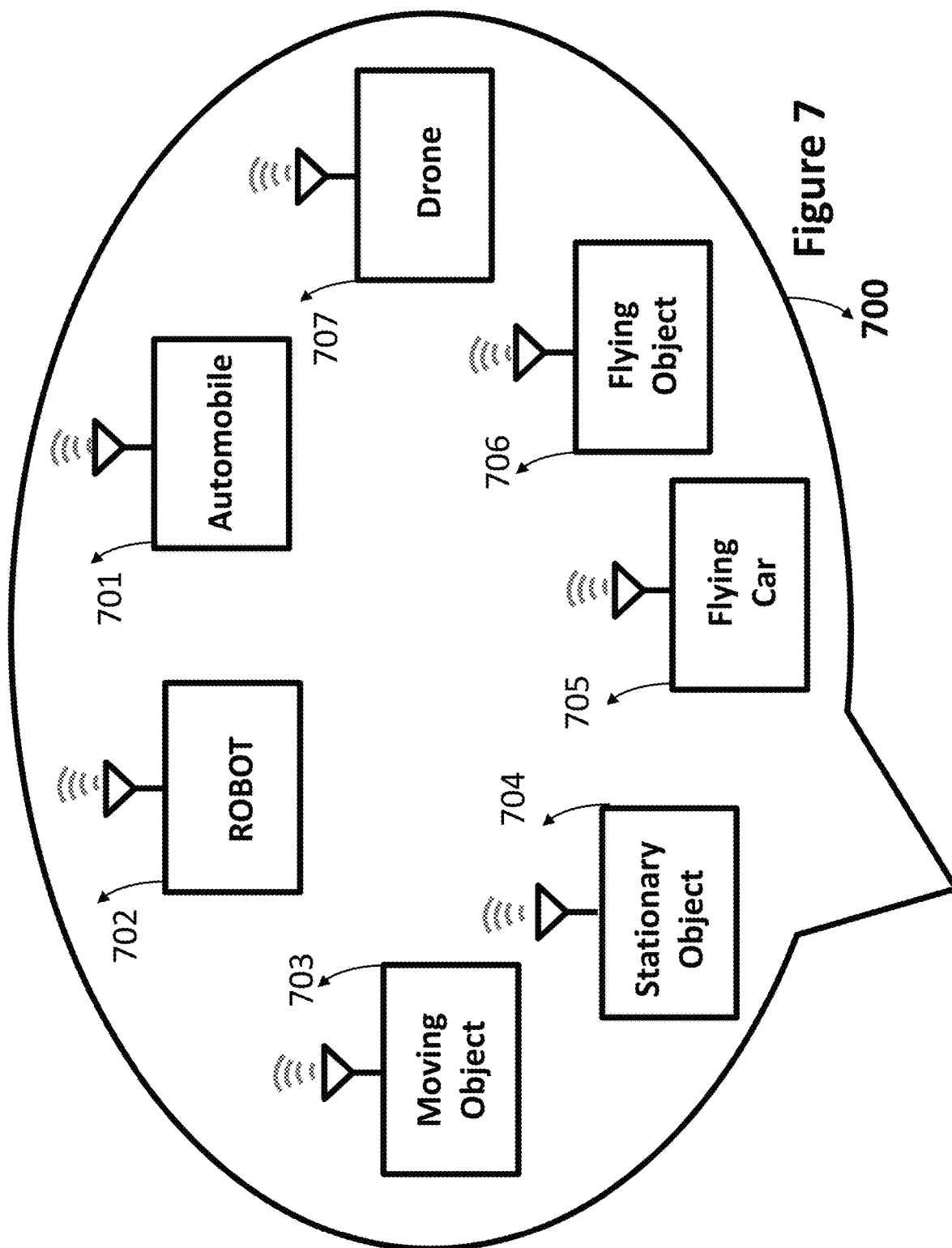
FIG. 7 shows moving vehicles, flying vehicles/objects, and stationary objects that act as an IoT in an environment

FIG. 7 depicts a smart environment 700. In general in the smart environment 700 in addition to open space various stationary, moving and flying object exist. In the smart environment or area 700 all the objects coexist and operate synchronously and freely without any interruption, interference, and collision.

Smart environment 700 includes, among other things, automobile 701, robots 702, moving objects 703, stationary objects 704, flying car 705, flying object 706, and drone 707.

In one embodiment, moving object 703 is human with body amour, bicycle, motorbike, boat and etc.

In one embodiment, stationary object 704 is a tree, a lamp post, a small cell, a building, a statue and etc.

In another embodiment of smart environment 700, flying object 706 is a helicopter, a small plane, a flying human, a flying robot, a glider, and etc.

In one embodiment of smart environment 700, automobile 701, robot 702, moving object 703, stationary object 704, flying car 705, flying object 706, and drone 707 act as IoT devices and broadcast wirelessly certain data specific to automobile, robot, moving object, stationary object, flying car, flying object, and drone.

In another embodiment of smart environment 700, the broadcast data includes a time stamp indicating time of day, method of obtaining the time of day (IEEE1588, cyclic prefix, GPS, or others), type of the object, location coordinates obtained from GPS (global positioning system) receiver, an identity number, signal propagation time through transmitter of the IoT device's transceiver up to the input of transmit antenna, and an estimated mass.

In one embodiment, the identity number of an object (IoT device) is its serial number.

In one embodiment, the identity number of an object (IoT device) is an IP (Internet Protocol) address.

In one embodiment, the identity number of an object (IoT device) is a MAC (media access control) address.

In another embodiment of smart environment 700, each object (IoT device) in the environment receives the broadcast data from other objects (IoT devices) and is fully aware of its surrounding environment.

In one embodiment of smart environment 700, each object (IoT device) in the environment uses a protocol that is known to all objects (IoT devices) for broadcasting its data.

In one embodiment of smart environment 700, the broadcast protocol is defined by a standard body like IEEE (Institute of electrical and electronic engineering), ITU (International Telecommunication Union), or cellular network (5G and beyond).

In another embodiment, the broadcast protocol includes frames with a synchronization pattern for the receiver of object's (IoT device's) transceiver to synchronize and detect the broadcast data.

In one embodiment, the payload in each broadcast frame which consists of an object's (IoT device's) information data is compressed to reduce time and bandwidth required for transmission of the frame.

In one embodiment, one or more synchronization pattern are stored in the object's (IoT device's) transceiver or obtained from other public or private networks.

In another embodiment, an object (IoT device) in the smart environment 700 uses the time stamp and transmitter propagation time up to transmit antenna received from another object (IoT device) in the smart environment 700, and receiver propagation time of its own transceiver up to its detector (where the time stamp is detected) to estimate free space traveling time of broadcast data carrying the time stamp as well as free space traveling time of the time stamp. Then the free space traveling time of time stamp is used to calculate the distance between the two objects (IoT devices). From two consecutive estimated distances of the two objects (IoT devices) their approaching speed towards each other can be estimated. Further more from change in speed, acceleration or deceleration is obtained which is used to estimate an impact force between two objects (IoT devices) using the mass of the two objects (IoT devices).

In one embodiment, an object (IoT device) in smart environment 700 broadcast a time stamp which indicates the time of day at its transmitter antenna port.

In another embodiment, an object (IoT device) in the smart environment 700 uses the time stamp indicating the time of day at the transmitter antenna port of another object (IoT device) in the smart environment 700, and receiver propagation time of its own transceiver up to its detector (where the time stamp is detected) and the time of day the time stamp (from the other object or IoT device) is detected to estimate free space traveling time of the time stamp between two objects (IoT devices). Then the distance between the two objects (IoT devices) is calculated from free space traveling time of the time stamp.

In another embodiment, an object (IoT device) in the smart environment 700 uses GPS location coordinates of other objects (IoT devices) received from their broadcast data to calculate the distance between itself and other objects (IoT devices).

In one embodiment, a stationary object (IoT device) in the smart environment has its GPS location coordinates manually program to it.

FIG. 8 depicts a smart environment 800 with objects (IoT devices) that communicate with a public or private network. In general, the smart environment 800 in addition to open space consists of various stationary, moving and flying objects (IoT devices) that are capable of wirelessly communicate with other objects (IoT devices) as well as a public or private communication network. In the smart environment 800 all the objects (IoT devices) coexist synchronously in time (time of day) and operate freely without any interruption, interference, and collision. All the objects (IoT devices) in smart environment 800 are registered with 4G, 5G, or 6G (7G) networks through their eNodeB or gNodeB base station 808. 4G, 5G or 6G (7G) networks broadcasts certain information data to all objects (IoT devices) in smart environment 800 that are registered with 4G, 5G, or 6G (7G) networks through their eNodeB or gNodeB. The broadcast information data is updated when an object (IoT device) exit (deregister with eNodeB or gNodeB of 4G, 5G, 6G, or 7G network) or enter (register with eNodeB or gNodeB of 4G, 5G, 6G, 7G network) the smart environment 800. The base station 808 can also be a wireless router of a WiFi network and all objects (IoT devices) in smart environment 800 register with WiFi network through wireless router 808 and receive broadcast information data from WiFi network.

In one embodiment smart environment 800 includes, among other things, automobile 801, robot 802, moving object 803, stationary object 804, flying car 805, flying object 806, drone 807, and a wireless base station 808 that supports a public (eNodeB, or gNodeB of 4G, 5G, or 6G network and wireless router of a WIFi network) or private communication network.

In one embodiment, the wireless base station 808 is a cellular (4G or 5G, beyond 5G and 6G) small cell, macro-cell, micro-cell or picocell.

In another embodiment, the wireless base station 808 is a WiFi wireless router that is connected to the IP network as well as cellular network (4G, 5G, beyond 5G and 6G).

In one embodiment, the wireless base station 808 is part of a private network that is connected to IP network as well as cellular network (4G, 5G and beyond 5G and 6G).

In one embodiment, wireless base station 808 is a 4G RRU, a 5G RU or a 6G RU.

In another embodiment, the wireless base station (4G, 5G, 6G, or 7G) communicates with the stationary, moving and flying objects in the smart environment 800 and obtains type, location (obtained from GPS receiver), identity number, signal propagation time through transmitter of the IoT device's wireless transceiver up to the input of transmit antenna, and estimated mass from objects 801, 802, 803, 804, 805, 806 and 807.

In one embodiment, wireless base station (4G, 5G, 6G, or 7G) 808 in the smart environment 800 broadcast the information obtained from each object 801, 802, 803, 804, 805, 806 and 807 to all objects (IoT devices) in smart environment 800.

In one embodiment, all moving and stationary objects 801, 802, 803, 804, 805, 806 and 807 continuously update the data they obtain from wireless base station 808 related to other objects in their surrounding smart environment 800.

In another embodiment, the identity number of each object in the smart environment 800 is the object's serial number, a MAC address or an IP address that is an IP4 or IP6.

In one embodiment, the wireless base station 808 uses GPS to obtain clock synchronization and time of day.

In another embodiment, all objects (IoT devices) in the smart environment 800 receive time of day and their location coordinates from GPS receiver.

In another embodiment, a stationary object (IoT device) in the smart environment has its location coordinates manually program to it or obtains from base station 808.

In one embodiment, the wireless base station (4G, 5G, 6G, or 7G) 808 in smart environment 800 supports IEEE1588 (Institute of electrical and electronic engineering synchronization standard 1588) PTP which provides clock synchronization and time of day for wireless base station 808 through any port in data communication network as well as 4G, 5G, 6G, 7G network.

In another embodiment, all moving and stationary objects (IoT devices) 801, 802, 803, 804, 805, 806 and 807 also supports IEEE1588 in order to obtain time of day.

In one embodiment, wireless base station (4G, 5G, 6G, 7G, or WiFi) 808 broadcasts to each moving and stationary objects (IoT devices) 801, 802, 803, 804, 805, 806 and 807 an absolute time when they can broadcast their information or communicate with other IoT devices.

In one embodiment, wireless base station (4G, 5G, 6G, 7G, or WiFi) 808 broadcasts to each moving and stationary objects (IoT devices) 801, 802, 803, 804, 805, 806 and 807 the absolute time when they can transmit and receive.

In one embodiment, the absolute times assigned by IoT network (4G, 5G, 6G, 7G, or WiFi) to various IoT devices is constant or dynamically changes depending on the time of day or load on the IoT network.

In another embodiment, IoT network (4G, 5G, 6G, 7G, or WiFi) assigns an absolute time and a time window for broadcasting and communication to each IoT device registered with the IoT network.

In one embodiment, the time window assigned to each IoT device by IoT network (4G, 5G, 6G, 7G, or WiFi) is constant and identical for all registered IoT devices with the IoT network, different for each IoT device, dynamically changed by the IoT network, or requested by IoT device.

In one embodiment, wireless base station (4G, 5G, 6G, 7G, or WiFi) 808 broadcasts to each moving and stationary objects (IoT devices) 801, 802, 803, 804, 805, 806 and 807 the absolute time when their sensors can collect data.

In one embodiment, wireless base station (4G, 5G, 6G, 7G, or WiFi) 808 broadcasts to each moving and stationary objects (IoT devices) 801, 802, 803, 804, 805, 806 and 807 the absolute time when their wireless sensors can perform wireless ranging to measure a distance and an approaching speed of various objects in their surrounding smart environment.

In one embodiment, wireless base station (4G, 5G, 6G, 7G, or WiFi) 808 broadcasts to each moving and stationary objects (IoT devices) 801, 802, 803, 804, 805, 806 and 807 the carrier frequency and modulation for their wireless sensor.

In one embodiment, wireless base station (4G, 5G, 6G, 7G, or WiFi) 808 broadcasts to each moving and stationary objects (IoT devices) 801, 802, 803, 804, 805, 806 and 807 the carrier frequency, channel, modulation, data rate, range of output power, and over the air protocol (type of transceiver which is one of 4G, 5G, 6G, 7G, WiFi, Bluetooth, Zigbee, or infrared) for broadcasting and communicating to other IoT devices.

In one embodiment, each moving and stationary objects (IoT devices) 801, 802, 803, 804, 805, 806 and 807 exchange Ethernet packets with wireless base station 808.

In one embodiment, each moving and stationary objects (IoT devices) 801, 802, 803, 804, 805, 806 and 807 exchange Ethernet packets among each other based on the absolute time assigned to them by the base station 808.

In one embodiment, the link between each moving and stationary objects (IoT devices) 801, 802, 803, 804, 805, 806 and 807 and wireless base station (4G, 5G, 6G, 7G, or WiFi) 808 is an over the air Ethernet link.

In one embodiment, communication link between each moving and stationary objects (IoT devices) 801, 802, 803, 804, 805, 806 and 807 and the cloud network, data network, and core network through wireless base station (4G, 5G, 6G, 7G, or WiFi) 808 supports a single end-to-end Ethernet packet protocol.

In another embodiment, moving and stationary objects (IoT devices) 801, 802, 803, 804, 805, 806 and 807 use their wireless sensor to broadcast their broadcast data.

In one embodiment, moving and stationary objects (IoT devices) 801, 802, 803, 804, 805, 806 and 807 use their wireless transceiver that communicates with 4G, 5G or 6G (7G) network to broadcast their broadcast data or Ethernet frame or packet.

In one embodiment, moving and stationary objects (IoT devices) 801, 802, 803, 804, 805, 806 and 807 support WiFi, Bluetooth, Zigbee, Infrared and proprietary wireless transceivers and use them to broadcast their broadcast data or transmit and receive Ethernet packets or frames.

Figure 9A:
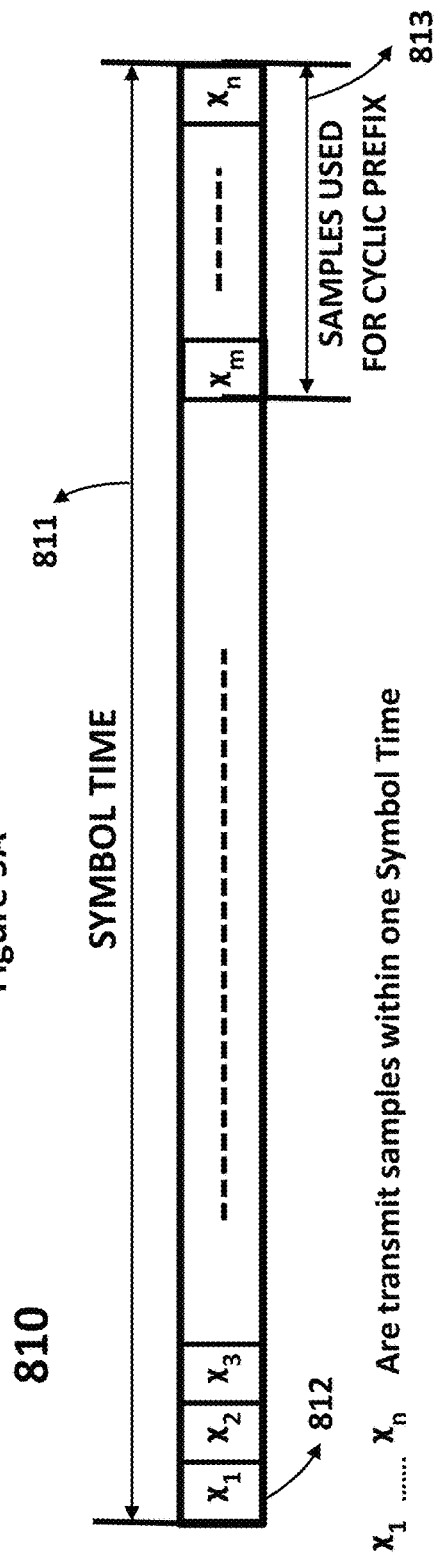

FIG. 9A depicts OFDM transmit symbol signal 850 before adding cyclic prefix. 4G, 5G and 6G (or 7G) use OFDM (orthogonal frequency division multiplexing) in their transmit path. The duration of transmit signal is one OFDM symbol 851 for 4G eNodeB and 5G (6G) gNodeB. The transmit signal 850 consists of "n" samples $x_1$ to $x_n$, 852. To eliminate inter-symbol interference "n-m" samples 853 from end of OFDM symbol are copied at the beginning of symbol or some samples from the beginning of OFDM symbol are copied at the end of symbol. The "m to n" samples are called cyclic prefix and the duration of it depends on radius of coverage of RRU and RU transmitters. These "m to n" samples at the receiver of user equipment UE (IoT device) are removed by using correlation before performing the receiver functions.

Figure 9B:
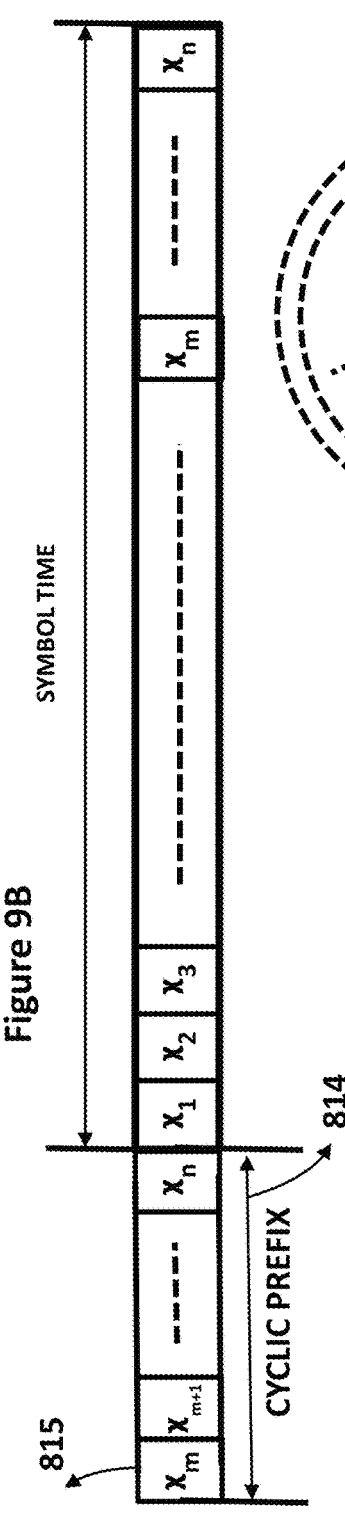

FIG. 9B shows transmit signal with cyclic prefix 854 that is added at the beginning of transmit symbol which consists of "n" samples $x_1$ to $x_n$ 852. Samples $x_m$ to $x_n$ from end of transmit symbol are copied at the beginning of "n" samples $x_1$ to $x_n$ as cyclic prefix 854. In the UE (IoT device) receiver cyclic prefix 854 is removed from received signal before the receive process starts. The process of removal of cyclic prefix is a circular correlation. The highest correlation is achieved when all samples in cyclic prefix are matched. There is always possible one or more samples in cyclic prefix are not matched due to various impairment and results in lower amount of correlation but still removal of cyclic prefix is possible. Therefore, it is possible to use one or more samples in cyclic prefix to transmit time of day to user equipment UE (IoT device).

In one embodiment of transmit signal 850 one or more samples of cyclic prefix 854 samples $x_m$ to $x_n$ is used to send the time of day to user equipment UEs or IoT devices.

In another embodiment the samples used from cyclic prefix 854 for transmitting time of day are at the start, middle, or end of cyclic prefix 854.

In another embodiment the samples used from cyclic prefix 854 for transmitting time of day are at any location in cyclic prefix 854 and the location do not change until all time of day data is transmitted.

In one embodiment the time of day is sent to user equipment UEs, or IoT devices over a number of transmit OFDM symbols.

In one embodiment the time of day includes date and time of day and date include year, month and day.

In one embodiment the bits in samples from cyclic prefix 854 are used for transmission of time of day to UEs or IoT devices.

In another embodiment the top bits in sample ($x_m$) 855 of cyclic prefix are used to send time of day in order to mitigate effect of any noise, interference or fading.

In one embodiment only one sample of cyclic prefix 854 is used for transmitting the time of day and the first sample that is used for time of day has a detectable bit pattern to indicate that next samples at the same location in next cyclic prefixes contain the time of day.

In one embodiment more than one sample of cyclic prefix 854 is used for transmitting the time of day and the first sample that is used for time of day has a detectable bit pattern to indicate that next samples whether in present cyclic prefix or next cyclic prefixes contain the time of day.

In another embodiment the first sample of first cyclic prefix carries the hour, the first sample of second cyclic prefix carries the seconds, the first sample of third cyclic prefix carries the milliseconds, the first sample of forth cyclic prefix caries the microseconds, the first sample of fifth cyclic prefix caries nanoseconds, and if more accuracies are available the first sample of sixth cyclic prefix carries the picoseconds.

In one embodiment the bits used to represent the time of day are compressed (using one of compression algorithms) in order to use less cyclic prefix samples for transmission of time of day.

There is a time difference between transmissions of two cyclic prefixes. During this time difference the date, hour ($T_h$), second ($T_s$), millisecond ($T_m$), microsecond ($T_\mu$), or nanosecond ($T_n$) of time of day can be incremented and this creates a significant time error between RU/RRU and UEs or IoT devices. Therefore, before sending time of day there is a need to find out if one of ($T_h$), ($T_s$), ($T_m$), ($T_\mu$), or nanosecond ($T_n$) will be incremented during the transmission of complete time of day.

In one embodiment the date, hour ($T_h$), second ($T_s$), millisecond ($T_m$), microsecond ($T_\mu$), or nanosecond ($T_n$) of time of day if needed is incremented before being sent to UE or IoT device.

In another embodiment, the time of day before being sent to UE or IoT device is adjusted for propagation time of IFFT through transmitter path of RU/RRU or BBU/DU up to antenna in order to reduce the time error between time of day at RU/RRU (or BBU/DU) and UEs or IoT devices.

In one embodiment the date and time of day that is sent to UE or IoT device is repeated or updated with a configurable time interval.

Figure 9C:
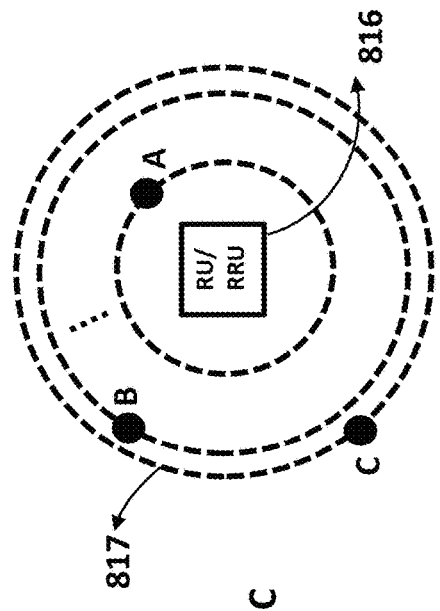

FIG. 9C depicts a typical coverage of RRU/RU in a 4G, 5G, 6G, or (7G) wireless network. UEs or IoT devices A, B, and C are at different distance from RU/RRU. Therefore, UEs or IoT devices A, B, and C receive time of day at different time which results in time error between UEs or IoT devices. These UEs or IoT devices when transmit to RU/RRU need to adjust their transmission time based on their time alignment or time advance which compensate for their difference in distance from RRU/RU. The time alignment or time advance is used to eliminate the error in time of day at UEs or IoT devices A, B, and C and make all UEs or IoT devices have the same time of day.

In one embodiment UEs or IoT devices that are at different distance from their common RRU/RU use their time alignment or time advance to adjust the time of day received from RRU/RU in order to have the same time of day.

In 4G, 5G, and 6G (or 7G) it is possible to use downlink methods similar to cyclic prefix to transmit time of day to UEs or IoT devices. These methods can utilize unused subcarriers or unused bits or messages in various downlink channels. For instance in 4G (as well as 5G and 6G) LTE there are two cell search procedures: one for initial synchronization and another for detecting neighbor cells in preparation for handover. In both cases the UE or IoT device uses two special signals broadcast on each RRU: Primary Synchronization Sequence (PSS) and Secondary Synchronization Sequence (SSS). The detection of these signals allows the UE or IoT device to complete time and frequency synchronization and to acquire useful system parameters such as cell identity, cyclic prefix length, and access mode (FDD/TDD).

In the frequency domain, the PSS and SSS occupy the central six resource blocks (RBs, 72 subcarriers), irrespective of the system channel bandwidth, which allows the UE or IoT device to synchronize to the network without a priori knowledge of the allocated bandwidth. The synchronization sequences use 62 sub-carriers in total, with 31 sub-carriers mapped on each side of the DC sub-carrier which is not used. This leaves 5 sub-carriers at each extremity of the 6 central RBs unused. These 10 unused sub-carriers can be used to transmit time of day to UEs or IoT devices. Similar to cyclic prefix the time of day should be adjusted for propagation time through transmitter path up to transmit antenna port in order to minimize time difference between gNodeB/eNodeB (RU/RRU) and UEs or IoT devices. During transmission of the time of day it is possible one of ($T_h$), ($T_s$), ($T_m$), ($T_\mu$), and ($T_n$) has to be incremented before being sent to UEs or IoT devices due to the time it takes to transmit the time of day.

In one embodiment unused downlink sub-carriers is used to transmit time of day to UEs or IoT devices.

It is also possible to utilize unused bits or messages in various downlink channels of 4G, 5G, or 6G (7G) to transmit the time of day similar to unused sub-carriers.

In another embodiment unused bits or messages of various downlink channels is used to transmit time of day to UEs or IoT devices.

In one embodiment when unused downlink sub-carriers, bits, or messages are used, due to the time takes to send all the data, the day, hour ($T_h$), second ($T_s$), millisecond ($T_m$), microsecond ($T_\mu$), or nanoseconds ($T_n$), of time of day if needed is incremented before being sent to UE or IoT device.

Figure 9D:
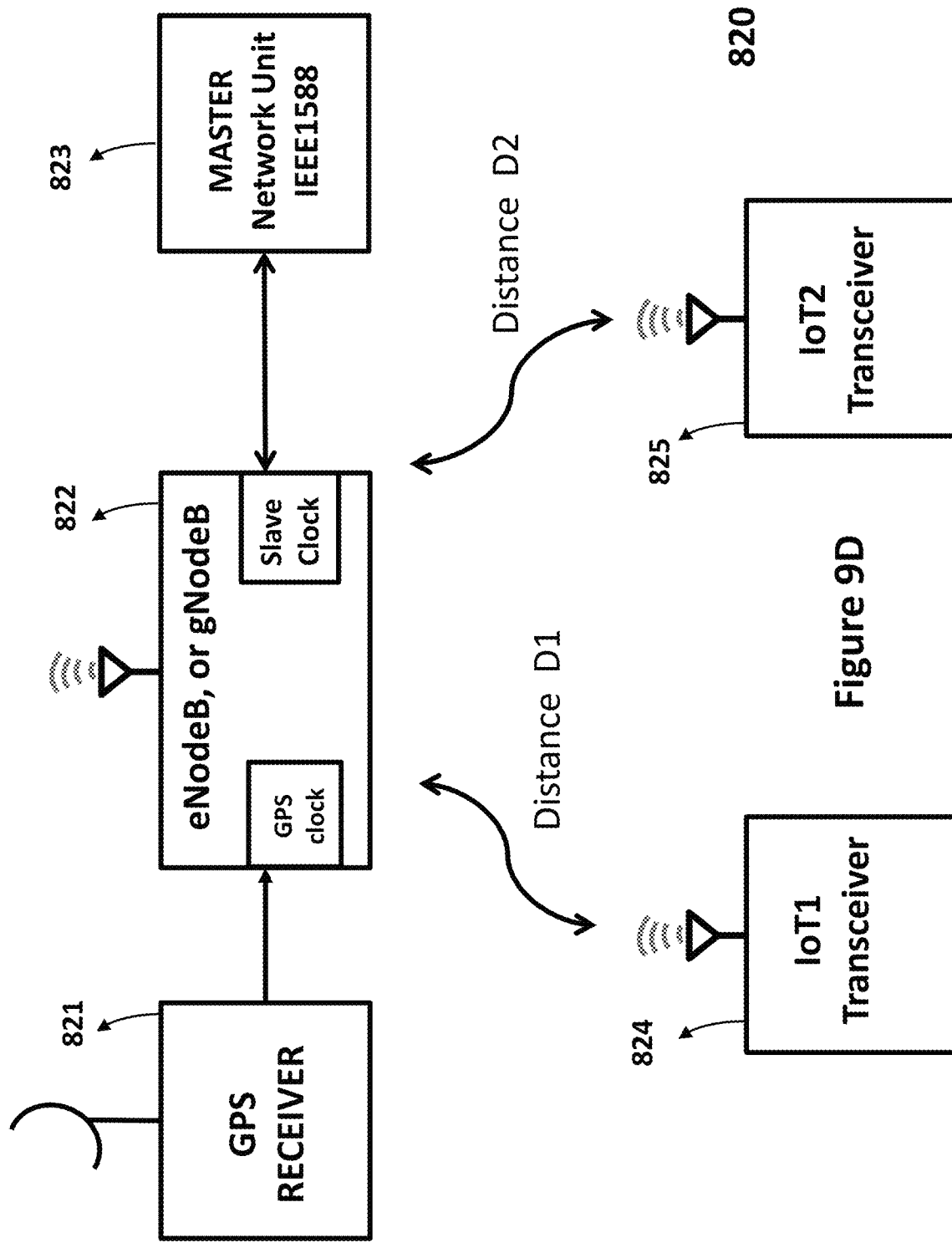

FIG. 9D shows method 820 of achieving clock synchronization and obtaining time of day for eNodeB or gNodeB. The eNodeB or gNodeB 822 uses two methods for clock synchronization and time of day. One method is to use GPS receiver 821 and another method is to act as a slave network and exchanges IEEE1588 PTP messages with a master network 823.

IoT1 device 824 and IoT2 device 825 with distance D1 and D2 from eNodeB or gNodeB 822 both frequency and phase synchronize with the eNodeB or gNodeB 822 using over the air protocol.

Figure 9E:
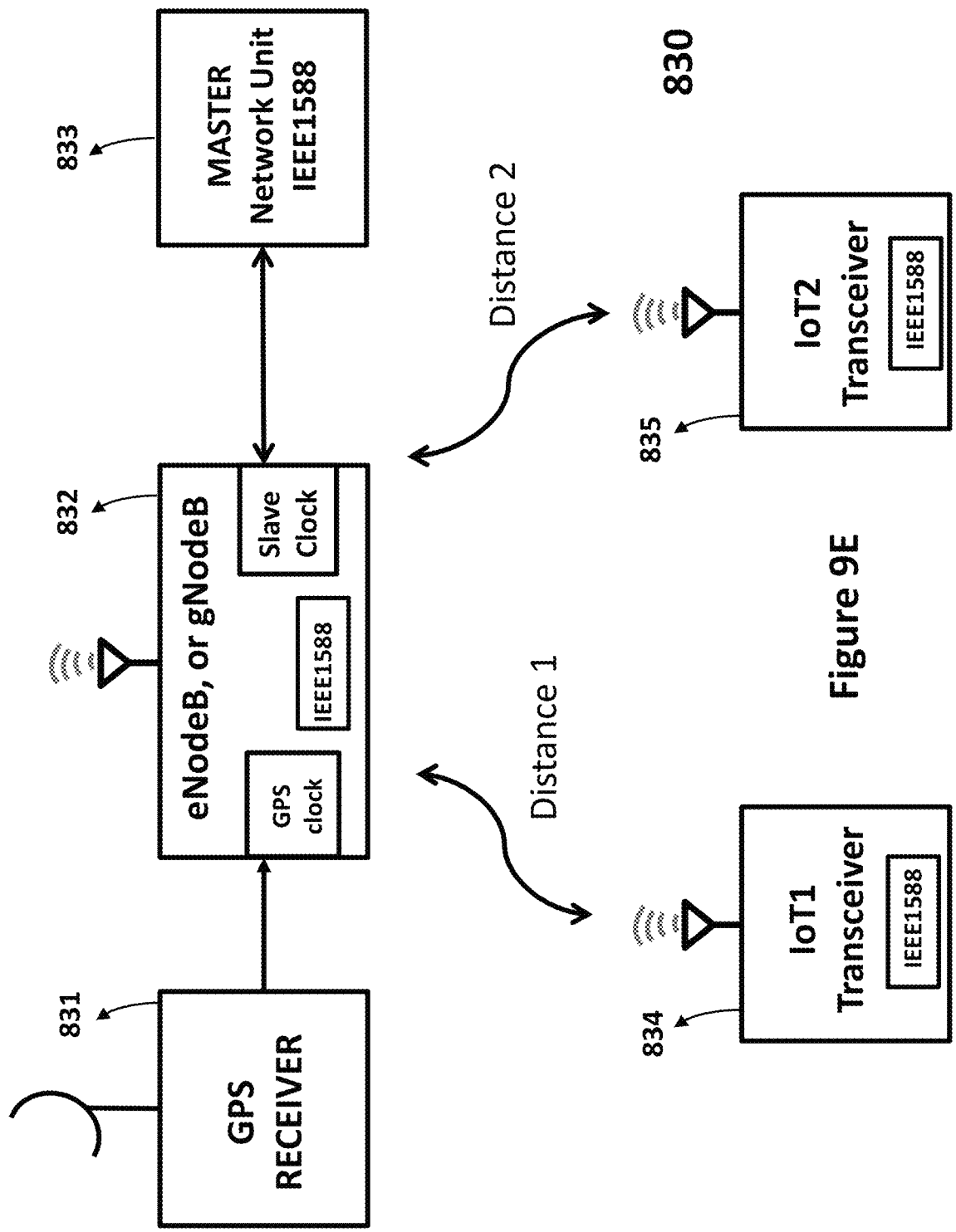

FIG. 9E shows method 830 where an IoT device uses IEEE1588 to obtain time of day. The eNodeB or gNodeB 832 uses either GPS receiver 831 or IEEE1588 PTP from a master network unit 833 to achieve clock synchronization and obtain time of day. IoT1 device 834 and IoT2 device 835 with distance D1 and D2 from RRU or RU 832 both frequency and phase synchronize with the eNodeB or gNodeB 832 using over the air protocol. To obtain time of day both IoT1 device 834 and IoT2 device 835 exchange IEEE1588 PTP messages with eNodeB or gNodeB 832.

Figure 9F:
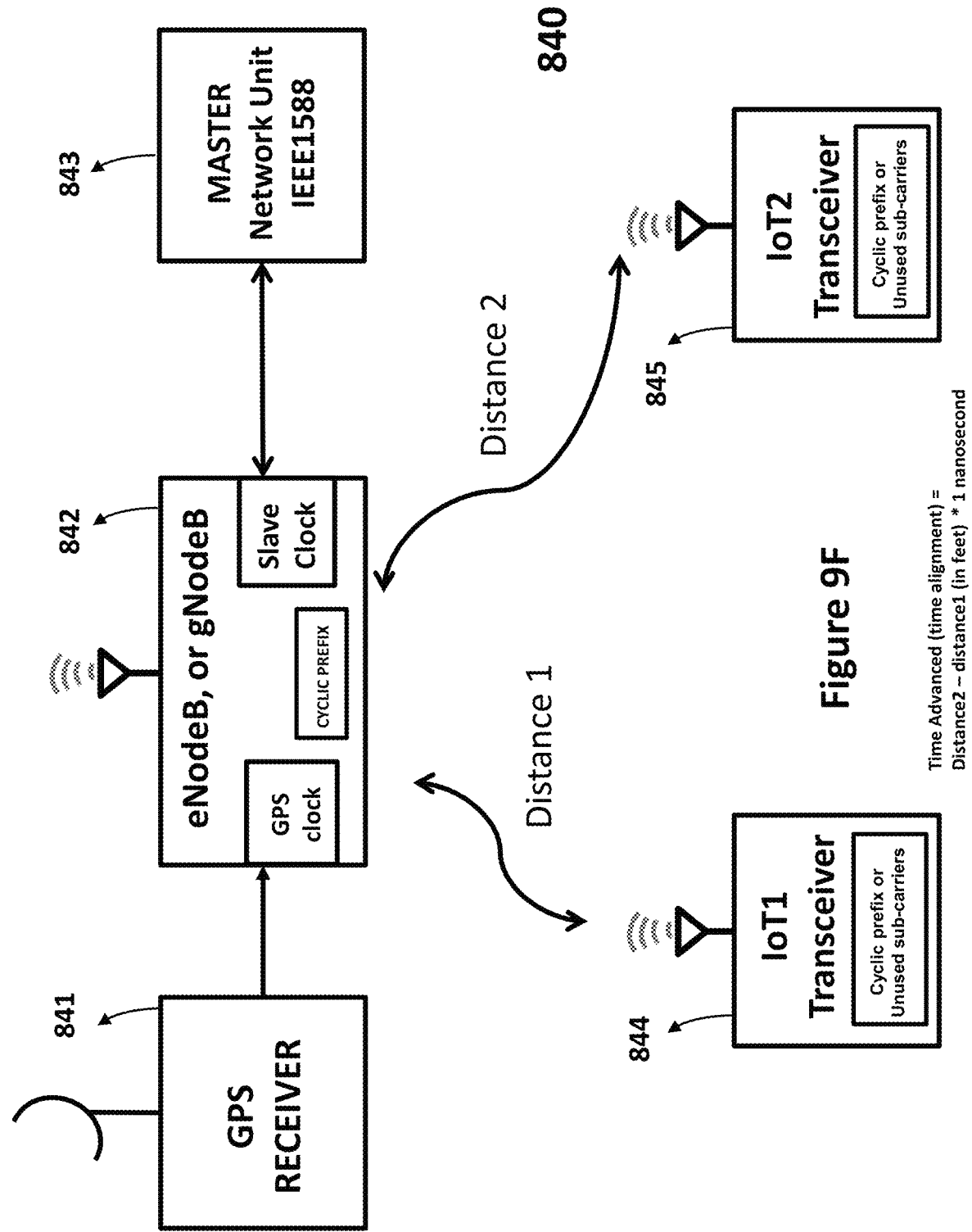

FIG. 9F illustrates method 840 where IoT device uses cyclic prefix or unused subcarriers to obtain time of day (TOD). The eNodeB or gNodeB 842 uses either GPS receiver 841 or IEEE1588 PTP from master network unit 843 to achieve clock synchronization and obtain time of day. IoT1 device 844 and IoT2 device 845 with distance D1 and D2 from eNodeB or gNodeB 842 both frequency and phase synchronize with the eNodeB or gNodeB 842 using over the air protocol. IoT1 device 844 and IoT2 device 845 receive TOD information through cyclic prefix, unused sub-carriers, unused bits or messages from eNodeB or gNodeB 842. Since IoT1 device and IoT2 device are at difference distances D1 and D2 from eNodeB or gNodeB 842 then time alignment or time advance is used to adjust time of day that IoT1 device and IoT2 device received from eNodeB or gNodeB 842. Time alignment or time advance for adjusting TOD may also consider the received signal propagation time between antenna port and decoder of IoT1 device or/and IoT2 device. IoT1 and IoT2 devices may also consider the transmit signal propagation time between modulator and antenna port and the propagation time from their antenna port to their detector.

FIG. 9G shows a scenario 850. In scenario 850 there are eNodeB1 or gNodeB1 851 and eNodeB2 or gNodeB2 852 and both use either GPS or IEEE1588 to achieve clock synchronization and obtain time of day. They both use cyclic prefix, unused sub-carriers, unused bits, unused messages or IEEE1588 PTP to propagate time of day to IoT devices that are registered with them. In the scenario 850 as shown in FIG. 9G IoT1 device 853 is attached to eNodeB1 or gNodeB1 851 and IoT2 device 854 is attached to eNodeB2 or gNodeB2 852. Since eNodeB1 or gNodeB1 851 and eNodeB2 or gNodeB2 852 obtain their time of day either from GPS or IEEE1588 PTP then both IoT device 853 and IoT2 device 854 should have the same time of day. If there is any difference between IoT1 device and IoT2 device that will be in order of a few nanosecond.

FIG. 10A depicts Ethernet frame 870 and broadcast frame 880.

In one embodiment the broadcast frame 880 uses similar structure as Ethernet frame 870.

In one embodiment the broadcast frame 880 sends the time of day in payload.

In one embodiment the broadcast frame 880 instead of sending destination address sends the time of day.

In another embodiment the source address (which is a media access control MAC address) of the broadcast frame 880 or an IP address is the identity code of a transceiver (IoT device, sensor, WiFi router, RRU, RU, private base station, or any other wireless device).

In one embodiment, two wireless devices (IoT devices, sensors, and others) use Ethernet packets or frame to exchange information between them when both source and destination addresses are used to identify the two wireless devices. One wireless device retrieves the address of another wireless device from its broadcast packet and then using Ethernet packets establishes direct communication between them to exchange information data.

Figure 10B:
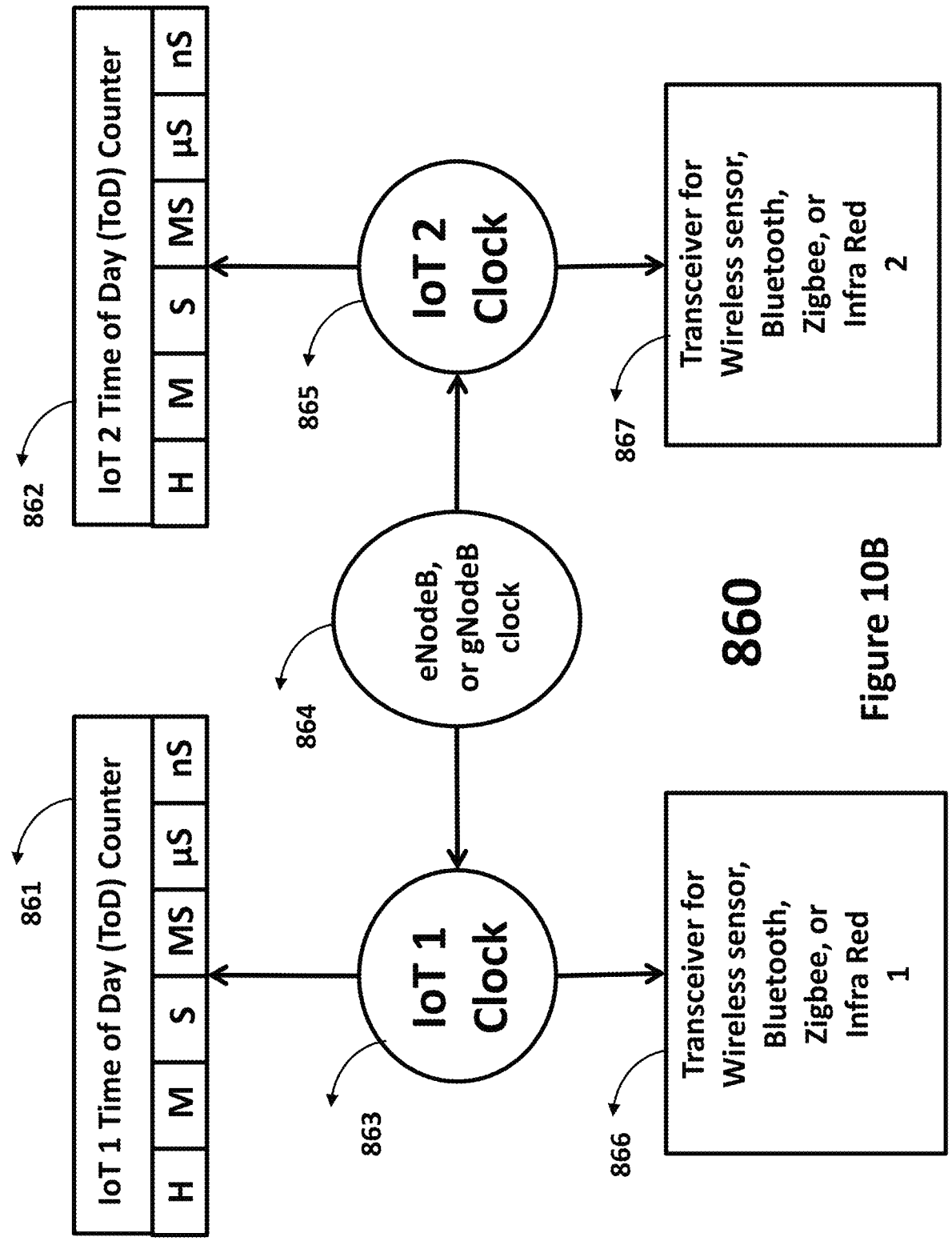

FIG. 10B shows two IoT devices 860. Both IoT1 device and IoT2 device have their clocks 863 and 865 frequency and phase synchronized with eNodeB or gNodeB clock 864. IoT1 and IoT2 devices 866 and 867 can support a wireless sensor transceiver, a Bluetooth transceiver, a Zigbee transceiver, an Infrared transceiver, and a 4G, 5G, 6G, or 7G transceiver. IoT1 and IoT2 devices 866 and 867 use 4G, 5G, 6G, or 7G transceivers to obtain clock frequency and phase synchronization from 4G, 5G, 6G, or 7G eNodeB or gNodeB 864.

IoT1 clock 863 increments time of day 861 for IoT1 device 866 and IoT2 clock 865 increments time of day 862 for IoT2 device 867. Both IoT devices 866 and 867 use eNodeB or gNodeB 864 to achieve clock frequency and phase synchronization as well as obtaining time of day 861 and 862. IoT1 866 and IoT2 867 should have their transmit frequency+/−0.1 part per million (PPM) accurate compared with the frequency they receive from eNodeB or gNodeB 864. Worst case scenario is when IoT1 866 transmit frequency is +0.1 PPM compared with received frequency and IoT2 867 transmit frequency is −0.1 PPM compared with received frequency from eNodeB or gNodeB 864. A difference of 0.2 PPM between IoT1 clock 863 and IoT2 clock 865 produce very negligible error when used for incrementing IoT1 time of day 861 and IoT2 time of day 862. In addition IoT1 clock 863 and IoT2 clock 865 as well as IoT1 time of day 861 and IoT2 time of day 862 are continuously updated which results to an error tremendously small and negligible.

Figure 10C:
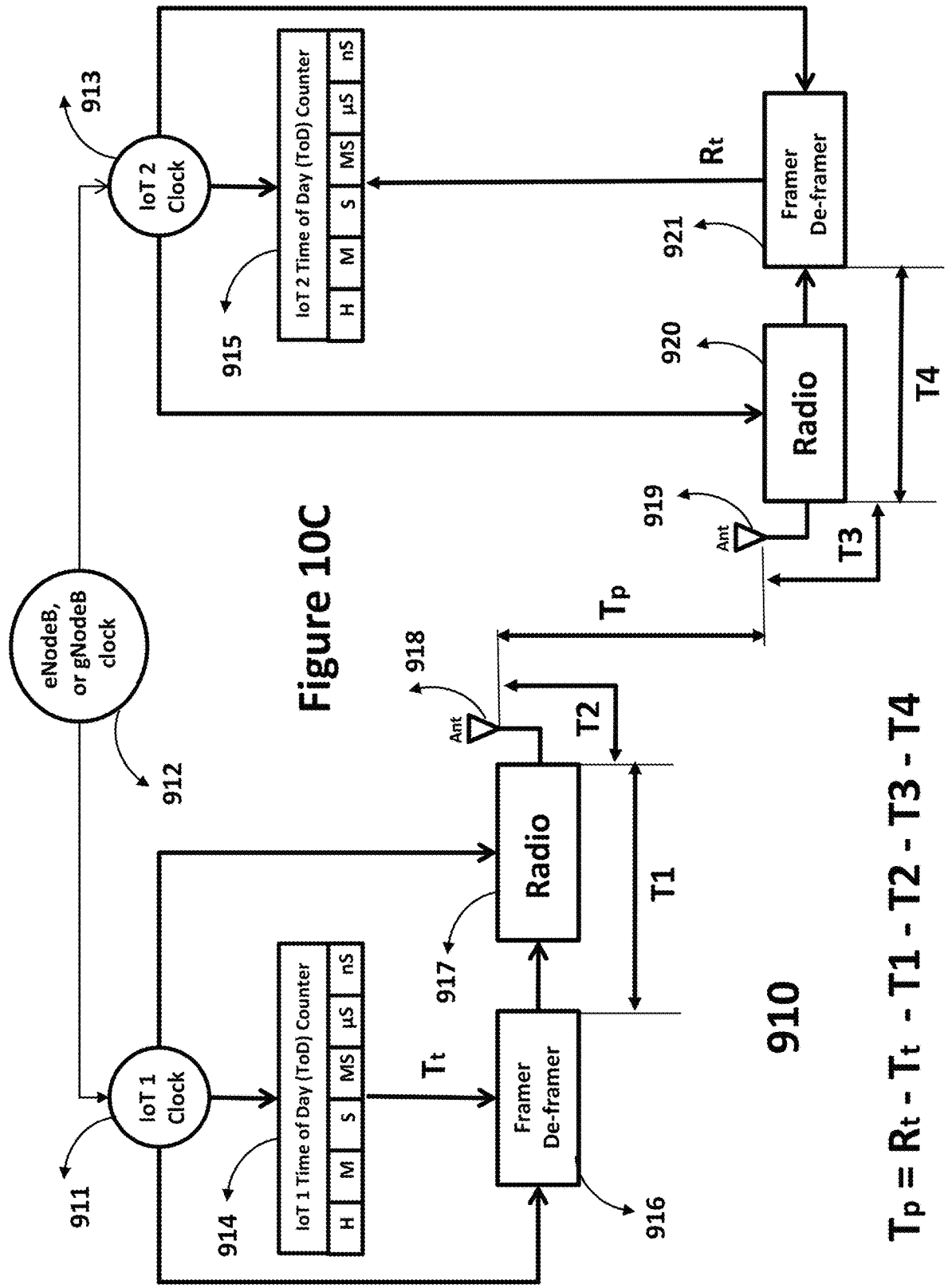

FIG. 10C shows solution 910 to estimate and calculate the distance between and approaching speed of IoT1 device and IoT2 device. IoT1 device comprises of IoT1 clock 911, IoT1 time of day (TOD) counter 914, IoT1 framer/de-framer 916, radio 917, and antenna 918. IoT2 device comprises of IoT2 clock 913, IoT2 time of day (TOD) counter 915, IoT2 framer/de-framer 921, radio 920, and antenna 919. Both IoT1 clock 911 and IoT2 clock 913 achieve frequency and phase synchronization through eNodeB or gNodeB 912 and obtain their time of day from eNodeB or gNodeB 912. The IoT devices also can obtain their time of day using GPS receiver. IoT1 device uses time of day (TOD) counter 914 to maintain TOD and is incremented by IoT1 clock 911. Similarly IoT2 device uses time of day (TOD) counter 915 to maintain TOD and is incremented by IoT2 clock 913.

IoT1 device uses framer/de-framer 916 to frame transmit broadcast packet signal or transmit Ethernet packet signal in order to transmit to other IoT devices through radio 917 and antenna 918. IoT2 device receives the broadcast or Ethernet packet signal from IoT1 device through antenna 919, radio 920 and framer/de-framer 921.

Similarly IoT2 device uses framer/de-framer 921 to frame transmit broadcast packet signal or transmit Ethernet packet signal in order to transmit to other IoT devices through radio 920 and antenna 919. IoT1 device receives the broadcast or Ethernet packet signal from IoT2 device through antenna 918, radio 917 and framer/de-framer 916.

Since both IoT1 device and IoT2 device use eNodeB or gNodeB 912 to achieve frequency and phase synchronizations as well as obtain time of day it can be assumed that both IoT1 and IoT2 devices have the same clock and time of day. Therefore, IoT1 clock 911 and IoT2 clock 913 have similar accuracy with negligible error and both IoT1 and IoT2 devices have identical time of day 914 and 915. It is also possible that the TOD of all IoT devices is not identical and there is error between the time of day (TOD) of a pair of IoT devices.

IoT1 device in its broadcast packet transmit time of day $T_t$ (time stamp) through framer 916, radio 917 and antenna 918. IoT2 device receives the broadcast packet from IoT1 device through its antenna 919, radio 920, and de-framer 921. IoT2 device record the receive time Rt of broadcasted $T_t$ by IoT1 device. Therefore, IoT2 device has two TODs, the broadcasted TOD $T_t$ (time stamp) by IoT1 device and received TOD Rt when the broadcast TOD was received. The difference between these two time ($Rt-T_t$) is the propagation time between IoT1 framer 916 and IoT2 de-framer 921 when the TOD of both IoT1 device and IoT2 device have negligible error or are identical.

Now if we subtract the propagation time through IoT1 radio T1, antenna T2, IoT2 antenna T3 and radio T4 we obtain propagation time Tp between antenna port of IoT1 and IoT2 devices. Both propagation time through IoT1 radio (T1), and antenna 918 (T2) are included in the payload of broadcast packet.

$$Tp=Rt-T_t-T1-T2-T3-T4$$

The distance between IoT1 device and IoT2 device is calculated using the propagation time Tp and using two consecutive Tp measurements the approaching speed between IoT1 device and IoT2 device can be calculated. Transmit TOD $T_t$ by IoT1 device can be adjusted to include propagation time through radio 917 (T1) and propagation time from radio 917 to output port of antenna 918 (T2). Therefore, transmit TOD inserted in broadcast frame is the TOD at output port of antenna 918. TOD also includes the time takes to insert it in the broadcast frame and any time taken for the broadcast frame to reach the radio 917. All the times are calculated by clock cycles so that TOD at the TOD counter and TOD leaving the antenna are the same. The same applies to IoT2 device and all other IoT devices in the smart environment.

Received TOD Rt by IoT2 device can also be adjusted to include propagation times (T3 and T4) through antenna 919 input port to radio 920 and radio 920. Therefore, received TOD retrieved from broadcast frame is TOD when ($T_t$) arrives at the input port of antenna 919. TOD also includes the time takes to retrieve it from the broadcast frame. The same applies to IoT1 device and all other IoT devices in the smart environment. In this case:

$$Tp=Rt-T_t$$

If the time of day at all IoT devices in the smart environment is identical within less than 10 nanosecond then any IoT device in the smart environment knows the distance of other IoT device with less than 10 feet error by receiving broadcast frames or packets from other IoT devices.

If the time of day at IoT devices in the smart environment are in error more than 10 nanoseconds then a two way communication is required.

FIG. 10D shows protocol 930 to estimate and calculate distance between IoT1 device (object) 931 and IoT2 device (object) 932. IoT1 device 931 sends a broadcast packet that contains the time of day t1 at the antenna port of IoT1 device 931. IoT2 device 932 receives the broadcast packet from IoT1 device 931, retrieves t1 from payload and records time of day t2 when t1 arrived at the antenna port of IoT2 device 932. IoT2 device 932 also retrieves the address of the IoT1 device from broadcast packet (frame).

Next IoT2 device 932 sends an Ethernet packet (frame) that contains in its payload the time of day t3 at the antenna port of IoT2 device 932, t1, and t2 to IoT1 device 931 using its address. IoT1 device 931 receives the Ethernet packet (frame) from IoT2 device 932, retrieves t3, t2, t1 and records time of day t4 when t3 arrived at the antenna port of IoT1 device 931. Then IoT1 device uses IoT2 device address and sends an Ethernet packet that contains in its payload t4, t3, t2, and t1 to IoT2 device. IoT2 device receives the Ethernet packet and retrieves t4. At this point IoT1 device 931 and IoT2 device 932 have 4 times t1, t2, t3 and t4 to calculate the distance between IoT1 device 931 and IoT2 device 932.

Protocol 930 is used when IoT1 device 931 and IoT2 device 932 do not have frequencies and time of day that are 100% identical or with very negligible error. Using t1, t2, t3 and t4 the propagation time between antenna port of IoT1 device 931 and antenna port of IoT2 device 932 is $$\text{Propagation time}=(t2-t1+t4-t3)/2$$

Then propagation time is used by IoT1 device 931 and IoT2 device 932 to find distance between IoT1 device 931 and IoT2 device 932 and then two consecutive distance measurements at two specific times is used to calculate approaching speed between IoT1 device 931 and IoT2 device 932.

Figure 10E:
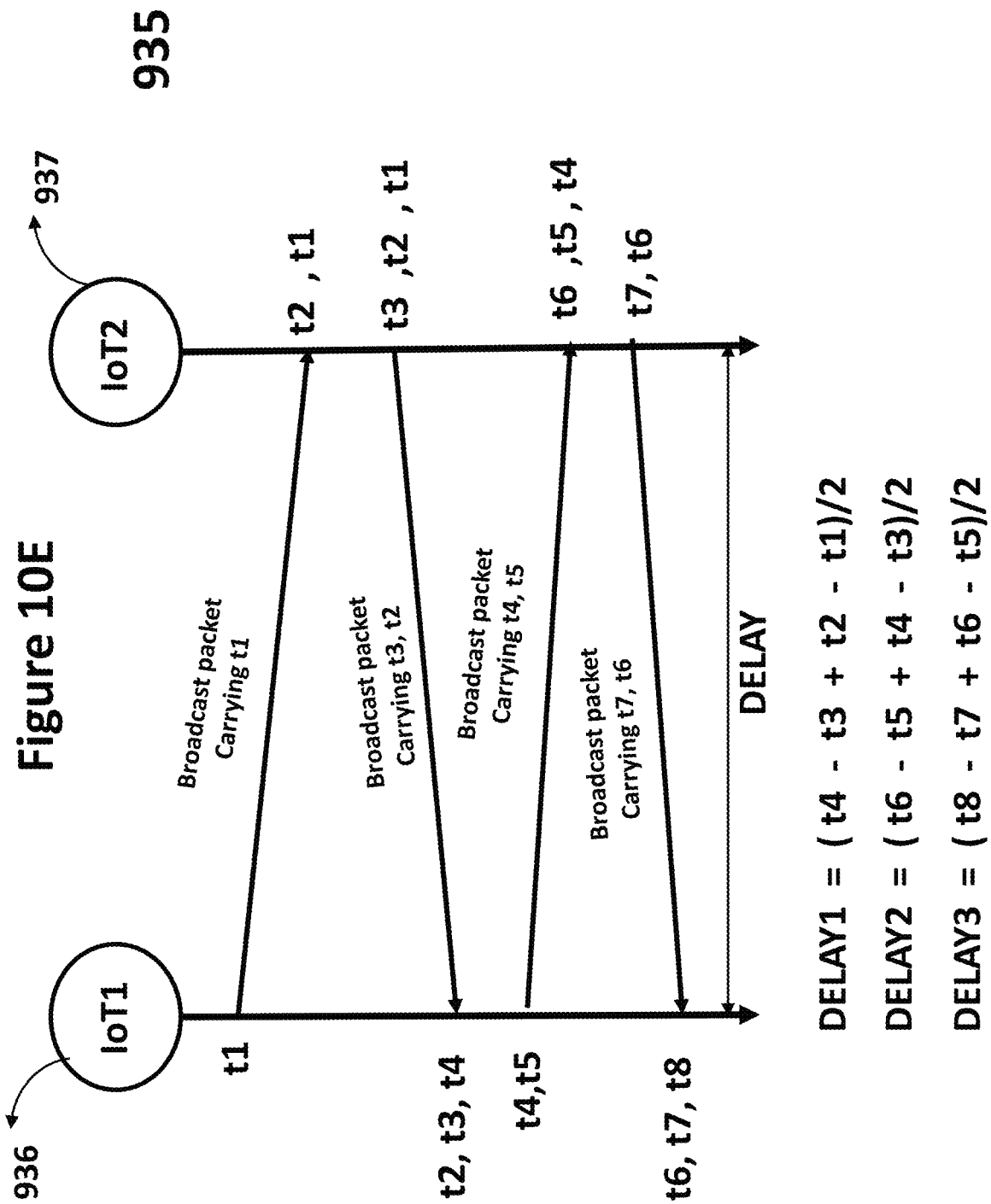

FIG. 10E shows protocol 935 to estimate and calculate distance between IoT1 device (object) 936 and IoT2 device (object) 937. IoT1 device 936 sends a broadcast packet to all IoT devices (objects) in its surrounding environment that contains in its payload the time of day t1 at the antenna port of IoT1 device 936. IoT1 device 936 in its payload also sends the TODs received at its antenna port broadcasted by other IoT devices in its surrounding environment. Therefore, IoT1 device 936 in its broadcast packet payload has a table with three columns. First column contains the address of other IoT devices in its surrounding environment that IoT1 device 936 received their broadcast packet. The second column is the latest TODs received by IoT1 device 936 in payload of broadcast frame or packet from other IoT devices in its surrounding environment. The third column is the time of day the latest TODs from other IoT devices arrived at the antenna port of IoT1 device 936.

Therefore, IoT1 device in its broadcast packet payload transmit three TODs. First TOD is time of the day at its antenna port. Second is time of day a latest TOD from another IoT device received at its antenna port. Third TOD is the latest TOD received in payload of other IoT devices in its surrounding environment.

Let's apply protocol 935 to IoT1 device (object) 936 and IoT2 device (object) 937. IoT1 device 936 sends a broadcast packet and in its payload includes TOD t1 at its antenna port with no record of IoT2 device 937. It is possible IoT1 device 936 has TOD records of other IoT devices in its payload table. IoT2 device 937 receives the broadcast packet from IoT1 device 936, retrieve t1 and records time of day t2 when t1 arrived at the antenna port of IoT2 device 937. IoT2 device 937 also retrieves the address of the IoT1 device 936 from its broadcast packet.

Next IoT2 device 937 sends a broadcast packet that contains the time of day t3 at the antenna port of IoT2 device 937 and next to the address of IoT1 device 936 t2 and t1 in second and third column of its payload table. IoT1 device 936 receives the broadcast packet from IoT2 device 937, retrieves t3, t2 and t1 and records time of day t4 when t3 arrived at the antenna port of IoT1 device 936. Then IoT1 device 936 sends a broadcast packet that contains TOD t5 at its antenna port and t4, and t3 next to address of IoT2 device 937 in second and third column of its payload table. IoT2 device 937 receives the broadcast packet and retrieves t4 as well as recording TOD t6 at its antenna port when t5 arrived. At this point IoT1 device 936 and IoT2 device 937 have 4 times t1, t2, t3 and t4 to calculate the distance between IoT1 device 936 and IoT2 device 937.

Protocol 935 is used when IoT1 device 936 and IoT2 device 937 do not have frequencies and time of day that are 100% identical or with very negligible error. Using t1, t2, t3 and t4 the propagation time between antenna port of IoT1 device 936 and antenna port of IoT2 device 937 is $$\text{Propagation time} = (t2-t1+t4-t3)/2$$

Then propagation time is used by IoT1 device 936 and IoT2 device 937 to find distance between IoT1 device 936 and IoT2 device 937 and then two consecutive distance measurements at two specific times is used to calculate approaching speed between IoT1 device 936 and IoT2 device 937. As shown in FIG. 10E DELAY1 is used for one distant measurement and DELAY2 is used for a second distant measurement.

Figure 10F:
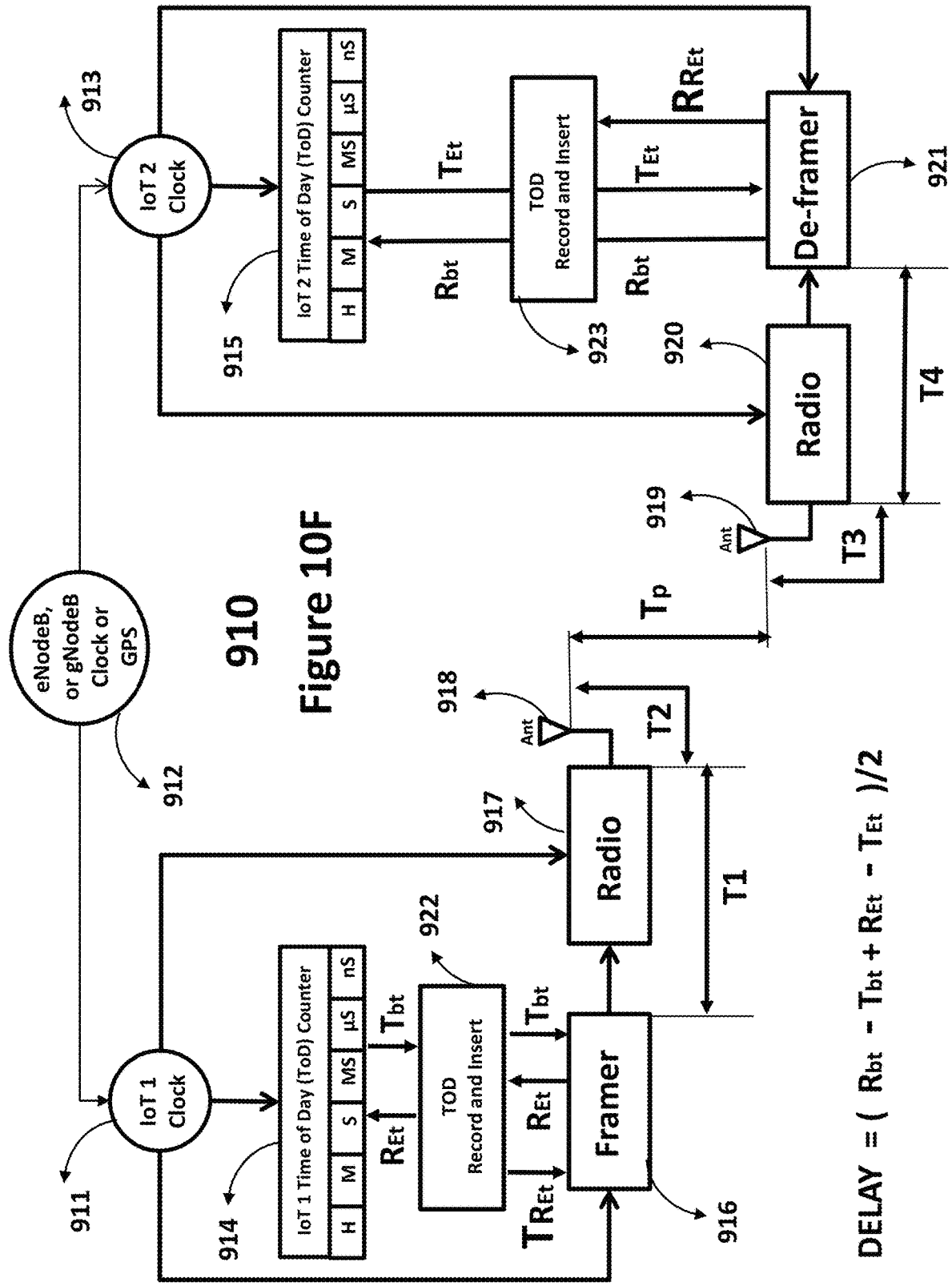

FIG. 10F shows implementation of protocol 930. IoT1 device sends broadcast TOD ($T_{bt}$) in a broadcast packet. Broadcast TOD ($T_{bt}$) can be either adjusted for delays T1 from TOD insertion into the framer to the output of the radio 917 and T2 from output of radio 917 to the input of antenna 918 by record and insert block 922 or T1 and T2 are included in broadcast packet payload. IoT2 device receives the broadcast packet from IoT1 device through antenna 919, radio 920 and framer/de-framer 921 and retrieves $T_{bt}$ and record time of day $R_{bt}$ when $T_{bt}$ is arrived and retrieved. $R_{bt}$ can be adjusted for T3 and T4 delays from output of antenna 919 to input of radio 920 and from input of radio 920 to the time it is extracted from de-framer 921 by record and insert block 923.

In next step IoT2 device sends an Ethernet packet to IoT1 device using IoT1 device address retrieved from its broadcast packet and includes an Ethernet time of day $T_{Et}$ in its payload. Ethernet time of day $T_{Et}$ can be adjusted for delays (T1 and T2 of IoT2 device) from radio 920 and antenna 919 by record and insert block 923 or delays (T1 and T2 of IoT2 device) are included in Ethernet packet payload. IoT1 device receives the Ethernet packet from IoT2 device through antenna 918, radio 917 and framer/de-framer 916 and retrieves $T_{Et}$ and record time of day $R_{Et}$ when $T_{Et}$ is arrived and retrieved. $R_{Et}$ can be adjusted for delays (T3 and T4 of IoT1 device) through antenna 918 and radio 917 by record and insert block 922.

Next IoT1 device sends time of day $R_{Et}$ when it received $T_{Et}$ from IoT2 device by an Ethernet packet to IoT2 device using its address. IoT2 device receives $R_{Et}$ and then uses $T_{bt}$, $R_{bt}$, $T_{Et}$ and $R_{Et}$ to calculate the propagation time between IoT1 device and IoT2 device by following equation.

$$\text{Propagation time between IoT1 and IoT2} = (R_{bt}-T_{bt}+R_{Et}-T_{Et})/2$$

When all times are adjusted for transmitter and receiver delays explained above. When T1, T2, T3, and T4 are not included then following equation is used.

$$\text{Propagation time between IoT1 and IoT2} = (R_{bt}-T_{bt}+R_{Et}-T_{Et})/2-(T1+T2 \text{ of IoT1})/2-(T1+T2 \text{ of IoT2})/2-(T3+T4 \text{ of IoT2})/2-(T3+T4 \text{ of IoT1})/2$$

Propagation time results in distance between IoT1 device and IoT2 device and two consecutive distance calculation results in the speed IoT1 device and IoT2 device approach each other.

Figure 11:
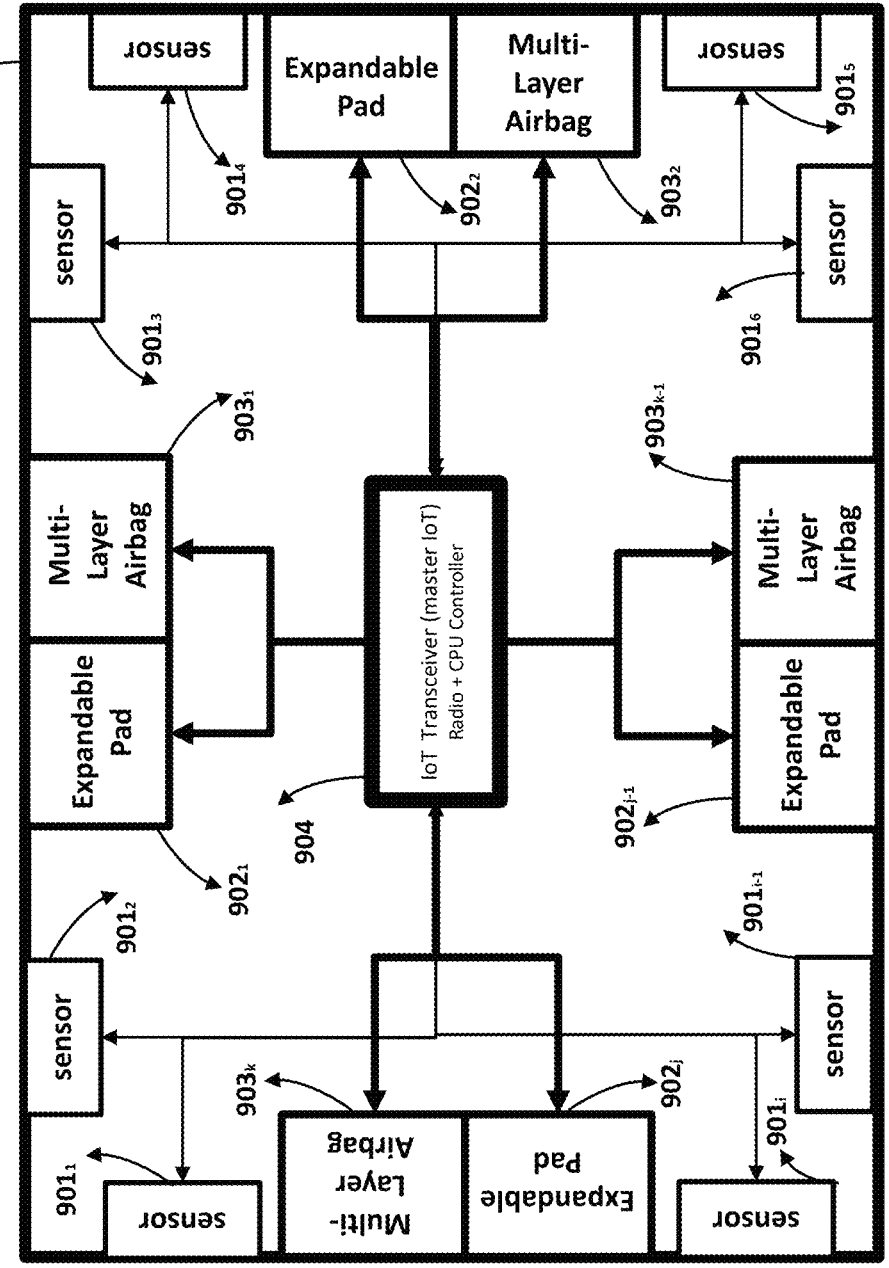
FIG. 11 depicts an IoT protection system for moving and stationary objects

FIG. 11 illustrates an embodiment of a navigation and protection system (NPS) for vehicle/object (IoT device) 900. In general, the NPS for vehicle/object (IoT device) 900 performs navigation and provides external body protection by applying voltage to two ends of an expandable pad and/or inflating a multilayer airbag. The NPS through its IoT transceiver (master IoT device) 904 registers with an IoT network and exchanges an operation information data (OID) related to NPS's operation and its status. NPS for vehicle/object (IoT device) 900 uses the OID from IoT network and detected information data (DID) from various sensors (including slave IoT devices) 901₁ to 901ᵢ to detect any malfunction of the vehicle/object (IoT device) 900 or approaching of any external objects that results in an impact. When NPS detects a potential impact based on its artificial intelligence analyses of the DID received from sensors (wireless sensor, internal sensors, internal devices, and slave IoT devices) 901₁ to 901ᵢ, broadcasts its problem to the IoT network and activates one or more of the expandable pads 902₁ to 902ⱼ or/and one or more of the multilayer airbag 903₁ to 903ₖ to minimize the damage to the vehicle/object (IoT device) 900 due to impact. NPS also uses the received DID to navigate the vehicle/object (IoT device) 900 when no imminent impact is detected.

NPS for vehicle/object (IoT device) 900 includes, among other things, sensors 901₁ to 901ᵢ (including wireless sensors and slave IoT devices), IoT transceiver (master IoT device) 904, expandable pads 902₁ to 902ⱼ, and multilayer airbags 903₁ to 903ₖ.

In one embodiment the NPS acts as a standalone IoT device used by various objects.

In one embodiment the NPS obtains time of day (TOD) and calendar date directly or through the vehicle/object (IoT device) 900 that uses the NPS.

In another embodiment the NPS uses time of day to define a time for the operation of various sensors (including wireless sensors, and slave IoT devices) 901₁ to 901ᵢ.

In one embodiment the sensors 901₁ to 901ᵢ are slave IoT devices to master IoT device 904 or wireless sensors.

In one embodiment, the vehicle/object (IoT device) 900 is a moving object, stationary object, or flying object.

In one embodiment of the NPS for vehicle/object (IoT device) 900, multiple expandable pads 902₁ to 902ⱼ and multiple multilayer airbags 903₁ to 903ₖ are mounted on all external sides of vehicle/object (IoT device) 900 to provide protection for impacts due to external objects at any external side of vehicle/object (IoT device) 900.

In one embodiment of the NPS for vehicle/object (IoT device) 900, the expandable pads $902_1$ to $902_j$ and multilayer airbags $903_1$ to $903_k$ are mounted on the main body frame of the vehicle/object (IoT device) 900 to provide a firm and strong support.

In another embodiment of the NPS for vehicle/object (IoT device) 900, by activating expandable pads $902_1$ to $902_j$ and/or multilayer airbags $903_1$ to $903_k$ the impact force to vehicle/object (IoT device) 900 will be lowered due to absorption or diffraction and provides more protection to the passengers of vehicle/object (IoT device) 900.

In one embodiment of the NPS for vehicle/object (IoT device) 900, one or more of the multilayer airbags $903_1$ to $903_k$ at one or multiple sides of the vehicle/object (IoT device) 900 is inflated to protect the external of vehicle/object (IoT device) 900 from fall, crash or impact with an external object.

In one embodiment of the NPS for vehicle/object (IoT device) 900, one or more of the expandable pads $902_1$ to $902_j$ at one or multiple sides of the vehicle/object (IoT device) 900 is activated by applying voltage to two ends of expandable pad to protect the external of vehicle/object (IoT device) 900 from fall, crash or impact with an external object.

In one embodiment of the NPS for vehicle/object (IoT device) 900, IoT transceiver (master IoT device) 904 resets, and configures itself based on configuration data stored in its memory and then starts to execute artificial intelligence executable software which controls all aspects of navigation and protection of the vehicle/object (IoT device) 900 using the DID provided by all monitoring devices or/and sensors (including wireless sensors or slave IoT devices) $901_1$ to $901_i$.

In one embodiment of the NPS for vehicle/object (IoT device) 900, multiple monitoring devices or sensors (wireless sensors, or slave IoT devices) $901_1$ to $901_i$ are distributed at various locations internal and external to vehicle/object (IoT device) 900 and each has a unique IP address (or MAC address) which is used to communicate with the IoT transceiver (master IoT device) 904 to avoid collision or confusion of the information data received by the controller CPU of the IoT transceiver (master IoT device) 904 from the sensors internal or external to the vehicle/object (IoT device) 900.

In one embodiment of the NPS for vehicle/object (IoT device) 900, the monitoring devices or sensors (wireless sensors, or slave IoT devices) $901_1$ to $901_i$ can be at least one of an image sensor, a wireless sensor, a radar, a heat sensor, a speed sensor, an acceleration sensor, a ultrasonic sensor, a proximity sensor, a pressure sensor, a G (gravity) sensor, an IR (infrared) sensor and others.

In one embodiment of the NPS for vehicle/object (IoT device) 900, a wireless sensor (slave IoT device) transmits (records completion of transmission at input of transmit antenna port) a coded signal similar to a unique identity code signal or a unique IP address signal and receives (record the completion of reception at receive antenna port) a reflected signal of the unique identity code signal, or the unique IP address signal from objects in surrounding environment of the vehicle/object (IoT device) 900 to avoid collision.

In another embodiment of the NPS for vehicle/object (IoT device) 900, the wireless sensor (salve IoT device) uses the time of completion of transmission of the unique identity code signal or the unique IP address signal at its transmit antenna port and the time of completion of the reception of the reflected signal of the unique identity code signal or the unique IP address signal at its receive antenna port to estimate free space traveling time of the unique identity code signal or the unique IP address signal to calculate a distance and an approaching speed of an object in the surrounding environment of the vehicle/object (IoT device) 900.

In one embodiment of the NPS for vehicle/object (IoT device) 900, the wireless sensor (slave IoT device) uses a time stamp (time of day) received from wireless sensor (slave IoT device) of NPS that belongs to another vehicle/object (IoT device) to estimate the distance between the two vehicles/objects (IoT devices).

In one embodiment of the NPS for vehicle/object (IoT device) 900, the wireless sensor (slave IoT device) uses time of day (time stamp) of a broadcast packet at the antenna port of transmitter of the wireless sensor (slave IoT device) of a NPS that belongs to another vehicle/object (IoT device) and the time of day its own receiver receives the broadcast packet (time stamp) at its receiver antenna port to estimate the free space traveling time of the time stamp in the broadcast data. Then the free space traveling time is used to calculate the distance between the two vehicles/objects (IoT devices).

In another embodiment, the wireless sensor (slave IoT device) uses one IP (MAC) address to communicate with IoT transceiver (master IoT device) 904 and a second IP address for transmitting a unique IP address signal over the air to monitor objects in surrounding environment.

In another embodiment, the wireless sensor (slave IoT device) uses a single IP4 or IP6 address for both communicating with IoT transceiver (master IoT device) 904 and transmitting a signal over the air.

In one embodiment of the NPS for vehicle/object (IoT device) 900, IoT transceiver (master IoT device) 904 communicates with at least one of a cellular network (4G, 5G and beyond, 6G), a WiFi network, and a private network to provide its own information data to the network and obtain an information data about other objects in its surrounding environment.

In one embodiment of the NPS for vehicle/object (IoT device) 900, the IoT transceiver (master IoT device) 904 supports IEEE1588 to obtain time of day (TOD) from at least one of a cellular base station (4G, 5G and beyond, 6G), a WiFi network, and a private network.

In one embodiment of the NPS for vehicle/object (IoT device) 900, in order to avoid collision, at least one of a cellular base station (4G, 5G and beyond, 6G), a WiFi router, and a private network broadcasts to vehicle/object (IoT device) 900 a channel, a frequency, a modulation, and an absolute time with a time slot duration when its wireless sensors (slave IoT devices) can transmit the unique IP address signal and receive the reflected unique IP address signal from various objects in the surrounding environment in order to measure a distance and an approaching speed of various objects.

In one embodiment of the NPS for vehicle/object (IoT device) 900, in order to avoid collision, at least one of a cellular base station (4G, 5G and beyond, 6G), a WiFi router, and a private network broadcasts to vehicle/object (IoT device) 900 a channel, a frequency, a modulation, and an absolute time with a time slot duration when its wireless sensor (slave IoT device) can broadcast its information data.

In another embodiment of the NPS for vehicle/object (IoT device) 900, the wireless sensor (slave IoT device), over the air, broadcasts information data that includes a time stamp indicating time of day, a method the time of day was obtained (IEEE1588, cyclic prefix, downlink unused subcarriers, downlink channels unused bits/messages or GPS), type of the vehicle/object (IoT device) 900, location coordinates (obtained from GPS receiver), the identity number or IP (media access control MAC) address of wireless sensor (slave IoT device), signal propagation time through transmitter of the wireless sensor (slave IoT device) up to the input of transmit antenna, and estimated mass of the vehicle/object (IoT device) 900.

In one embodiment of the NPS for vehicle/object (IoT device) 900, two or more type of sensors can be used to better monitor the surrounding environment of the vehicle/object (IoT device) 900 and calculate and estimate parameters of the surrounding environment.

In one embodiment of the NPS for vehicle/object (IoT device) 900, an image sensor is used to monitor the vehicle/object (IoT device) 900 surrounding environment, and independently calculate and estimate a distance and an approaching speed of an object in its surrounding environment.

In one embodiment of the NPS for vehicle/object (IoT device) 900, using typical objects in an environment an image verification data base and a distance calibration data base that relates the size of the image to distance of the object from the image sensor is created and stored in memory of the image sensor.

In one embodiment of the NPS for vehicle/object (IoT device) 900, a wireless sensor (slave IoT device) and an image sensor are used to monitor the vehicle/object (IoT device) 900 surrounding environment, and each independently calculate and estimate a distance and an approaching speed of the objects in its surrounding environment and use the information data to make a better decision (by the artificial intelligence) to activate one or more multilayer air bags and/or expandable pads.

In another embodiment, the vehicle/object (IoT device) 900 can be an automobile, a robot, a flying car, a small plane, a drone, a glider, a human or any flying and moving vehicle/device/object/equipment.

Figure 12:
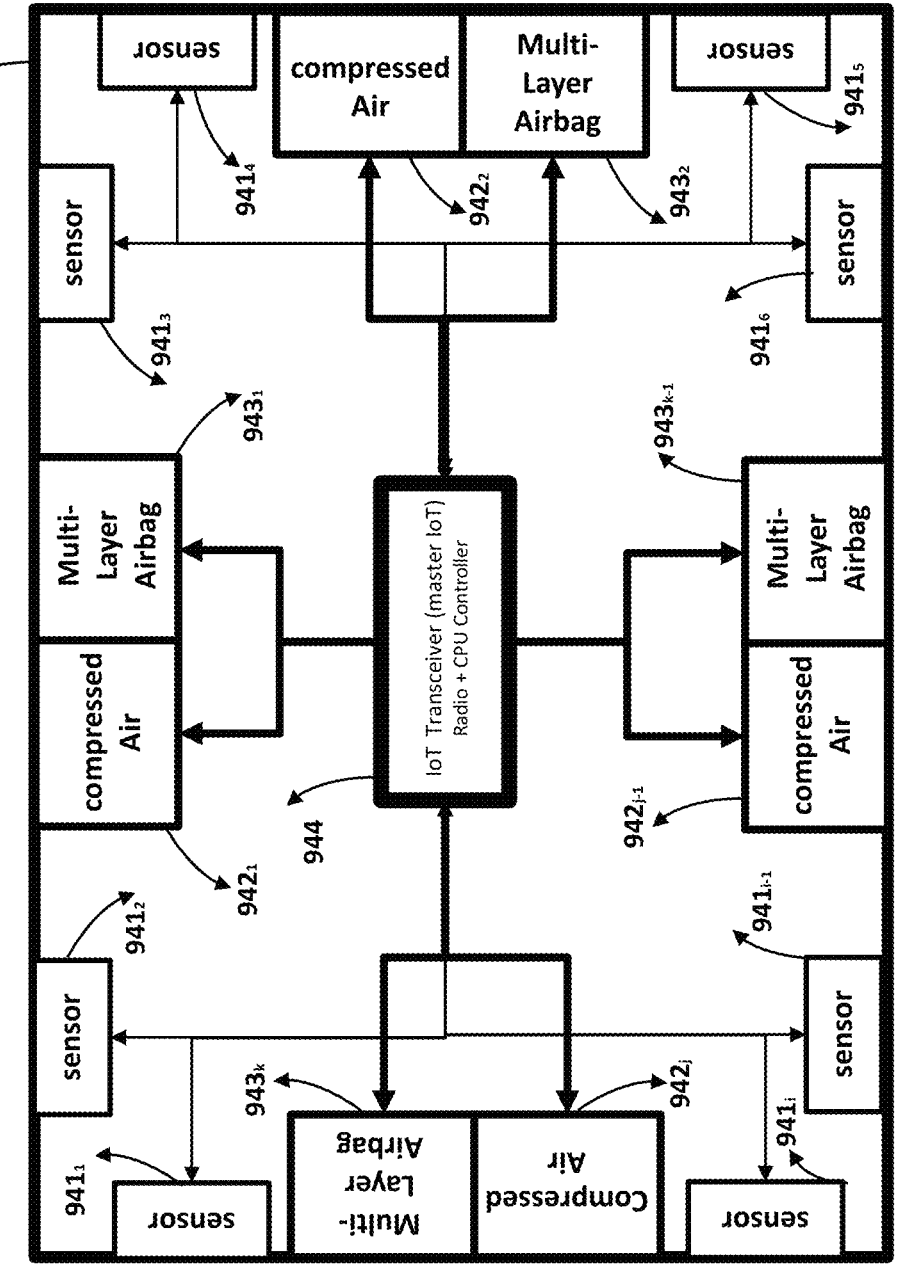
FIG. 12 illustrates an IoT protection system for flying objects

FIG. 12 illustrates an embodiment of a NPS for a flying object (IoT device) 940. In general, the NPS for the flying object (IoT device) 940 provide protection by releasing compressed air and/or inflating a multilayer airbag, and control the navigation. The NPS receives information data related to operation status and surrounding environment of the flying object (IoT device) 940 from IoT transceiver (master IoT device) 944, sensors (including wireless sensors, and slave IoT device) 941$_1$ to 941$_i$ to detect any malfunction of the flying object (IoT device) 940 that results in loss of altitude, vertical fall due to gravity force and eventual crash to the ground. When the NPS detects a fall through its CPU controller's artificial intelligence which analyses the information data received from the monitoring devices/sensors (including wireless sensors, and slave IoT devices) 941$_1$ to 941$_i$ which include information data related to devices internal to flying object (IoT device) 940 and its surrounding environment's parameters, it broadcasts its problem using IoT transceiver (master IoT device) 944 and activates at least one of the compressed air 942$_1$ to 942$_j$ to release air to slow down the fall at certain distance from ground before the flying object (IoT device) 940 crashes and then activates one or more of the multilayer airbag 943$_1$ to 943$_k$ for smoother landing or crash.

The NPS for the flying object (IoT device) 940 includes, among other things, sensors (including wireless sensors, and slave IoT devices) 941$_1$ to 941$_i$, IoT transceiver (master IoT device) 944, compressed air units 942$_1$ to 942$_j$, and multilayer airbags 943$_1$ to 943$_k$.

In one embodiment of the NPS for the flying object (IoT device) 940, activation of a subset of compressed air units 942$_1$ to 942$_j$ and multilayer airbags 943$_1$ to 943$_k$ allows for smoother crash or landing on any side of the flying object (IoT device) 940.

In one embodiment, the NPS for the flying object (IoT device) 940 uses a centralized compressed air unit with multiple outlets at different sides of the flying object (IoT device) 940 and when activated the air is released only from the outlets on the side that flying object (IoT device) 940 lands or crash to the ground.

In one embodiment of the NPS for the flying object (IoT device) 940, one or more of the multilayer airbags 943$_1$ to 943$_k$ at one or multiple sides of the flying object (IoT device) 940 are inflated to make the crash or landing as smooth as possible.

In one embodiment of the NPS for the flying object (IoT device) 940, NPS through the controller CPU of the IoT transceiver 944 resets, and configures itself based on a configuration data stored in its memory and then starts executing an artificial intelligence software which controls all aspects of navigation and protection of the flying object (IoT device) 940 using information data provided by sensors (including wireless sensors, and slave IoT devices) 941$_1$ to 941$_i$.

In one embodiment of the NPS for the flying object (IoT device) 940, each sensor has an IP (MAC) address which is used to communicate with the IoT transceiver 944 similar to an IP network to avoid collision or confusion of the information data received by the IoT transceiver 944 from sensors internal or external to the flying object (IoT device) 940.

In one embodiment of the NPS for the flying object (IoT device) 940, each sensor sends its information data to the controller CPU of the IoT transceiver (master IoT device) 944 by using wireless and/or wired communication.

In another embodiment, the flying object (IoT device) 940 can be a drone, a flying car, a small plane, a glider, and a flying human or robot.

Figure 13:
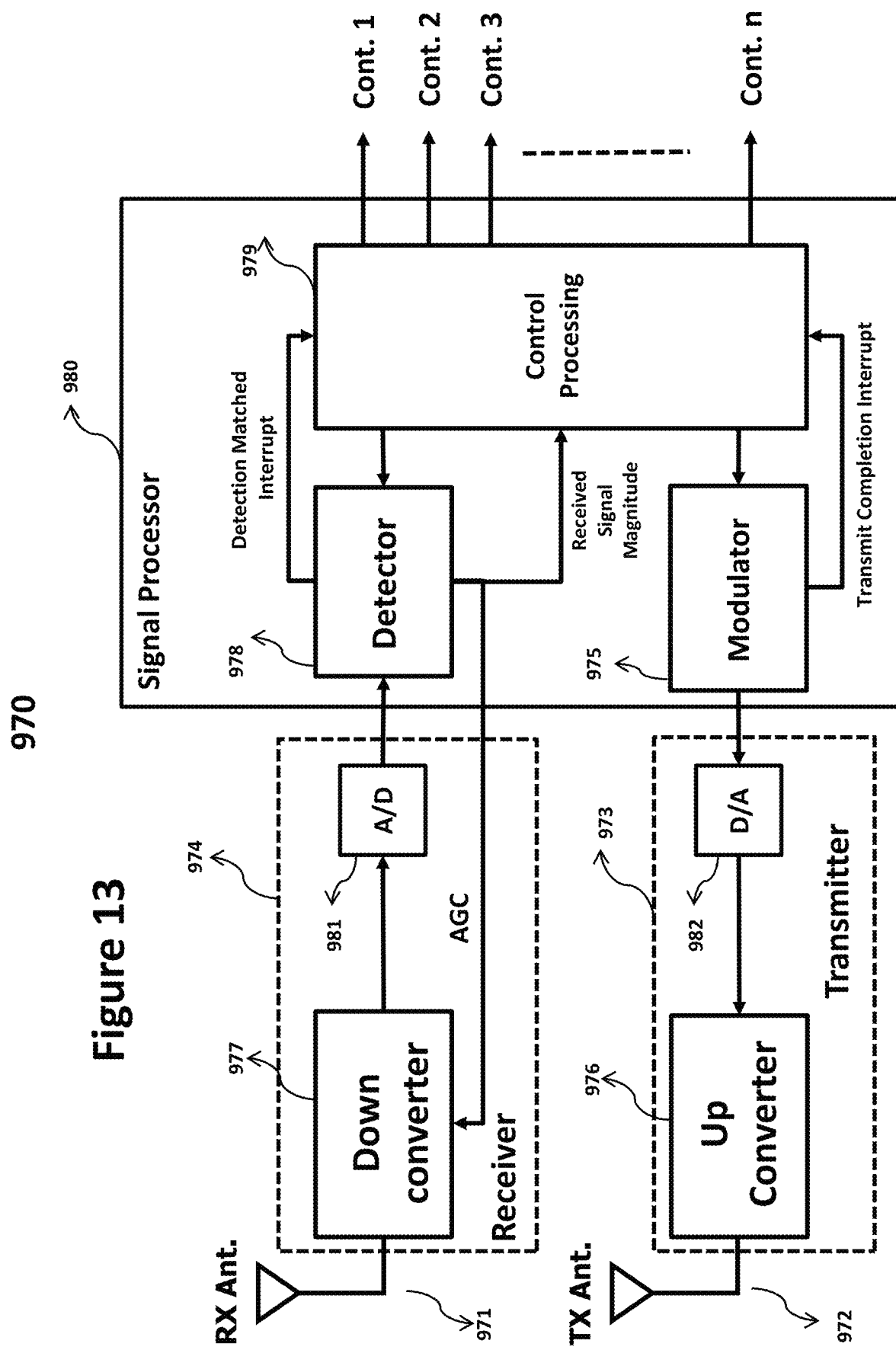
FIG. 13 depicts an embodiment of a wireless sensing system

FIG. 13 depicts an embodiment of wireless sensor system 970 (or IoT device 300, 400, and 500). In general, wireless sensor system 970 (or IoT device 300, 400, and 500) facilitates estimation and calculation of certain environment's parameters by transmitting a coded signal like a unique IP address (or a broadcast, Ethernet frame or packet) signal generated or selected by a control processor 979 through a modulator 975, a transmitter 973 and antenna 972 and then receiving the attenuated version of reflected coded signal (or a broadcast and Ethernet frame or packet) by an antenna 971, receiver 974 and detector 978. For example, control processor 979 selects an IP address pattern from a pool of IP addresses (or a broadcast and Ethernet frame or packet), send it to modulator 975 for modulation then the modulated signal is sent to transmitter 973 to be converted to analog signal by digital-to-analog (D/A) converter 982 and up converted to carrier frequency by up convertor 976 for transmission through antenna 972. The modulator 975 also sends the time of completion of modulation to control processor 979. Then the reflected transmit (a broadcast or an Ethernet frame or packet) signal from an object in the environment is received by antenna 971 and receiver 974, where it is down converted by down convertor 977 and converted to digital signal by analog-to-digital (ND) converter 981. The digitized received signal is processed in signal processing unit 980, where it is detected by detector 978 and detection time is sent to control processor 979. The digitized down converted received signal also facilitates measurement of received signal strength intensity (RSSI) to provide to control processor 979.

Wireless sensor system 970 (or IoT device 300, 400, and 500) includes, among other things, signal processor 980, transmitter 973, transmit antenna 972, receive antenna 971, and receiver 974.

In one embodiment, signal processor 980, transmit antenna 972, transmitter 973, receive antenna 971, and receiver 974 are components of wireless sensor system 970 (or IoT device 300, 400, and 500) that could be used for various applications. For example, it can be used to communicate with a cellular network (4G, 5G, 6G and beyond), a private network, a WiFi network, transmit and receive a broadcast frame or packet, transmit and receive an Ethernet frame or packet, communicate with the cloud, and etc.

In one embodiment, wireless sensor system 970 (or IoT device 300, 400, and 500) receives information about its surrounding environment which includes various objects and their types from the cellular network (4G, 5G, 6G and beyond), the WiFi network or the private network. Wireless sensor system 970 (or IoT device 300, 400, and 500) also receives an IP address to use for its operation or a pool of IP addresses it can store and use as needed.

In another embodiment, wireless sensor system 970 (or IoT device 300, 400, and 500) uses GPS to obtain time of day, clock synchronization and location coordinates.

In one embodiment, wireless sensor system 970 (or IoT device 300, 400, and 500) uses IEEE1588 and through the cellular network (4G, 5G, 6G and beyond), the WiFi network, the private network, or another wireless sensor system (or IoT device 300, 400, and 500) obtains time of the day and clock synchronization.

In another embodiment, wireless sensor system (or IoT device 300, 400, and 500) 970 uses IEEE1588 PTP to obtain clock synchronization (syncE also can be used for clock synchronization) and time of day from a central CPU controller that it communicates with.

In another embodiment, wireless sensor system (or IoT device 300, 400, and 500) 970 obtains its IP (MAC) address from a central CPU controller that it communicates with.

In another embodiment, wireless sensor system 970 (or IoT device 300, 400, and 500) receives an absolute time for its activity such as transmission, reception, communication and broadcasting from the cellular network (4G, 5G, 6G and beyond), the WiFi network, the private network, or the central CPU controller that it communicates with.

In one embodiment, wireless sensor system 970 (or IoT device 300, 400, and 500) communicates its information and parameters to the cellular network (4G, 5G, 6G and beyond), the WiFi network, the private network, or the central CPU controller that it communicates with.

In one embodiment, wireless sensor system 970 (or IoT device 300, 400, and 500) receives an information data from its surrounding environment which is updated in real time from the cellular network (4G, 5G, 6G and beyond), the WiFi network, the private network, or the central CPU controller that it communicates with.

In one embodiment, wireless sensor system 970 (or IoT device 300, 400, and 500) broadcasts its information data to other wireless sensors (or IoT devices) that belong to various moving or stationary objects in its surrounding environment.

In another embodiment, wireless sensor system 970 (or IoT device 300, 400, and 500) fragments its transmit signal to two or more fragment signals, transmits each fragment signal and receives the reflection of each fragment signal from various objects in its surrounding environment before transmission and reception of next fragment signal.

In one embodiment, wireless sensor system 970 (or IoT device 300, 400, and 500) supports WiFi, Bluetooth, Zigbee or any other over the air protocol as well as physical layer.

In another embodiment, wireless sensor system 970 (or IoT device 300, 400, and 500) is used for other applications and transmits and receives Ethernet frames over the air.

In one embodiment, signal processor 980 that processes both transmit and receive signals comprises of control processor 979, modulator 975, and detector 978.

Signal processor 980 processes an information data transmitted from transmitter 973 through antenna 972 and an information data received from receiver 974 through receive antenna 971. The signal processor 980 also provides gain control for receiver and facilitates change of transceiver operating frequency, channel, and modulation. Signal processor 980 typically utilizes appropriate hardware and software algorithm to properly process the information data.

Wireless sensor system 970 (or IoT device 300, 400, and 500) can be any wireless transceiver that is able to wirelessly transmit communication signals. Wireless sensor system 970 (or IoT device 300, 400, and 500) is disposed on any physical platform that is conductive to effectively transmit the signals.

In one embodiment, communications through wireless system 970 (or IoT device 300, 400, and 500) are by a transmit antenna 972 and a received antenna 971. Transmit and receive antennas are physically separated to provide sufficient isolation between transmit and receive antennas. The transmit antenna 972 and the received antenna 971 can also be common or one antenna.

In one embodiment, communication through wireless system 970 (or IoT device 300, 400, and 500) is by a single antenna. In general at any specified period of time the antenna is selected by a switch and/or a circulator.

Signal Processor 980 has a variety of functions. In general, signal processor 980 is utilized for signal processing, calculation, estimation, activities, methods, procedures, and tools that pertain to the operation, administration, maintenance, and provisioning of wireless sensor system 970 (or IoT device 300, 400, and 500). In one embodiment, signal processor 980 includes a database that is used for various applications. The database can be utilized for analyzing statistics in real-time.

Signal processor 980 also has a variety of thresholds. In general, signal processor 980 provides controls to various components that are connected to it. Moreover, signal processor 980 is a high capacity communication facility that connects primary nodes.

In one embodiment, the wireless sensors system 970 (or IoT device 300, 400, and 500) uses microwave, or millimetric (from 10 GHz to 80 GHz or higher frequencies) wave transceiver.

In one embodiment, wireless sensor system 970 (or IoT device 300, 400, and 500) is controlled by control processor 979. The control processor 979 controls a transmit signal duration and number of times the transmit signal is transmitted. Control processor 979 also coordinates the transmit time and receive time period.

In one embodiment, the wireless sensor system 970 (or IoT device 300, 400, and 500) can be used for body armors, automobile, robots, drone, and any other stationary and moving equipment.

Figure 14A:
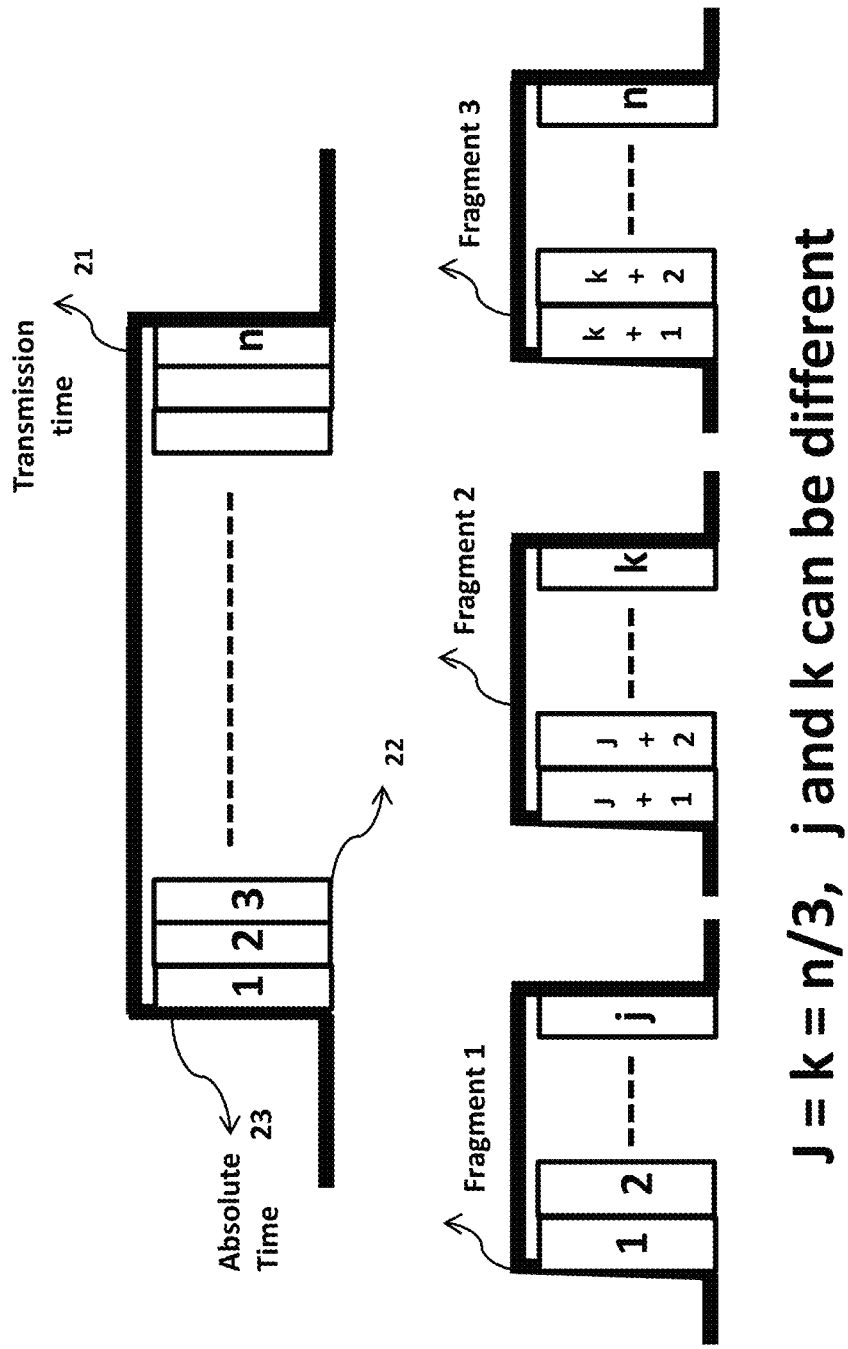
FIGS. 14A through 14D illustrate embodiments of transmit signal for wireless sensor.

FIG. 14A depicts an embodiment of transmit signal for wireless sensor system 970 shown in FIG. 13 (or IoT device 300, 400, 500, and 600 shown in FIGS. 3, 4, 5 and 6). The transmit signal has a transmission time (duration) 21 and a bit pattern 22. Pattern 22 can be a unique identity code, a unique IP address, random pattern, an entire broadcast frame or packet, and an entire Ethernet frame or packet which is generated by control processor 979.

In one embodiment of wireless sensor system 970 used in a NPS of a moving or flying vehicle/object defined in FIGS. 11 and 12, the pattern 22 is assigned to wireless sensor system 970 (or IoT device 300, 400, 500, and 600) at manufacturing when it is used for ranging.

In one embodiment of wireless sensor system 970 (or IoT device 300, 400, 500, and 600), the random pattern 22 (when it is used for ranging) may be changed after being used a few times based on the artificial intelligence in the controller 979. The change of transmit pattern 22 signal is for avoiding any collision or false detection from other signals in the surrounding environment.

In one embodiment of wireless sensor system 970 (or IoT device 300, 400, 500, and 600), the transmit signal 22 (when it is used for ranging) is an IP address (or identity code) unique to a NPS using the wireless sensor 970 (or IoT device 300, 400, 500, and 600). The IP address (or identity code) can be assign to wireless system 970 (or IoT device 300, 400, 500, and 600) at manufacturing. The IP address (or identity code) can also be assign to wireless sensor system 970 (or IoT device 300, 400, 500, and 600) in the field by the user. The IP address can be assigned each time the wireless sensor system 970 (or IoT device 300, 400, 500, and 600) transmits and performs ranging. The IP address (or identity code) can also be taken from a pool of IP addresses (or identity codes) stored in the control processor 979 (or IoT device 300, 400, 500, and 600) memory or a removable memory card which can be similar to a subscriber identity module (SIM) card.

In one embodiment of wireless sensor 970 (or IoT device 300, 400, 500, and 600), the transmit pattern duration 21 depends on the number of bit pulses in the transmit signal pattern, carrier frequency, bandwidth, and modulation level. The higher the number of bits in transmits identity code, IP address, random pattern, or broadcast (Ethernet) frame or packet the longer the transmit signal duration.

In one embodiment of wireless sensor 970 (or IoT device 300, 400, 500, and 600), the number of bits in the pattern 22 defines the accuracy of the receiver detection (when it is used for ranging).

In another embodiment, the transmit bit pattern 22 is fragmented to smaller bit patterns, shown in FIG. 14A, to allow use of lower carrier frequency, less bandwidth, or lower level modulation.

In one embodiment, wireless sensor system 970 (or IoT device 300, 400, 500, and 600) transmits the first fragment with "j" bits, receives the reflected transmit signal from objects in surrounding environment of wireless sensor system 970 (or IoT device 300, 400, 500, and 600), then transmit the second fragment with "k j" bits, and finally transmits the last fragment with "n-j-k" bits and receives the reflected transmit signal from objects in surrounding environment of wireless sensor system 970 (or IoT device 300, 400, 500, and 600) for detection of the transmit bit pattern.

In another embodiment, the fragment bit patterns can have equal number of bits, or different number of bits.

In one embodiment of wireless sensor system 970 (or IoT device 300, 400, 500, and 600), the start of transmission time 21 or start of first bit in bit pattern 22 is an absolute time 23 configured in the controller. This absolute time is derived from time of day wireless sensor 970 (or IoT device 300, 400, 500, and 600) obtains from GPS receiver, a cellular network (4G, 5G and beyond), a WiFi network, a private network, or a central controller that communicates with. The absolute time can also be sent to wireless sensor 970 (or IoT device 300, 400, 500, and 600) by the cellular network (4G, 5G, 6G and beyond), the WiFi network or the private network. The absolute time can be first microsecond in a millisecond, or the nth microsecond after the start of a millisecond.

In addition to absolute time the cellular network (4G, 5G, 6G and beyond), the WiFi network or the private network assigns to the wireless sensor 970 (or IoT device 300, 400, 500, and 600) a time slot that starts from the absolute time and has a duration which is equal for all objects that use wireless sensor 970 (or IoT device 300, 400, 500, and 600) in the environment. The time slot duration assigned to the objects using wireless sensor 970 (or IoT device 300, 400, 500, and 600) can also be different.

In one embodiment, the absolute time can be any nanosecond within a microsecond period, such as $1^{st}$ nanosecond, kth nanosecond, nth nanosecond, and etc.

In one embodiment of wireless sensor 970 (or IoT device 300, 400, 500, and 600), the time of day obtained from GPS receiver or from the 4G, 5G, 6G, the WiFi network or the private network using IEEE1588 has accuracy within a few nanosecond, fraction of microsecond, or fraction of nanosecond.

In one embodiment the time of day obtained from GPS receiver or from the 4G, 5G, 6G, the WiFi network or the private network using IEEE1588 is based on Coordinated Universal Time (UTC).

In another embodiment, an absolute time used for broadcasting by wireless sensor 970 (or IoT device 300, 400, 500, and 600) in the smart environment 700 and 800 defined in FIGS. 7 and 8 helps to avoid any collision when various objects broadcast their information.

Figure 14B:
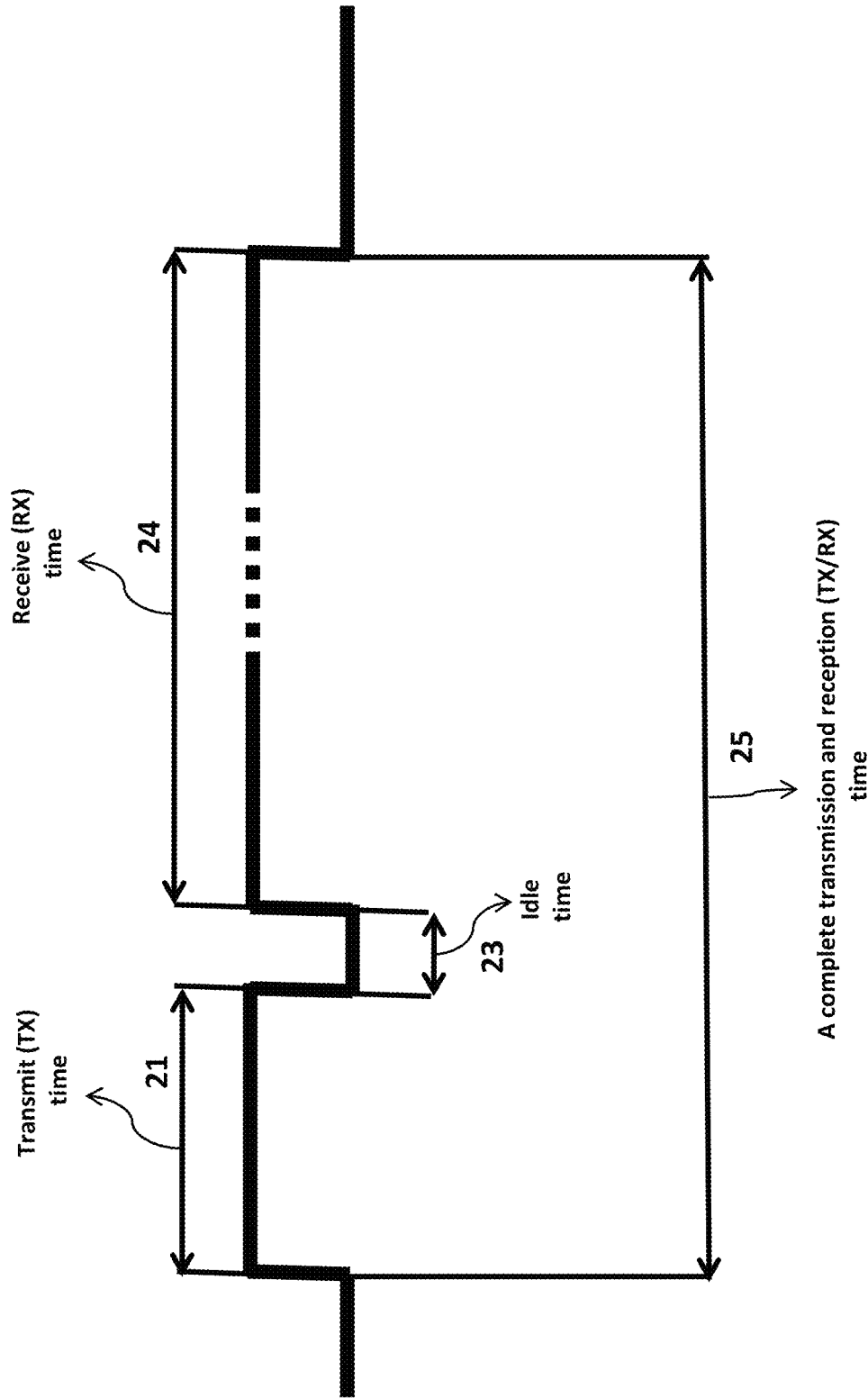

FIG. 14B shows the duration of a complete single transmission and reception (single measurement time) 25 for wireless sensor system 970 (or IoT device 300, 400, 500, and 600) when it is used for ranging. The complete transmission and reception duration comprises of the transmit time (duration) 21, idle time (duration) 23 and receive time (duration) 24.

In one embodiment of wireless sensor system 970 (or IoT device 300, 400, 500, and 600), the idle time 23 is zero. The idle time can vary based on proximity of an object to wireless sensor 970 (or IoT device 300, 400, 500, and 600) in its surrounding environment. The closer the object the smaller the idle time 23 is. In most circumstances the idle time is zero and after completion of transmission the wireless sensor system 970 (or IoT device 300, 400, 500, and 600) start its reception.

In one embodiment of the wireless sensor system 970 (or IoT device 300, 400, 500, and 600), the receive time 24 depends on the monitoring radius of surrounding environment of the wireless sensor system 970 (or IoT device 300, 400, 500, and 600). The bigger the radius of monitoring the longer the reception time of wireless sensor system 970 (or IoT device 300, 400, 500, and 600) is. Therefore, the assigned time slot for a complete transmission and reception depends on the monitoring radius.

In another embodiment, when the wireless sensor system 970 (or IoT device 300, 400, 500, and 600) is used to transmit and receive broadcast or Ethernet packets the time slot duration depends on three parameters. One is maximum length of a packet allowed for both broadcast and Ethernet packet. Second is the monitoring radius, and the third is error in time of day that is used to derive absolute time. In real operation it is rare to have time of day error more than 100 nanosecond and monitoring radius is usually less than 30 feet which is equivalent to 30 nanoseconds. The time of day (TOD) is also updated regularly which eliminates accumulation of time of day error. Therefore, time slot duration of 2 microseconds is sufficient for broadcast and Ethernet packets of an object in a smart environment when a 70 GHz to 80 GHz band is used. This allows to assign one thousands absolute time with a time slot duration of 2 microsecond within two millisecond. Each object is assigned one or more time slot with its associated start time that is the absolute time.

Figure 14C:
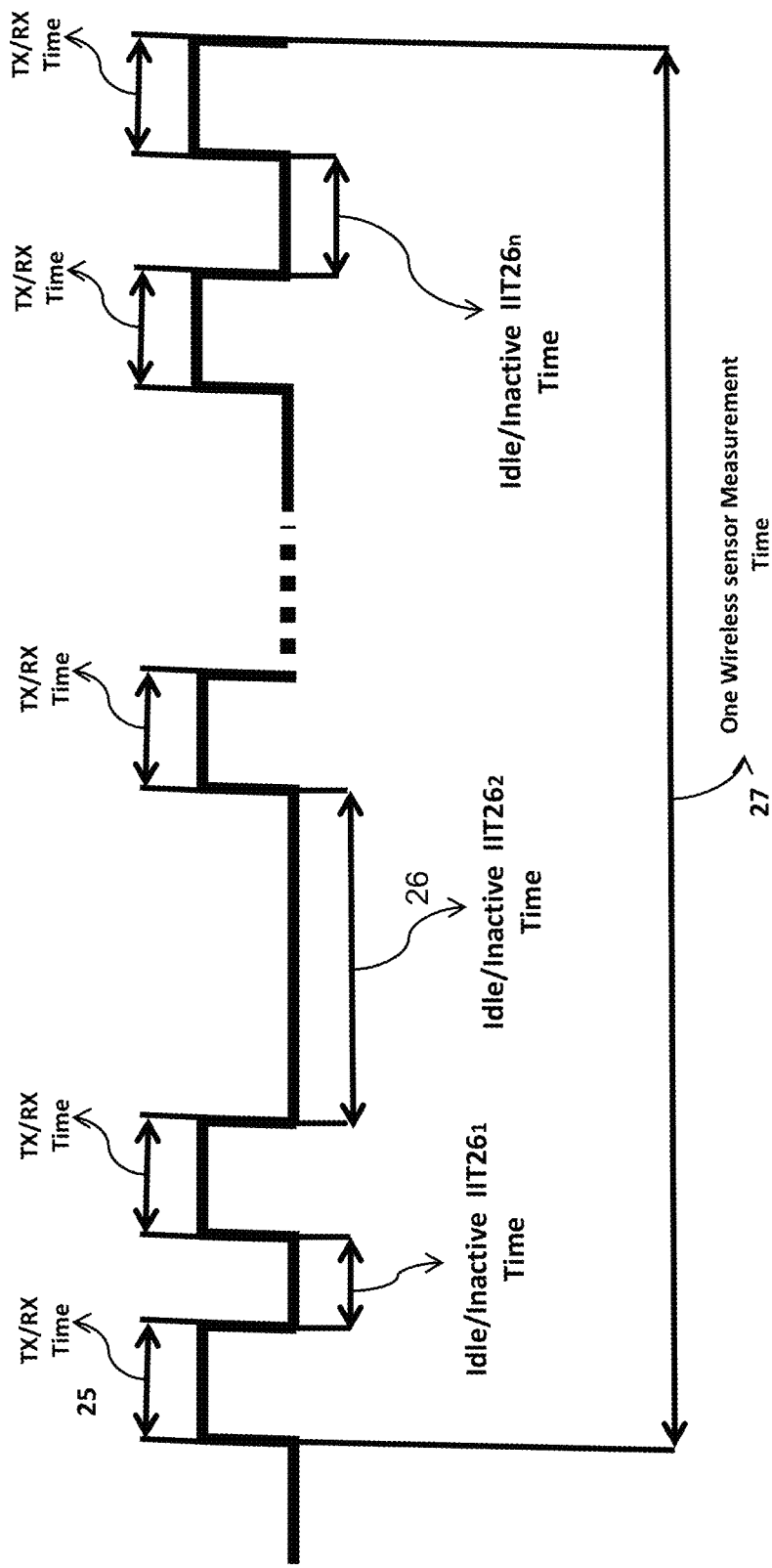

FIG. 14C shows the duration of a complete measurement time 27 of wireless sensor system 970 (or IoT device 300, 400, 500, and 600) when used for ranging. It comprises of "n+1" single complete transmission and reception (single measurement) times 25 and the idle/inactive times IIT26$_1$ to IIT26$_n$ between single complete transmission and reception (single measurement) times.

In one embodiment of the wireless sensor system 970 (or IoT device 300, 400, 500, and 600), idle/inactive times IIT26$_1$ to IIT26$_n$ can have the same duration or randomly different duration based on artificial intelligence assessments. Artificial intelligence within wireless sensor system 970 (or IoT device 300, 400, 500, and 600) control processor or control processor of a NPS that uses the wireless sensor 970 (or IoT device 300, 400, 500, and 600) defines the idle/inactive time duration to avoid any reception collision with transmit signals from other objects in the surrounding environment of the wireless sensor system 970 (or IoT device 300, 400, 500, and 600).

In one embodiment of the wireless sensor system 970 (or IoT device 300, 400, 500, and 600), the artificial intelligence within the control processor of wireless sensor system 970 or control processor of a NPS that uses the wireless sensor can use a number of measurement times 27 for assessment of the surrounding environment before deciding to activate any function or devices.

Figure 14D:
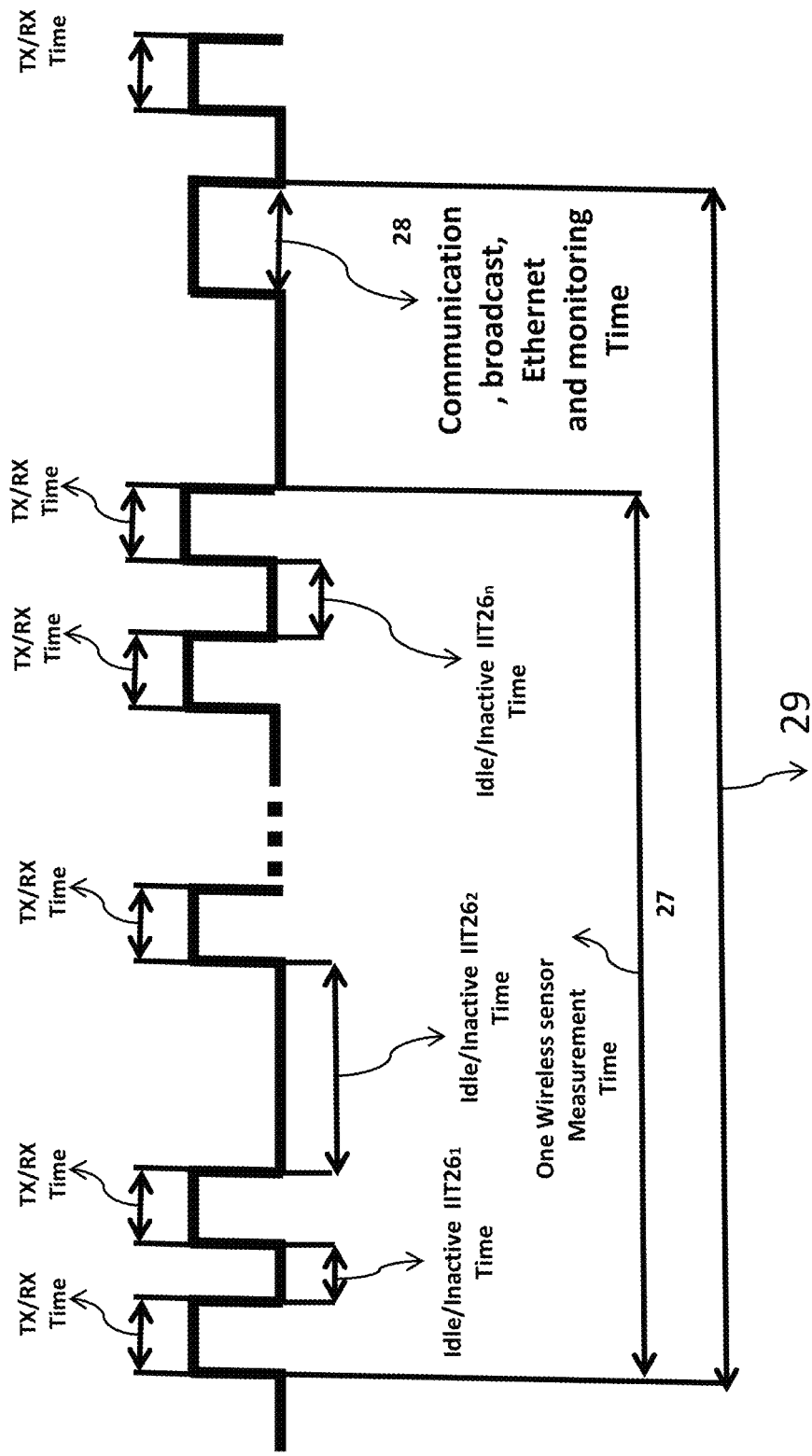
Figure 15B:
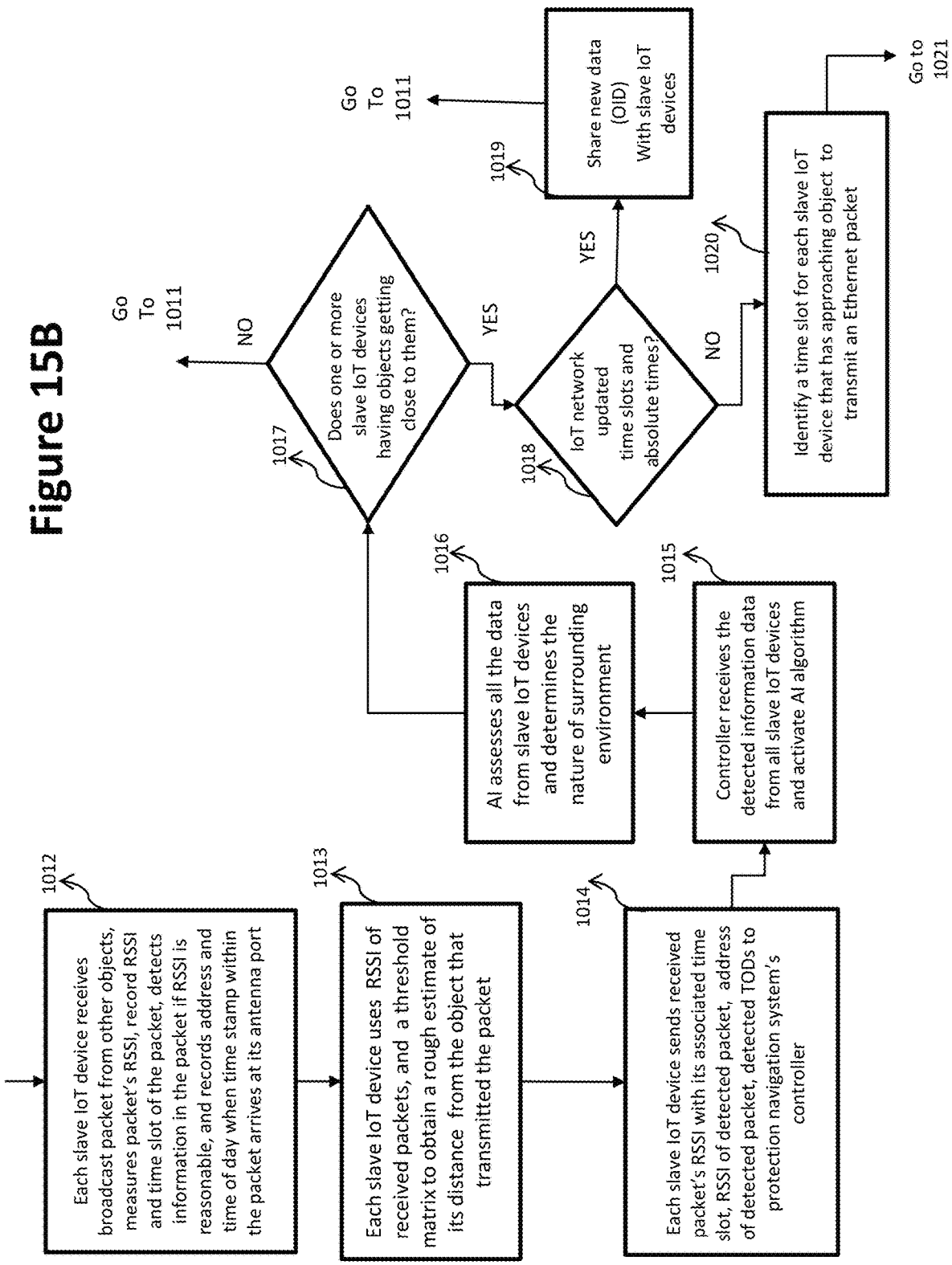
Figure 15C:
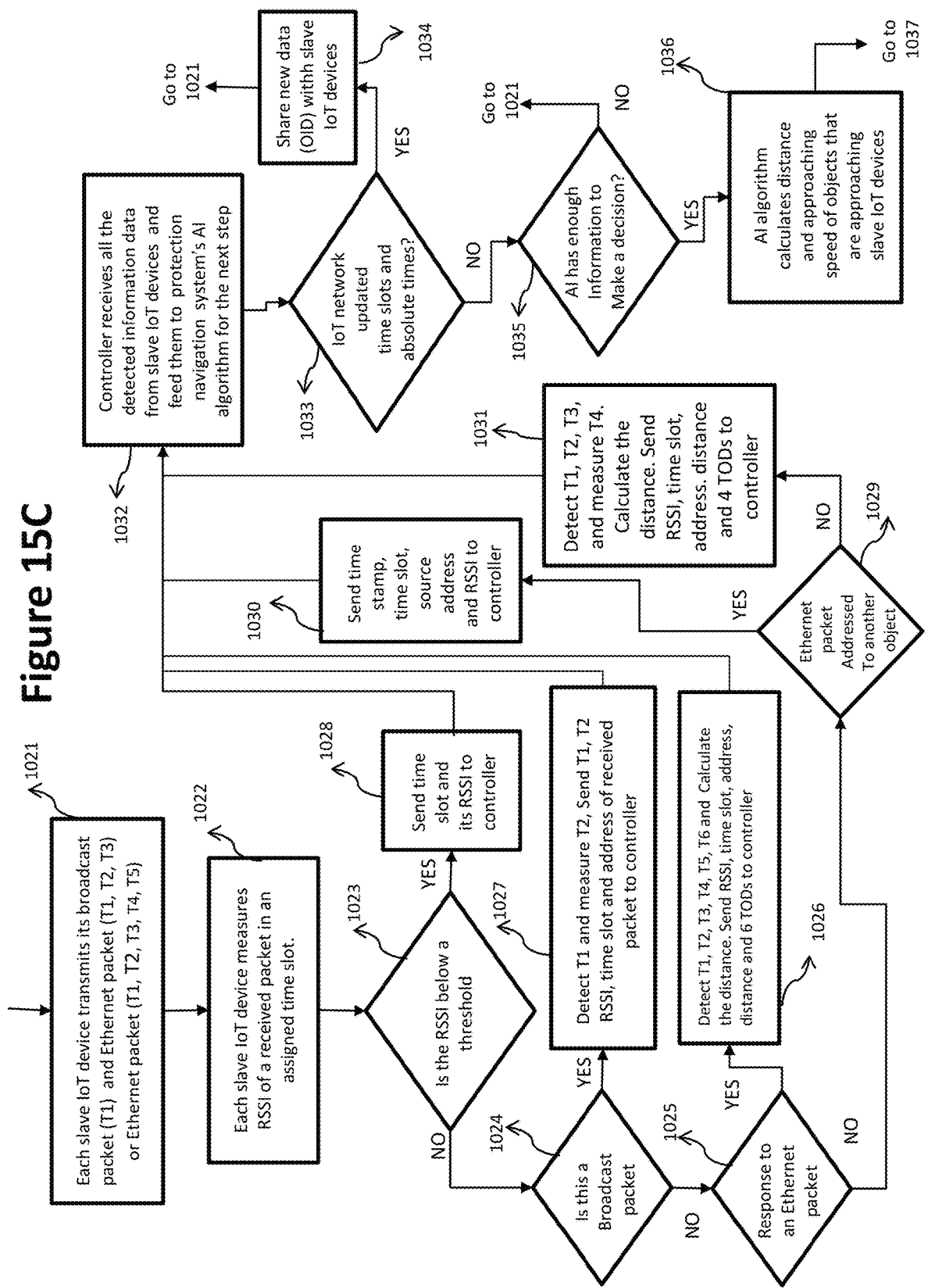
Figure 15D:
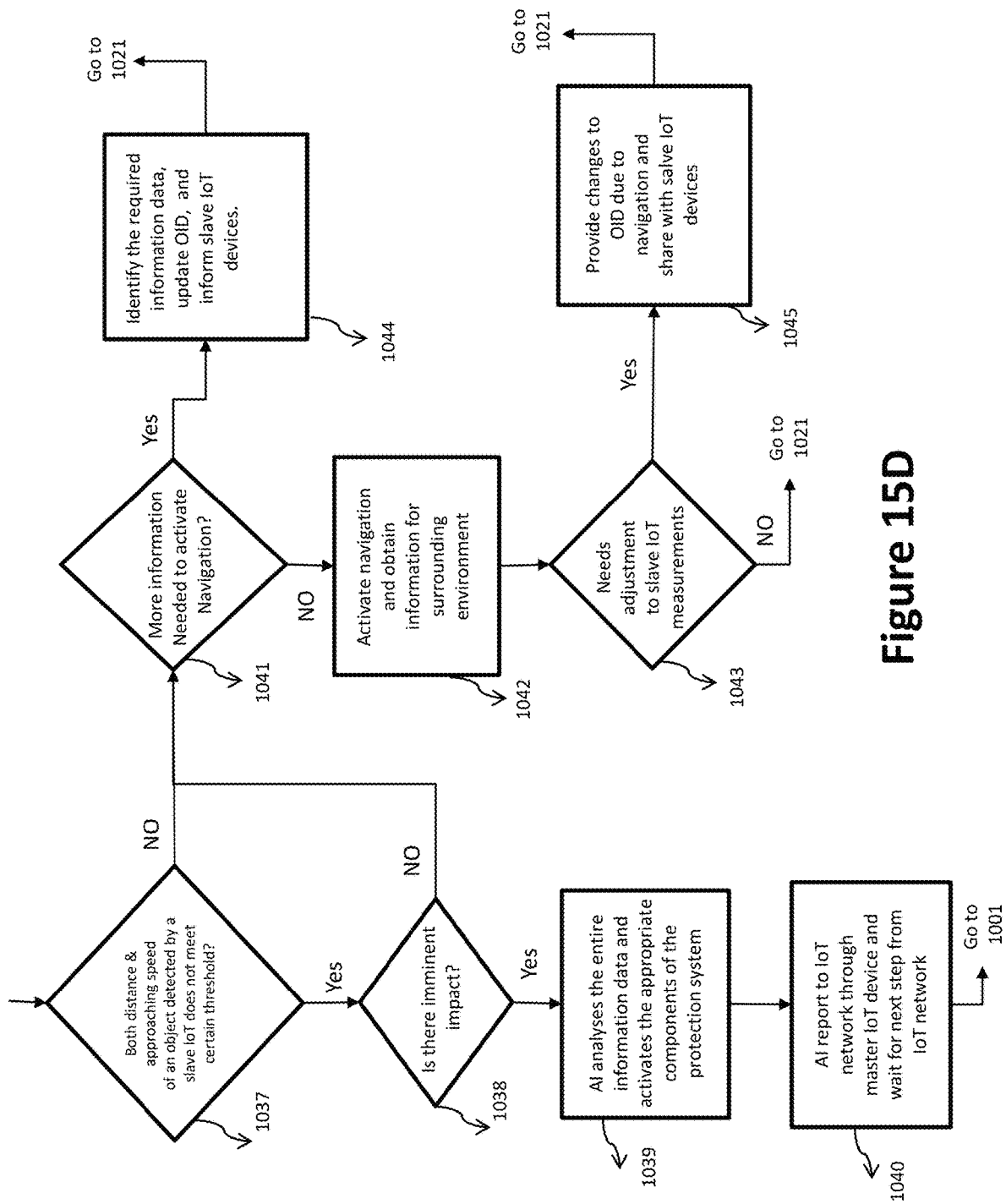

FIG. 14D depicts the duration of a complete measurement time 27 and communication/broadcast/Ethernet/monitoring time 29 of wireless sensor system 970 (or IoT device 300, 400, 500, and 600).

In one embodiment, the communication time, broadcast time, Ethernet time and monitoring time of wireless sensor system 970 (or IoT device 300, 400, 500, and 600) are all achieved during time 28 assigned to these tasks. If there is no ranging and monitoring then the entire time 29 is assigned to transmitting and receiving broadcast and Ethernet packets. Therefore, time slot duration of 2 microseconds is sufficient for broadcast and Ethernet packets of an object in a smart environment when a 70 GHz to 80 GHz band is used. This allows to assign one thousands absolute times with a time slot duration of 2 microsecond within two millisecond. Each object is assigned one or more time slot and the start of each time slot is the absolute time. In case the time slot durations are equal and each object is assigned one time slot then the only information that each object requires are absolute time, time slot duration and total number of time slot. These three information specifies to object's wireless sensor system 970 (or IoT device 300, 400, 500, and 600) when the first transmission or reception of broadcast or Ethernet packet is. Therefore, the second transmission and reception is 2 milliseconds later. The wireless sensor system 970 (or IoT device 300, 400, 500, and 600) can also transmit and receive Ethernet packets during the time slots that assigned to other objects but the RSSI of received signal at those time slots is negligible. This feature will be used by AI algorithm to better manage the NPS.

In another embodiment, wireless sensor system 970 (or IoT device 300, 400, 500, and 600) only communicates with an IoT device, a cellular network (4G, 5G, 6G, 7G and beyond), a WiFi network or a private network during time 28.

In another embodiment, wireless sensor system 970 (or IoT device 300, 400, 500, and 600) performs only over the air broadcasting task as well as transmission of Ethernet packets during time 28.

In one embodiment, wireless sensor system 970 (or IoT device 300, 400, 500, and 600) performs only monitoring of broadcast and Ethernet packets from other objects in its surrounding environment during time 28.

In another embodiment, wireless sensor system 970 (or IoT device 300, 400, 500, and 600) performs two of three tasks (communication, broadcast/Ethernet, monitoring) during time 28.

In one embodiment, an absolute time is sent by the cellular network (4G, 5G, 6G, 7G and beyond), the WiFi network or the private network for the start of time 28 to each wireless sensor system 970 (or IoT device 300, 400, 500, and 600) for communication, broadcast/Ethernet transmission, broadcast/Ethernet reception, and monitoring.

In another embodiment, the cellular network (4G, 5G, 6G, 7G and beyond), the WiFi network or the private network shares with each wireless sensor system 970 (or IoT device 300, 400, 500, and 600) in a smart environment the absolute time of all the registered wireless sensor system 970 (or IoT device 300, 400, 500, and 600).

In one embodiment, each wireless sensor system 970 (or IoT device 300, 400, 500, and 600) is aware of absolute time of broadcasting, monitoring and communication of all wireless sensor systems 970 (or IoT device 300, 400, 500, and 600) in its smart environment.

In another embodiment, the wireless sensor system 970 (or IoT device 300, 400, 500, and 600) sends and receives Ethernet frame or packet to another wireless sensor system 970 (or IoT device 300, 400, 500, and 600) in its smart environment during the time slot assigned to it.

In one embodiment, wireless sensor system 970 (or IoT device 300, 400, 500, and 600) monitors the broadcast signal from other wireless sensor system 970 (or IoT device 300, 400, 500, and 600) in its smart environment using the absolute time (in time 28) assigned by the cellular network (4G, 5G, 6G, 7G and beyond), the WiFi network or the private network.

In another embodiment, wireless sensor system 970 (or IoT device 300, 400, 500, and 600) does not perform ranging to calculate distance from an object and performs communication, broadcasting, or monitoring using the absolute time and time slot assigned to it by the cellular network (4G, 5G, 6G, 7G and beyond), the WiFi network or the private network.

In one embodiment, wireless sensor system 970 (or IoT device 300, 400, 500, and 600) is used only to measure the distance between two objects (or IoT device 300, 400, 500, and 600) using time of day and broadcast packets.

In another embodiment, wireless sensor system 970 (or IoT device 300, 400, 500, and 600) is used only to measure the distance between two objects (or IoT device 300, 400, 500, and 600) using time of day, broadcast packets, and Ethernet packets.

In another embodiment, wireless sensor system 970 (or IoT device 300, 400, 500, and 600) is aware of the absolute times and time slot durations (if time slot durations are different) assigned to all other wireless sensor systems 970 (or IoT device 300, 400, 500, and 600) in its smart environment.

In another embodiment, all wireless sensor systems 970 (or IoT device 300, 400, 500, and 600) in a smart environment are registered with only one cellular network (4G, 5G, 6G, 7G and beyond), WiFi network or private network.

In another embodiment, all wireless sensor systems 970 (or IoT device 300, 400, 500, and 600) in a smart environment are registered with one or more cellular networks (4G, 5G, 6G, 7G and beyond), WiFi networks or private networks that are linked and share, control and manage the information (absolute times, time slot duration, function, type, location, time of day and etc.) received from all wireless sensor systems 970 (or IoT device 300, 400, 500, and 600).

In order for a navigation and protection system (NPS) to operate in all circumstances an artificial intelligent (AI) algorithm is used that receives information data from following source:
1. All internal sensors used by an object.
2. Wireless sensors that perform ranging to provide a distance between two objects and an approaching speed of the two objects towards each other.
3. Image sensors that also provide the same information as wireless sensor as well as image identification of the objects.
4. IoT devices that in conjunction with IoT network provide a distance between two objects and an approaching speed of the two objects towards each other using time of day (TOD).

AI algorithm requires information data from at least two of the above sources to be able to make a decision. Having access to more than two sources results in a more accurate decision and better support for navigation system and activating the more effective devices within protection system.

FIGS. 15A through 15D depict an embodiment of a process 2000 for using an IoT device (wireless sensor system 970 or IoT device 300, 400, 500, and 600) by an object to estimate and calculate environmental parameters. The distance between two objects using an IoT device (wireless sensor system 970 or IoT device 300, 400, 500, and 600) is possible to measure accurately if the two IoT devices that belong to two objects have line-of-site communication path. Therefore, the process 2000 requires identifying if there is a line-of-site between two IoT devices used by two objects in order to estimate distance between two objects using time of day (TOD). In various embodiments, the process 2000 is carried out by processor and electrical circuit under the control of a processes or executable instructions. The readable and executable instructions reside, for example, in a data storage medium such as processor usable volatile and non-volatile memory. However, the readable and executable instructions may reside in any type of processor readable storage medium. In some embodiments, the process 2000 is performed at least by one of the circuits described herein.

There are several parameters that may be used to identify whether a broadcast (Ethernet) packet signal received by an IoT device from another IoT device in the smart environment is a line-of-site signal. The start time of a broadcast packet signal is an absolute time of day sent to the IoT device by an IoT network. The IoT device sends a time stamp which is the time of day (TOD) at its antenna output port in its broadcast (Ethernet) packet signal to assist estimation of the distance between IoT devices. The absolute time is assigned to the IoT device (wireless sensor system 970 or IoT device 300, 400, 500, and 600) by the IoT network servicing the IoT device in a smart environment and it is shared with all other IoT devices registered with the IoT network. Therefore, it can be used to identify whether a received broadcast packet is line-of-site. This is achievable if all IoT devices registered with the IoT network have time of day with negligible error (less than 10 nanosecond).

Another parameter that may be very useful in identifying a line-of-site broadcast (Ethernet) packet signal received by the IoT device is the receive signal strength intensity (RSSI). IoT device's receiver measures the RSSI of received broadcast packet during the duration of the packet. RSSI is compared against a table of thresholds for a number of distances between two IoT devices in order to identify if the received broadcast packet is a line-of-site one. The RSSI threshold table has two columns. It is based on a reference output power which can be assigned to all IoT devices in the smart environment or zero dBm which is a logical reference level. Therefore, one column of the RSSI table is line-of-site distance and the other column is RSSI for a transmitted power of zero dBm. In order to create this table, free space path loss which uses the distance the broadcast signal travels and the frequency that carries the broadcast signal is used.

Gain and radiation pattern of the antennas used by the IoT device that transmits the broadcast (Ethernet) packet signal and the IoT device that receives the transmitted broadcast (Ethernet) packet signal are other parameters that may be used to identify if received signal is a line-of-site one. Gain (0.00 dB) and radiation pattern (Omni-directional) are used to create RSSI threshold table.

A moving or flying object may use multiple IoT devices (wireless sensor system 970 or IoT device 300, 400, 500, and 600) as shown in FIGS. 11 and 12 to monitor its surrounding environment as well as sensors and monitoring devices that are used internal or external to the object. In this case IoT device 904 or 944 acts as a master and is used to communicate, register, receives information data, transmit information data, obtain time of day (TOD) and synchronize to an IoT network. The master IoT device 904 or 944 also shares the information data it receives from the IoT network with other slave IoT devices/wireless sensors/monitoring devices ($901_1$ to $901_i$). All IoT devices including the master IoT device monitor the surrounding environment of the object and participate in identifying if a received broadcast (Ethernet) signal is from a line-of-site path.

The object's navigation and protection system's (NPS's) operation process 2000 is activated at start 1000. The objects navigation and protection system (NPS) shown in FIGS. 11 and 12 comprises of a central controller, a master IoT device, a plurality of slave IoT devices, other internal and external sensors and monitoring devices, protection devices such as multilayer airbags, compressed air tanks with multiple outlets, expandable pads (by applying voltage at two end of the pad), and navigation devices (steering wheel, accelerator, break, alarm, horn, high beam light and etc.). In addition to sensors and monitoring devices mentioned earlier two key sensors are wireless sensors for ranging and image sensors for ranging and identification of objects in the smart environment.

At 1001 the master IoT device registers with one of the available 5G, beyond 5G, 6G and beyond or WiFi IoT network. The master IoT device can have an account with all the operators that support IoT network or use roaming to be connected at all times. All IoT networks from different service providers or operators share the same data base and operation and management center (SOMC) for navigation and protection system's operation process 2000. The master IoT device after registering with IoT network shares its location coordinates, and detail information (type, model, dimensions, capabilities, etc.) of the object to be stored in shared database in the cloud. The shared operation and management center (SOMC) uses the stored location coordinates of the master IoT devices used by NPSs (and regularly updated in shared data base) to assign an absolute time and a time slot to master IoT device. The master IoT device shares the absolute time and the time slot with a controller used by NPS. The controller shares the data with all slave IoT devices used by NPS. If the time slot duration is identical for all master IoT devices then each NPS needs its own assigned time slot, absolute time, and number of time slots. If the time slot duration is different for master IoT devices or NPSs then each NPS needs to have all absolute times and the time slot durations assigned to all master IoT devices or NPSs in the smart environment. Master IoT device (a component of NPS) or NPS from assigned absolute times and time slots can calculate the start and end of one measurement cycle or transmission and reception of broadcast and Ethernet packets for all objects in the smart environment. In addition to absolute times and time slots for different activities, shared operation and management center (SOMC) assigns a frequency, a channel, a bandwidth, a modulation method, and an effective radiation power (ERP) to the master IoT devices or NPSs based on their location coordinate. The ERP assigned to NPS is for the slave IoT devices used by NSP. Master IoT device uses an ERP for communication with IoT network specified by the standard body. In general SOMC through master IoT device of NPS controls all activities of slave IoT devices used by NPS. Both shared database and SOMC are located in a cloud used by all operators and service providers (IoT networks) through an open interface.

At 1002 the master IoT device that belongs to a moving, a flying and a stationary object share the information data of their NPS with the IoT network to be stored in the shared data base used by the SOMC. The information data consists of the master IoT device's location coordinates, the specification of the slave IoT devices (operating spectrum, operating bandwidth, supported modulations, and ERP capability), type of the object, and dimensions of the object. The master IoT device and slave IoT devices require having a minimum specification in order for the object to use its NPS.

At 1003 the master IoT device of each NPS (including NPS1 and NPS2) obtains the time of day (TOD). The TOD can be obtained from the IoT network (using one of IEEE1588 PTP, unused subcarriers, cyclic prefix), or GPS. TOD can also be obtained from another master IoT device in proximity within the smart environment.

At 1004 master IoT device obtains detail operation information data (OID) for the NPS1 from SOMC through IoT network. The OID includes frequency, channel, modulation, ERP, absolute times (start of time slot) and time slot duration for all objects in the smart environment. The start time is within a millisecond ($1^{st}$, $K_{th}$, $N_{th}$ and etc.). Duration is the time window of time slot assigned to each object for various activities (sensing, ranging, and etc.).

At 1005 master IoT device evaluates if it needs to perform a handover to another of its own IoT network's gNodeB/eNodeB or to roam to another IoT network. If it requires performing handover or roaming then it goes to 1006.

At 1006 master IoT device search for a new eNodeB/gNodeB from its own service provider or another service provider to handover or roam. Once the handover or roaming is completed it goes to 1001 or 1002 depending on circumstances.

If master IoT device does not require handover or roaming then it goes to 1007. At 1007 master IoT device shares the OID received from SOMC through the IoT network with NPS1's controller. Then controller at 1008 activate slave IoT devices.

At 1009 slave IoT devices obtain OID which includes the time of day (TOD) from NPS1's controller. The TOD is the same as master IoT device TOD and is exchanged between controller and slave IoT devices using IEEE1588 PTP messages. Slave IoT devices after synchronizing with master IoT device or controller and obtaining TOD continue at 1010.

At 1010 slave lot devices or/and master IoT device receive all parameters, information for broadcast packet, and all absolute times for the time slot (OID) to transmit a packet and receive a packet. The absolute time is the start of time slot or time window and is a microsecond within millisecond. The time slot or time window shows the time period that assigned to the slave or/and the master IoT device for receiving or transmitting a broadcast or an Ethernet packet. All slave IoT devices or/and master IoT device within the NPS1 use their own time slot to transmit broadcast or Ethernet packets and time slots assigned to other NPSs to receive broadcast packets and receive or transmit Ethernet packets.

At 2011 all slave IoT devices or/and master IoT device that belong to the NPS1 of object1 (moving, flying, and stationary) begin transmitting their broadcast packet or frame and receiving broadcast packets or frames from the IoT devices belonging to the NPSs of other objects in the surrounding smart environment.

At 1012 each slave IoT device or/and master IoT device (NPS1) receives broadcast packet at time sots assigned to the salve IoT devices or/and the master IoT devices of other objects in the smart environment. They measure broadcast packet's receive signal strength intensity (RSSI), detect information in the packet if RSSI is close to a threshold defined by the controller of the NPS1, and record address and time of day when time stamp within the broadcast packet arrived at their antenna ports.

At 1013 each slave IoT device or/and master IoT device uses RSSI of received broadcast packets, and a threshold matrix provided by NPS1's controller to obtain a rough estimate of its distance from IoT devices of the objects in the smart environment that transmitted the packets.

At 1014 each slave IoT device or/and master IoT device sends the RSS and the time slots of the received broadcast packets from IoT devices that belong to other objects to the NPS1's controller. For those detected broadcast packets the address, approximate distance, time stamp (T1), and time of day the time stamp T1 arrived at antenna port (T2) are also sent to NPS1's controller.

At 1015 the NPS1's controller of the object1 receives the detected information data (DID) and activates its Artificial Intelligent (AI) algorithm.

At 1016 the AI assesses all the data (DID) received from slave IoT devices or/and master IoT device and determines the nature of surrounding environment.

At 1017 AI determines if one or more slave IoT devices having objects that are getting close to them. If the result is negative then the process continues at 1011. If the result is positive then step 2018 is executed.

At 2018 the AI inspect if the IoT network has updated any operation information data (01D) that was shared with master IoT device and the NPS1's controller. If positive then at 1019 controller shares the updated OID with slave IoT devices and process continues at 1011. If there is no update then process continues at 1020.

At 1020 the AI identifies the slave IoT devices that have approaching objects and selects the time slots for them to transmit an Ethernet packet. The time slots are its own or belong to objects with negligible RSSI.

At 1021 each slave IoT device (object1, NPS1 from the process 2000) may use method 930 or 935 to estimate a distance of an approaching object. In the process 2000 method 930 is used. Each slave IoT device transmits its broadcast packet (with time stamp T1 in its payload which is the time of day at its antenna port) in the time slot assigned by SOMC. The slave IoT devices identified by the AI (NPS1) that face potential impact, in addition to transmitting their broadcast packet (T1) also transmit an Ethernet packet in the time slot assigned by the AI (NPS1). There are two types of Ethernet packets. One is an Ethernet packet which is sent to a slave IoT device (object2, NPS2) in smart environment that is identified by the AI (NPS1) as one with potential impact. This Ethernet packet uses the address of the broadcast packet received from the slave IoT device used by object2 (NPS2) and in its payload sends three TODs. The first TOD is the received time stamp TOD from the slave IoT device (object2, NPS2) with potential impact (T1). The second TOD (T2) is the time of day T1 was received at antenna port of the slave IoT device used by object1 (NPS1). The third TOD (T3) is the Ethernet time stamp at the antenna port of the slave IoT device belonging to object1 (NPS1). So the first type of Ethernet packet sends three TODs which are T1, T2, and T3. Master IoT device also acts as slave when needed.

The second type of Ethernet packet is a response by object1 (belong to NPS1) to an Ethernet packet from object2 (belong to NPS2) that received the broadcast packet from object1 (NPS1) by one of its slave IoT devices. The second type of Ethernet packet transmits five TODs in its payload. The first TOD (T1) is the time of day (time stamp) that the slave IoT device from object1 (NPS1) sent in its broadcast packet. The second TOD (T2) is the time of day when T1 received at the antenna port of the slave IoT device used by object2 (NPS2). The third TOD (T3) is the time stamp of Ethernet packet received from the slave IoT device of object2 (NPS2) by a slave IoT device of object1 (NPS1). The fourth TOD (T4) is when TOD (T3) is received at the antenna port of the slave IoT device used by object1 (NPS1). The four TODs are T1, T2, T3, and T4 are sent in the payload with a time stamp (T5) to slave IoT device used by object2 (NPS2). In a worst case AI of each NPS allows the slave and master IoT devices to transmit broadcast and Ethernet packets only at their own time slot assigned by SOMC.

At 1022 each slave IoT device (NPS1) measures RSSI of a received packet (broadcast or Ethernet) in an assigned time slot shared by SOMC through NPS1's controller. These assigned time slots are used by the slave and the master IoT devices in the smart environment. Slave and master IoT devices used by an object only transmit a broadcast packet (Ethernet packet if AI did not find any suitable time slot) at the assigned time slot for the object1 (NPS1) but receive broadcast and Ethernet packets during time slots assigned to other objects in the smart environment. The assigned time slots can be changed by SOMC when needed.

At 1023 slave or master IoT device (object1, NPS1) checks if measured RSSI is below a threshold. If the result is positive then at 1028 slave or master IoT device sends time slot and the RSSI of the received packet to controller 1032. If the result is negative then slave or master IoT device (NPS1) receives the entire packet and at 1024 checks if it is a broadcast packet. If the result is positive then at 1027 slave or master IoT device (NPS1) detects the address of the packet, and TOD T2 when packet time stamp T1 arrived at the antenna port of the slave or master IoT device (NPS1). Then Slave or master IoT device sends the address, RSSI, T1 and T2 to NPS1's controller 1032.

At 1025 the process 2000 checks if the packet is a response to an Ethernet packet sent by the slave or master IoT device of (object1, NPS1) to object2. If the result is positive then at 1026 slave or master IoT device (object1, NPS1) detects six TODs T1, T2, T3, T4, T5, and T6. T1 is the slave or master IoT device (object2, NPS2) time stamp received at the antenna port of slave or master IoT device (NPS1) of object1 at time of day T2. T3 is the Ethernet packet time stamp TOD at antenna port of slave or master IoT device of object1 (NPS1) sent to object2 (NPS2). T4 is the TOD when T3 arrived at the antenna port of slave or master IoT device of object2 (NPS2). T5 is the time stamp of response Ethernet packet and T6 is the TOD when T5 arrives at the antenna port of slave IoT device of object 1. The slave or master IoT device of object1 (NPS1) uses four TODs to calculate the distance between two objects and then sends type of packet, RSSI, time slot, six TODs, source address of Ethernet packet and distance to controller 1032. If the result is negative then process continues at 1029.

At 1029 slave or master IoT device (NPS1) checks whether the received Ethernet packet has object1 (NPS1) address in the destination address or not. If the destination address of the Ethernet packet is different from slave or master IoT device's (NPS1) address then at 1030 the packet is treated like a broadcast packet and the packet time stamp, the time stamp arrival time at antenna port, time slot, RSSI, and address of the Ethernet packet is sent to controller 1032.

At 1031 the Ethernet packet from object2 (NPS2) is detected and four TODs T1, T2, T3, T4, are obtained. T1 is the time stamp of slave or master IoT device that belongs to object1 (NPS1). T2 is the TOD when T1 arrived at the antenna port of the slave or master IoT device that belongs to object2 (NPS2). T3 is the time stamp of Ethernet packet received by object1 (NPS1) from object2. T4 is the TOD when T3 arrived at the antenna port of the slave or master IoT device that belongs to object1 (NPS1). Four TODs are used to calculate the distance between object1 and object2. Then distance, source address of Ethernet packet, four TODs, RSSI, and time slot is sent to controller 1032.

At 1032 controller receives all the detected information data (DID) from slave IoT devices and master IoT device and feed them to NPS1's AI algorithm for the next step. The data that is sent to controller is from all the time slots (all objects in the smart environment) assigned to each slave IoT device or master IoT device by the AI algorithm through the controller. The data belongs to a single measurement cycle at all the time slots. The AI algorithm evaluates the detected information data (DID) in order to make a decision and provide the operation information data (O1D) for next measurement cycle of all time slots by each slave IoT device or/and master IoT device (NPS1). The AI algorithm also checks if the time slots and absolute times are updated by SOMC and obtained by NPS1's controller through master IoT device. Each slave IoT device or master IoT device receives its own specific OID.

At 1033 the AI checks if IoT network has updated time slots and absolute times. If update has occurred then at 1034 the AI through the controller shares the new data with slave IoT devices and/or master IoT device with updated OID for each individual IoT device. Then the process continues at 1021.

At 1035 the AI determines if it has enough information to make a decision. If there is not sufficient information then AI defines OID for each individual slave IoT device and/or master IoT device and the process continues at 1021. If there is enough data to make a decision then process continues at 1036.

At 1036 the AI algorithm calculates distance and approaching speed of objects that are approaching slave IoT devices.

At 1037 the AI examines if both distance & approaching speed of an object detected by a slave IoT device meet certain threshold. If it does not meet then the process continues at 1041.

At 1038 the AI checks if there is an imminent impact. If there is not then the process continues at 1041.

At 1039 the AI analyses the entire detected information data (DID) and activates the appropriate protection devices.

At 1040 the AI through NPS1's controller and maser IoT device reports to the IoT network, then NPS1 waits for next step from IoT network. At this point when it is appropriate the NPS1 resets and at the right time it will be activated and process 2000 at 1001.

At 1041 the AI algorithm determines whether more information is needed in order to activate navigation devices such as steering wheel, break, accelerator, and etc. If there is not enough DID to decide then process 2000 continues at 1044.

At 1044 the AI identifies the required operation information data (OID) for each slave and/or master IoT device and sends it to them through controller. Once each individual slave IoT device or master IoT device is provided its new OID then the process continues at 1021.

At 1042 due to sufficient information for AI algorithm, navigation system is activated and more information data from surrounding environment is collected by other sensors (image, ranging) used by NPS1 to be used by AI algorithm. AI uses all the detected information data (DID) and provides required changes to various navigation devices such as steering wheel, break, accelerator, and etc.

At 1043 AI algorithm determines if there is any changes to the OID for each individual IoT device due to activating navigation. If there are not any changes then process 2000 continues at 1021.

At 1045 AI sends the updated OID to each IoT device through controller and the process 2000 continues at 1021.

Various embodiments are thus described. While particular embodiments have been described, it should be appreciated that the embodiments should not be construed as limited by such description, but rather construed according to the following claims.

The invention claimed is:

1. A navigation and protection system (NPS) used by an object in a smart environment comprising:
    a master Internet of Things (IoT) device to communicate with an IoT network and obtain a time of day (TOD) and an operation information data (OID) that includes an absolute time and a time slot for the NPS;
    a plurality of slave IoT devices to transmit and receive a broadcast packet and an Ethernet packet at said absolute time and during said time slot to send a time stamp and obtain a detected information data (DID) related to the objects in the smart environment using the time of day (TOD);
    a controller in a central processor unit (CPU) to manage said navigation and protection system and to:
        synchronize with the master IoT device to obtain said TOD and said operation information data;
        share the operation information data and the TOD with a slave IoT device within said plurality of slave IoT devices;
        collect said detected information data provided by said slave IoT device in said plurality of slave IoT devices; and
        feed said operation information data and said detected information data to an artificial intelligent (AI) algorithm executed by the controller;
    said AI uses said operation information data and said detected information data to:
        activate a protection device used by said NPS when an impact is detected;
        activate a navigation device to avoid the impact; or
        update the operation information data and send it to the slave IoT device through said controller.

2. The navigation and protection system of claim 1, wherein said object is at least one of a moving vehicle, a flying vehicle, a stationary object, a robot, and a live animal (human).

3. The navigation and protection system of claim 1, wherein said IoT network is at least one of a fifth generation (5G) network, a sixth generation (6G) network, a seventh generation (7G) network, a beyond 5G network, a WiFi (wireless fidelity) network, and a private network.

4. The navigation and protection system of claim 1, wherein said absolute time is at least one of a $1^{st}$ microsecond in a millisecond, a Kth microsecond in a millisecond, and a Nth microsecond in a millisecond.

5. The navigation and protection system of claim 4, wherein said time slot is a period assigned to the navigation and protection system (NPS) and starts from the absolute time that is assigned to the NPS.

6. The navigation and protection system of claim 2, wherein said plurality of slave IoT devices and said master IoT device are attached to external body of said object and communicate with said controller to receive said operation information data and to transmit said detected information data to be used by the AI.

7. The navigation and protection system of claim 1, wherein said operation information data includes at least one of said absolute time, the time slot assigned to the NPS to transmit and receive said broadcast packet and said Ethernet packet, the time slots said slave IoT devices can transmit said Ethernet packet, an operating frequency, a channel, a bandwidth, a modulation, and an effective radiation power (ERP).

8. The navigation and protection system of claim 1, wherein said DID includes at least one of said time stamp from said received broadcast packet or/and the Ethernet packet, the TOD said time stamp arrives at said salve IoT device's antenna port, a receive signal strength intensity (RSSI) of the received broadcast packet or/and the Ethernet packet, a source address of the received broadcast packet, a destination address of the received Ethernet packet, and said TODs used to estimate a distance and an approaching speed of another said object.

9. The navigation and protection system of claim 8, wherein said AI algorithm in addition to said DID uses data from other sensors or/and devices internal and external to said object to determine if there is a need to activate said protection device or/and said navigation device.

10. The navigation and protection system of claim 3, wherein said slave IoT device uses the over air protocol of at least one of said 4G, said 5G, said 6G, said 7G, said beyond 5G, said WiFi, a Bluetooth, a Zigbee, and an Infrared.

11. A method to navigate and protect an object in a smart environment, the method comprising:
   installing a navigation and protection system (NPS) on the object comprising:
   a master Internet of Things (IoT) device to communicate with an IoT network to obtain:
   a time of day (TOD); and
   an operation information data (OID) that includes an absolute time and a time slot for the NPS;
   a plurality of slave IoT devices to transmit and receive a broadcast packet and an Ethernet packet at said absolute time and during said time slot to:
   send and receive a time stamp indicating said TOD; and
   obtain a detected information data (DID) related to the objects in the smart environment that includes said time stamp;
   a controller in a central processor unit (CPU) to manage said navigation and protection system and to:
   synchronize with the master IoT device to obtain said TOD and said operation information data;
   share the operation information data and the TOD with a slave IoT device within said plurality of slave IoT devices;
   collect said detected information data provided by said slave IoT device in said plurality of slave IoT devices; and
   feed said operation information data and said detected information data to an artificial intelligent (AI) algorithm executed by the controller;
   said AI uses said operation information data and said detected information data to:
   determine if more said DID is required and request from the NPS's said slave IoT devices by sending them an updated OID;
   estimate a distance and an approaching speed using the time stamps provided by the slave IoT devices;
   detect an imminent impact and then activate a protection device; or
   activate a navigation device if a potential impact is detected.

12. The method of claim 11, wherein said slave IoT devices are sensors mounted on external locations of a body of the object.

13. The method of claim 11, wherein said protection device is at least one of a multilayer airbag, a compressed air, and an expandable pad.

14. The method of claim 11, wherein said navigation device is at least one of a steering wheel, an accelerator, a break, a horn, and a beam light.

15. The method of claim 11, wherein said broadcast packet contains at least one of a type, a location coordinates, and a mass of said object.

* * * * *